(12) United States Patent
Radjy et al.

(10) Patent No.: US 10,877,017 B2
(45) Date of Patent: Dec. 29, 2020

(54) SENSING DEVICE, AND SYSTEMS AND METHODS FOR OBTAINING DATA RELATING TO CONCRETE MIXTURES AND CONCRETE STRUCTURES

(71) Applicant: QUIPIP, LLC, Pittsburgh, PA (US)

(72) Inventors: Farrokh F. Radjy, Pittsburgh, PA (US); Anousha Radjy, Pittsburgh, PA (US)

(73) Assignee: QUIPIP, LLC, Pittsburgh, PA (US)

( * ) Notice: Subject to any disclaimer, the term of this patent is extended or adjusted under 35 U.S.C. 154(b) by 408 days.

(21) Appl. No.: 15/634,714

(22) Filed: Jun. 27, 2017

(65) Prior Publication Data

US 2017/0370898 A1     Dec. 28, 2017

Related U.S. Application Data

(60) Provisional application No. 62/355,263, filed on Jun. 27, 2016, provisional application No. 62/467,434, filed on Mar. 6, 2017, provisional application No. 62/482,784, filed on Apr. 7, 2017.

(51) Int. Cl.
    *G01N 33/38*     (2006.01)

(52) U.S. Cl.
    CPC .......... *G01N 33/383* (2013.01); *G01N 33/38* (2013.01); *G01N 2291/0231* (2013.01); *G01N 2291/0232* (2013.01); *G01N 2291/0255* (2013.01); *G01N 2291/0256* (2013.01)

(58) Field of Classification Search
    CPC ................. G01N 33/38; G01N 33/383; G01N 2291/0231; G01N 2291/0232; G01N 2291/0255; G01N 2291/0256; E02D 2300/002; E02D 29/0283; E02D 2600/10
    See application file for complete search history.

(56) References Cited

U.S. PATENT DOCUMENTS

| | | | |
|---|---|---|---|
| 10,041,928 B2* | 8/2018 | Berman | B28C 7/024 |
| 2009/0211754 A1* | 8/2009 | Verret | E21B 47/10 |
| | | | 166/250.12 |

(Continued)

OTHER PUBLICATIONS

International Search Report dated Sep. 13, 2017 from corresponding International Application No. PCT/US2017/039454.

(Continued)

*Primary Examiner* — Eman A Alkafawi
*Assistant Examiner* — Lynda Dinh
(74) *Attorney, Agent, or Firm* — Lucas & Mercanti, LLP

(57) ABSTRACT

A plurality of sensing devices are inserted into a concrete mixture to be used at a construction site. The concrete mixture is poured to form one or more structural elements, wherein one or more sensing devices are embedded in the concrete of each structural element. Data relating to a first characteristic of the concrete in each structural element is received from the sensing devices. For each structural element, a second characteristic of the concrete of the associated structural element is determined, based on the first characteristic. A map showing the one or more structural elements is generated. For each of the one or more structural elements, a respective graphical indicator indicating the second characteristic associated with the respective structural element is displayed on the map. The map is displayed on a user device.

16 Claims, 66 Drawing Sheets

(56) References Cited

U.S. PATENT DOCUMENTS

| | | | |
|---|---|---|---|
| 2014/0210494 A1* | 7/2014 | Ghods | G01N 27/026 324/700 |
| 2015/0014300 A1* | 1/2015 | Ciuperca | H05B 1/0227 219/494 |
| 2015/0212061 A1* | 7/2015 | Radjy | G01N 33/383 73/53.01 |
| 2016/0018383 A1 | 1/2016 | Radjy | |
| 2016/0328929 A1* | 11/2016 | Jesus De Sequeira Serra Nunes | A61B 5/02405 |
| 2017/0108456 A1* | 4/2017 | Alizadeh | G01M 5/0083 |
| 2017/0146487 A1* | 5/2017 | Pagani | G01N 33/383 |
| 2018/0238820 A1* | 8/2018 | Ghods | G01N 27/026 |

OTHER PUBLICATIONS

Written Opinion of the International Searching Authority dated Sep. 13, 2017 from corresponding International Application No. PCT/US2017/039454.

* cited by examiner

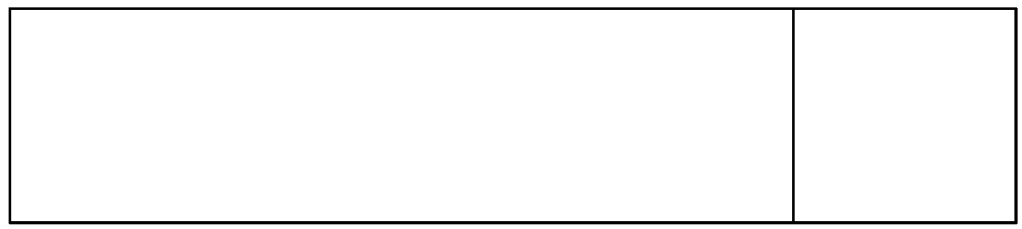
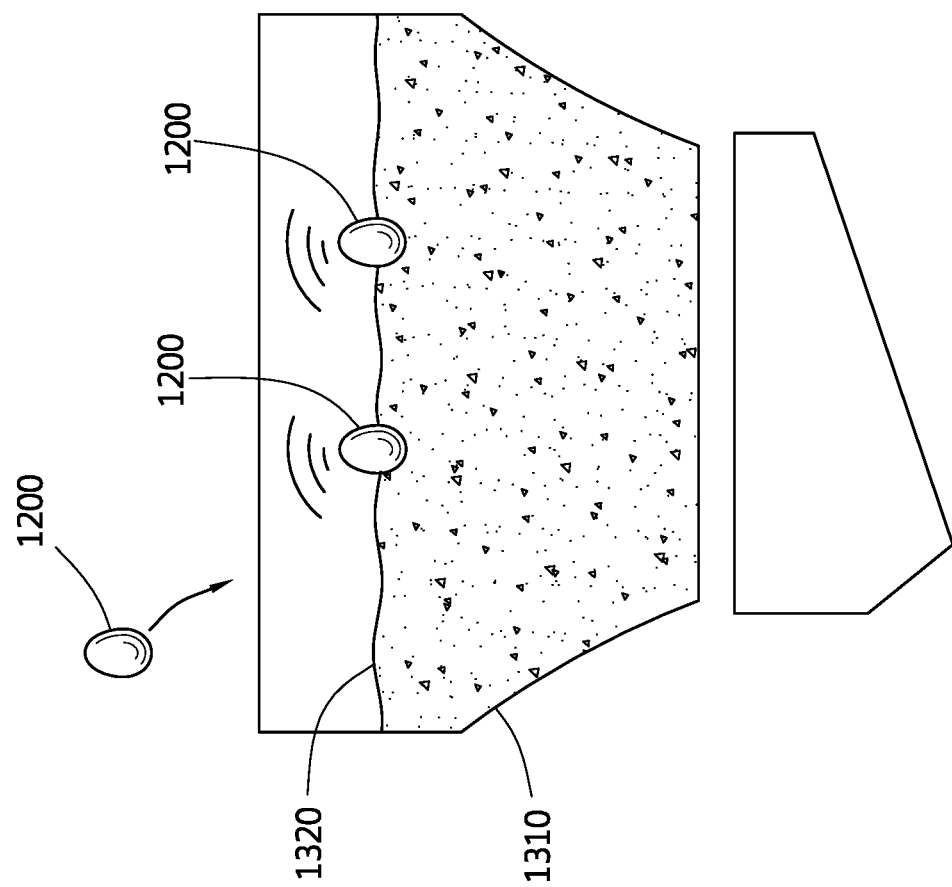
FIG. 13

SENSING DEVICE, AND SYSTEMS AND METHODS FOR OBTAINING DATA RELATING TO CONCRETE MIXTURES AND CONCRETE STRUCTURES

This application claims priority from U.S. Provisional Application No. 62/355,263 filed Jun. 27, 2016. This application claims the benefit of U.S. Provisional Application No. 62/467,434 filed Mar. 6, 2017 and U.S. Provisional Application No. 62/482,784 filed Apr. 7, 2017. The contents of each of these applications are incorporated herein by reference.

TECHNICAL FIELD

This specification relates to a systems, methods, and apparatus for obtaining data relating to condition and performance of concrete.

BACKGROUND

Concrete is a composite material including coarse granular materials such as sands and stones embedded in a hard matrix of materials such as hydrated cements. Concrete production is performed by mixing these ingredients with water to make a fluid concrete. Typically, the fluid concrete is transported and put in place before it is hardened.

After the ingredients are mixed with water, the fluid concrete is continuously mixed during transportation by a mixer truck in order to maintain a quality of the concrete. However, there is no way to monitor the quality of the transported fluid concrete in real time. In addition, there is no way, in real time, of knowing the location where, in a given project, the fluid concrete is poured and what its mixture proportions and physical properties are at that location. Nor is it possible to track the progress of a poured volume, automatically and in real time in order to achieve better economics and improved construction efficiency.

After the fluid concrete is poured at an intended location, the concrete and the concrete construction industries generally use compression strength and other destructive tests to determine the quality of concrete placed at various projects in accordance to different engineering and mix design specifications. In most instances, the strength of the concrete is specified to reach certain strength at a curing age of 28 days. This is because the needed hardening or curing time for concrete is traditionally considered to be 28 days. Accordingly, in this day of instantaneous information and communications, the concrete industry still waits 28 days before knowing concrete quality.

SUMMARY

Embodiments of the present invention comprise a wireless device, and systems and methods for measuring a property of a concrete, both a fluid concrete inside a drum of a mixer truck, and hardened or hardening concrete in a structure, and transmitting data relating to the measurement. Embodiments of the present invention are specifically adapted for managing or controlling in real time the quality of a fluid concrete after it is made, during transportation, placement in a structure, and curing and hardening in the structure.

In European practice and sometimes in the United States, wet mixing is practiced, which means that complete mixing occurs at the plant and the truck mixer's function is agitation. In contrast, in the United States, concrete is dry-batched into the truck and the truck mixer does the mixing.

In accordance with an embodiment, the wireless device can be defined as comprising:
a shell;
at least one sensor inside the shell for measuring a property of a fluid concrete;
a transmitter connected to the sensor for transmitting data from the sensor; and
a power source inside the shell and connected to the sensor and the transmitter,
the device having a weight less than a buoyancy of the device such that the device floats at the surface of the fluid concrete.

Suitably, the shell is spherical.
Suitably, the shell has a diameter between about 1 and 10 cm.
Suitably, the shell is made of a metal or plastic.
Suitably, the sensor includes at least one of a temperature sensor, an accelerometer, a pH sensor, an inductance sensor, an impedance or resistivity sensor, a sonic sensor, a pressure sensor, or an elevation sensor.
Suitably, the device further includes a Global Positioning System unit.
Suitably, the device further includes a passive or active radio frequency identification tag inside the shell.
Suitably, the device further includes a date and time recorder inside the shell.
Suitably, the device further includes a data storage component inside the shell.
Suitably, the shell includes a layer of a form plastic.
Suitably, an upper half of the device is lighter than a lower half of the device.
Suitably, the transmitter is placed in the upper half of the device and the sensor is placed in the lower half of the device.

In accordance with another embodiment, a system for measuring a property of a fluid concrete in a mixer truck can be defined as comprising:
the device; and
an antenna mounted in a side of a drum of a mixer truck for transmitting data from the device inside the drum to outside the drum.

Suitably, the system further includes a data receiving device receiving the date from the antenna.
Suitably, the data receiving device is connected to a database storing the data.

In accordance with another embodiment, a method for measuring a property of a fluid concrete in a mixer truck can be defined as comprising:
putting a wireless measuring device in a drum of a mixer truck;
pouring a fluid concrete into the drum of the mixer truck; and
collecting data for a property of the fluid concrete by the wireless measuring device.

Suitably, the method further includes:
transmitting the data from the wireless measuring device; and
receiving the data from the wireless measuring device.

In accordance with another embodiment, a method for determining a property of a fluid concrete mixture can be defined as comprising:
receiving data from a device floating in a concrete mixture inside a truck; and
determining a property of the concrete mixture, based on the data received from the device.

Suitably, the data comprises an indicator of a motion of the device, and the method further comprises:

determining a slump of the concrete mixture, based on the data.

Suitably, the data comprises one of a temperature measurement, a pH measurement, an inductance measurement, an impedance measurement, a resistivity measurement, a sonic measurement, a conductivity measure, a pressure measurement, and an elevation measurement.

In accordance with another embodiment, a method of manufacturing a measuring device can be defined as comprising:

softening a selected material;
pressing the softened material into a mold to form a first hemisphere;
depositing sensors into the first hemisphere;
joining a second hemisphere to the first hemisphere to form a sphere;
sealing a connection between the second hemisphere and the first hemisphere; and
injecting a selected gas into the sphere.

Suitably, the selected material comprises one of a metal, a plastic resin, and a polymer.

Suitably, the selected gas comprises nitrogen.

In accordance with an embodiment, a sensing device includes a shell comprising an elastomeric material, the shell including a first portion having a first end and a second portion having a second end. The shell may be egg-shaped or another shape. The first portion includes a thermally and electrically conducting disc, and a plate attached to the disc, the plate including a temperature sensor, a location sensor, and a micro-fiber composite sensor adapted to generate a measure of deformation, and an antenna, and a first electrode attached to the disc, the electrode extending through a first hole in the first portion of the shell. The second portion includes a predetermined quantity of a selected metallic substance embedded on the inside surface of an end of the second portion, and a second electrode connected to the metallic substance, the second electrode extending through a second hole in the second portion of the shell.

On another embodiment, the plate further includes one of an impedance/conductivity sensor, a pH sensor, an accelerometer, an elevation sensor, a RFID device, and a humidity sensor.

In another embodiment, the selected metallic substance comprises one of copper and brass.

In another embodiment, the thermally and electrically conducting disc is disposed perpendicular to an axis of the sensing device.

In another embodiment, the plate is perpendicular to the thermally and electrically conducting disc.

In accordance with another embodiment, a plurality of sensing devices are inserted into a concrete mixture at a production facility, first data is received from the plurality of sensing devices while the plurality of sensing devices are in the concrete mixture at the production facility, second data is received from the plurality of sensing devices while the plurality of sensing devices are in the concrete mixture in a vehicle transporting the concrete mixture to a construction site, third data is received from the plurality of sensing devices while the plurality of sensing devices are in the concrete mixture after the concrete mixture has been laid at a construction site, the first, second and third data are stored in a memory, and a prediction of a characteristic of the concrete mixture is generated based on the first, second and third data.

In one embodiment, the method also includes causing the concrete mixture and the plurality of sensing devices to be transported on a vehicle.

In another embodiment, the characteristic includes one of concrete strength and slump.

In another embodiment, fourth data representing a deformation is received from the MFC sensor, and an estimate of a slump of the concrete mixture is determined based on the fourth data.

In accordance with another embodiment, a method of managing a closed-loop production and delivery system is provided. An order for a product is received, wherein the order defines a formulation that specifies a plurality of components of the product and a quantity of sensing devices. In response to the order, the product is produced based on the formulation. The specified quantity of sensing devices are inserted into the product. Data is received from the sensing devices at one or more stages of production and delivery. A characteristic of the product is determined based on the data.

In one embodiment, the product is a concrete mixture.

In another embodiment, each sensing devices includes an egg shaped sensing device that includes a temperature sensor and an antenna.

In another embodiment, the characteristic includes one of concrete strength and slump.

In another embodiment, the product is one of a food products, a paint product, a petroleum-based product, and a chemical product.

In accordance with another embodiment, a measuring device is embedded in a section of concrete at a location at a construction site, the measuring device being adapted to obtain a measurement of a first characteristic of the section of concrete and transmit the measurement via wireless transmission. An airborne drone is flown above the construction site, the airborne drone comprising a wireless receiver and a wireless transmitter. Data representing the measurement is received by the airborne drone, and transmitted, by the airborne drone, to a processor. The processor generates a predicted second characteristic of the section of concrete based on the measurement. For example, the second characteristic may include strength, sump, age, maturity, etc., of the concrete.

In accordance with another embodiment, a method is provided. A plurality of sensing devices are inserted into a concrete mixture to be used at a construction site. The concrete mixture is poured at the construction site to form one or more structural elements, wherein one or more sensing devices are embedded in the concrete of each structural element. Data relating to a first characteristic of the concrete is received, from each of the plurality of sensing devices in the associated structural element. For each structural element, a second characteristic of the concrete of the associated structural element is determined based on the data relating to the first characteristic. A map showing the one or more structural elements is generated. For each of the one or more structural elements, a respective graphical indicator indicating the second characteristic associated with the respective structural element is displayed on the map. The map is displayed on a user device.

In one embodiment, each of the plurality of sensing devices includes one of a temperature sensor, an accelerometer, a pH sensor, an inductance sensor, an impedance or resistivity sensor, a sonic sensor, a pressure sensor, a conductivity sensor, a salinity sensor, a humidity sensor, and an elevation sensor.

In another embodiment, the first characteristic includes one of temperature, pH, inductance, impedance, resistivity, pressure, conductivity, salinity, and humidity. The second characteristic may include one of strength, maturity, and slump.

In accordance with another embodiment, a method is provided. One or more sensing devices are placed within concrete. Measurement data is received from the one or more sensing devices. A specified temperature and a desired measure of strength are received. A predicted time when the concrete is expected to have the desired measure of strength is determined, based on the specified temperature and the measurement data.

In accordance with another embodiment, a method is provided. One or more sensors are placed with a concrete structure that is being constructed. An upcoming action related to the construction of the concrete structure is identified. A required measure of strength that the concrete in the concrete structure must have before that action can be performed is determined. Data relating to measurements of one or more characteristics of the concrete in the concrete structure is obtained from the one or more sensors. A prediction of the future strength of the concrete in the concrete structure is determined, based on the data received from the one or more sensors. An estimated future time when the strength of the concrete in the concrete structure is expected to equal the required measure of strength is determined, based on the prediction of future strength. An alert indicating the estimated future time and the estimated future strength of the concrete is transmitted. A prediction of the current strength of the concrete in the concrete structure is determined, based on the data received from the one or more sensors. A determination is made that the predicted current strength of the concrete in the concrete structure equals the required measure of strength. An alert indicating that he predicted current strength of the concrete in the concrete structure equals the required measure of strength is transmitted. The upcoming action is performed, based on the determination that the predicted current strength of the concrete in the concrete structure equals the required measure of strength.

In one embodiment, a sensor device may have a housing with a square or rectangular shape, with a first side having a length between about 1.5 inch and about 2.0 inches, a second side having a length between about 1.5 inch and about 2.0 inches, and a thickness between about one-eight inch and one-half inch. In a preferred embodiment, a sensor device has a housing with a square shape with sides having a length of about one and three-fourths (1.75) inches, and a thickness of about three-sixteenth (3/16) inches.

BRIEF DESCRIPTION OF THE DRAWINGS

These and other aspects of the present Invention will be more fully understood by reference to one of the following drawings.

FIG. 13 shows a plurality of sensing devices disposed in a concrete mixture while the mixture is in a bin at a concrete production facility in accordance with an embodiment;

DETAILED DESCRIPTION OF THE INVENTION

Figure 1:
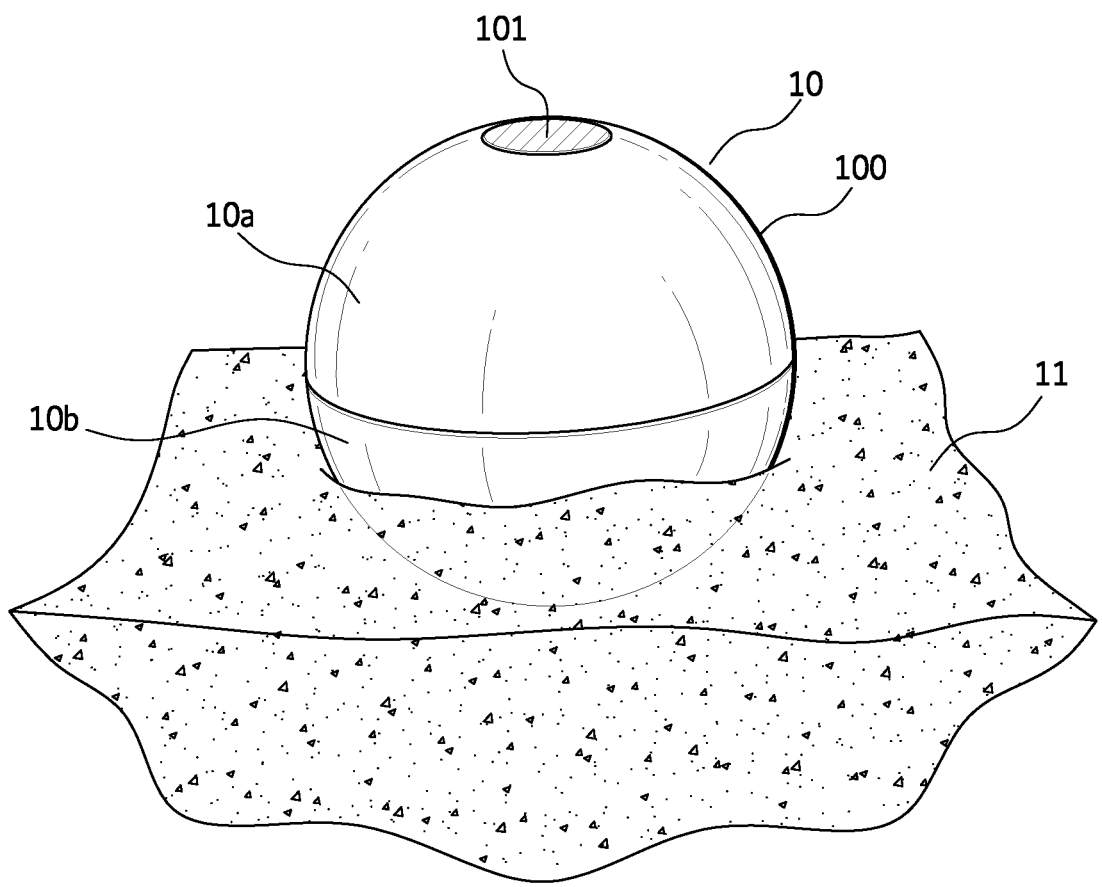
FIG. 1 is a perspective view of one embodiment of the floating wireless measuring device in accordance with an embodiment.

FIG. 1 shows a perspective view of one embodiment of a floating wireless measuring device 10. The floating wireless measuring device 10 in FIG. 1 is illustrated having a shell 100 and a transmitter 101. In FIG. 1, the floating wireless measuring device 10 floats at the surface of a fluid concrete 11 because the device 10 has a weight less than a buoyancy of the device 10.

When the device 10 floats at the surface of the fluid concrete 11, at least a part of an upper half 10a is above the surface of the concrete 11. Preferably, the transmitter 101 is placed in the upper half 10a of the device 10 above the surface of the concrete 11. The upper half 10a of the device 10 can be lighter than a lower surface 10b to stabilize the device 10 at the surface of the concrete 11.

The shell 100 can have any suitable diameter. Preferably, the diameter of the shell 100 is smaller than the diameter of an outlet of a drum of a concrete mixer truck. For example, the diameter of the shell 100 can be between about 1 cm and 10 cm, preferably about 3 cm and 8 cm, or more preferably about 4 cm and 6 cm. Alternatively, the diameter of the shell 100 can be at most about 5 cm, for example between about 3 cm and 5 cm.

The shell 100 can be made of any suitable material which can survive agitations of a concrete mixer truck and pumping of a fluid concrete or pouring the fluid concrete into structure by conventional methods. Preferably, the shell 100 is made of at least one of a metal such as steel, stainless steel, titanium, or aluminum; a plastic resin such as a tough plastic resin or a reinforced plastic resin; or any combination thereof.

The shell 100 can additionally include a foam resin layer. The form resin layer can be made of any appropriate polymer such as polystyrene. The foam resin layer can cover the entire surface of the shell 100, but alternatively the foam resin layer can partially cover the shell 100. For example, the foam resin layer can cover only the upper half 10a of the device 10. The foam resin layer can be formed to protect the device 10 from an impact or help the device 10 float at the surface of the fluid concrete.

Although the floating wireless measuring device 10 is illustrated having the spherical shape, the device 10 can be any suitable shape to be floated at the surface of the fluid concrete 11. Accordingly, the device 10 can be polyhedral, for example, cubic.

Figure 2:
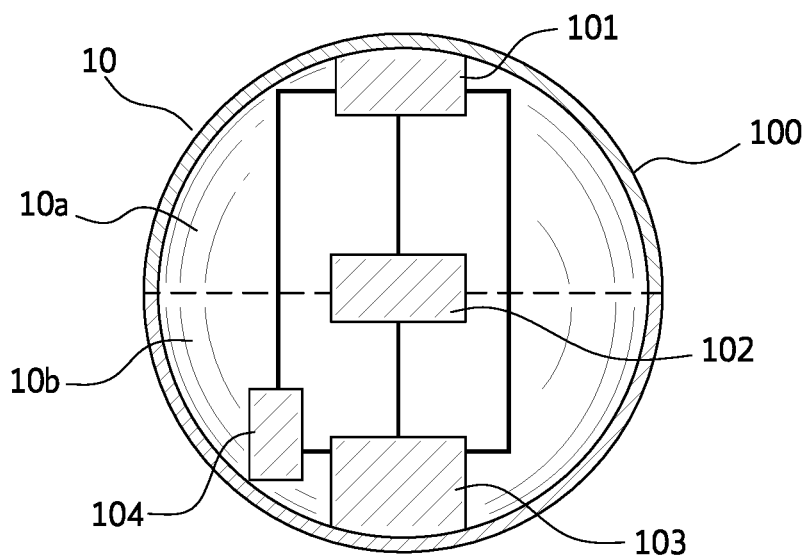
FIG. 2 is a cross-section view of one embodiment of the floating wireless measuring device in accordance with an embodiment.

FIG. 2 shows an embodiment of a vertical cross-section view of the floating wireless measuring device 10 illustrated in FIG. 1. The floating wireless measuring device 10 includes a sensor 103 for measuring a property of a fluid concrete, a transmitter 101 connected to the sensor 103 for transmitting data from the sensor 103, a power source 102 connected to the sensor 103 and the transmitter 101, and an additional component 104 connected to the transmitter 101, the sensor 103 and the power source 102.

The sensor 103 can be any kind of sensors that can be installed inside the shell 100 and measure a property of a fluid concrete. For example, the sensor 103 can be at least one of a temperature sensor, an accelerometer, a pH sensor, an inductance sensor, an impedance or resistivity sensor, a sonic sensor, a pressure sensor, a conductivity sensor, a salinity sensor, a humidity sensor, or an elevation sensor. One example of the temperature sensor is a miniature-sized temperature logger "SMARTBUTTON" (ACR SYSTEMS INC.). In one embodiment, a salinity sensor may include a chloride ion electrode, for example.

Concrete's temperature measured by the temperature sensor can be converted to maturity and real time concrete setting and strength estimation in combination with real time data relating to mixture proportions, and materials items batched, and by reference to calibration data in a central database. The accelerometer can inform of whether the device 10 is in motion or stationary. The elevation sensor can inform how high the device 10 is elevated after a fluid concrete is poured at a construction site. The inductance sensor and the impedance or resistivity sensor can give data about the strength and setting, as well as its water-cement ratio. For example, before a fluid concrete sets, the pores of the concrete are full of water with electrolytes such as Na, K, Ca, and the like rendering the pure solution conducting and thus appearing as a secondary coil. The measurements by these sensors can be used for in-situ reporting of mixture proportions.

The transmitter 101 can be any commercially-available transmitter which can be installed in the shell 100 and transmit data obtained from the sensor 103. For example, the transmitter 101 is a wireless chip for short distance transmission.

The transmitter 101 can be installed to an upper half 10a of the device 10, while the sensor 103 can be installed to a lower half 10b of the device 10. Preferably, at least a part of the upper half 10a is above the surface of a fluid concrete, while at least a part of the lower surface 10b of the device 10 contacts the fluid concrete. Accordingly, it is preferable that the sensor 103 is installed in the lower half 10b to measure a property of the fluid concrete, and the transmitter 101 is installed in the upper half 10a above the surface of the concrete to transmit data from the sensor 103.

The additional component 104 is, for example, a Global Positioning System (GPS) unit, a Radio Frequency Identification (RFID) tag, a time and date recorder, a data storage component, or any combination thereof. The additional component 104 can appropriately connect the transmitter 101, the power source 102, and the sensor 103. When two or more additional components are used, they can appropriately connect each other. However, it is possible that the additional component 104 is not included in the device 10.

The GPS unit can inform where the device 10 is during transporting a fluid concrete and when the concrete is poured at a construction site. The RFID tag can be read by a tag reader. The RFID tag can be another way of tracking concrete pours and the location of each pour. RFID tags may be used to uniquely link and identify each device 10 with a batch ticket associated with a truck load, for example. Thus, the device may be linked to its mix parent and physical batch result within a closed loop production system.

The location of the additional component 104 inside the shell 100 can be appropriately decided. Whether the additional component 104 is placed in the upper half 10a or the lower half 10b of the device 10 can be suitably decided.

The transmitter 101, the power source 102, the sensor 103, and the additional component 104 can be connected by any known means.

Figure 3:
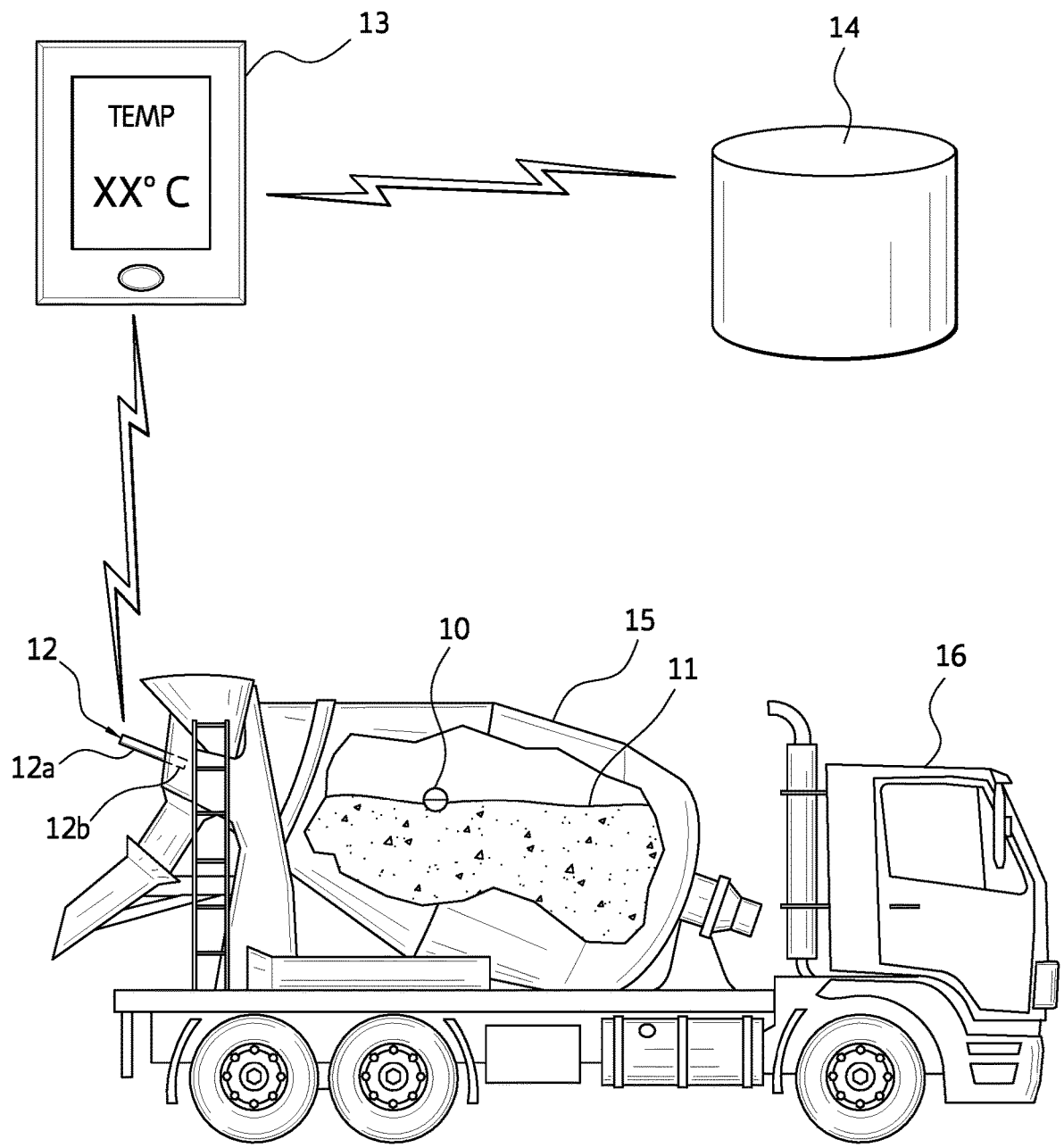
FIG. 3 is an overview of one embodiment of the system for measuring a property of a fluid concrete in a mixer truck in accordance with an embodiment.

FIG. 3 shows a system for measuring a property of a fluid concrete 11 in a mixer truck 16. The system includes the floating wireless measuring device 10 and an antenna 12 mounted in a side of a drum 15 of the mixer truck 16. The antenna 21 transmits data from the device 10 inside the drum 15 to outside the drum 15.

The device 10 can be put in the drum 15 before or at batching time, or after the truck 16 is loaded with the fluid concrete 16. For example, the device 10 can be shot into the drum 15 by a gun device. When the device 10 is shot into the truck at batching time, for example, an accelerometer in the device 10 can start a date and time recorder in the device 10 for measuring concrete age and recording when each type of measuring is transmitted.

When the fluid concrete 11 is not agitated in the drum 15, the device 10 floats at the surface of the concrete 11 and can transmit data.

The antenna 12 can comprise an outward looking wireless transmitter 12a and an inward looking wireless receiver 12b. The inward looking wireless receiver 12b can receive data from the device 10. The outward looking wireless transmitter 12a can transmit data from the device to a receiving device 13. The receiving device 13 can be a mobile device such as a cell phone. The receiving device 13 can send the data to a database 14. The database 14 can connect with the receiving device 13 with any know means such as a wireless connection.

The floating capability of the floating wireless measuring device 10 and the antenna 12 placed in a side of the drum 15 overcome the issues of not being able to transmit from within a conducting medium such as the fluid concrete 11 and the Faraday cage effect of the drum 15 of the mixer truck 16.

The method for measuring a property of a concrete will now be explained. As shown in FIG. 3, a property of the fluid concrete 11 in the mixer truck 16 can be measured by putting the wireless measuring device 10 in the drum 15 of the mixer truck 16; pouring the fluid concrete 11 into the drum 15 of the mixer truck 16; and correcting data for a property of the fluid concrete 11 by the wireless measuring device 10. This method can further include transmitting the data from the wireless measuring device 10; and receiving the data from the wireless measuring device 10. After pouring the fluid concrete 11 at a construction site, the device 10 can be poured with the concrete 11. The device 10 can measure in real time a property of the poured fluid concrete 11 during its hardening.

Advantageously, device 10 may be used to determine properties of the fluid concrete mixture while the concrete is inside of a truck. This capability may provide to a producer, or to a manager at a construction site, valuable information about the concrete prior to laying down the concrete.

Figure 4:
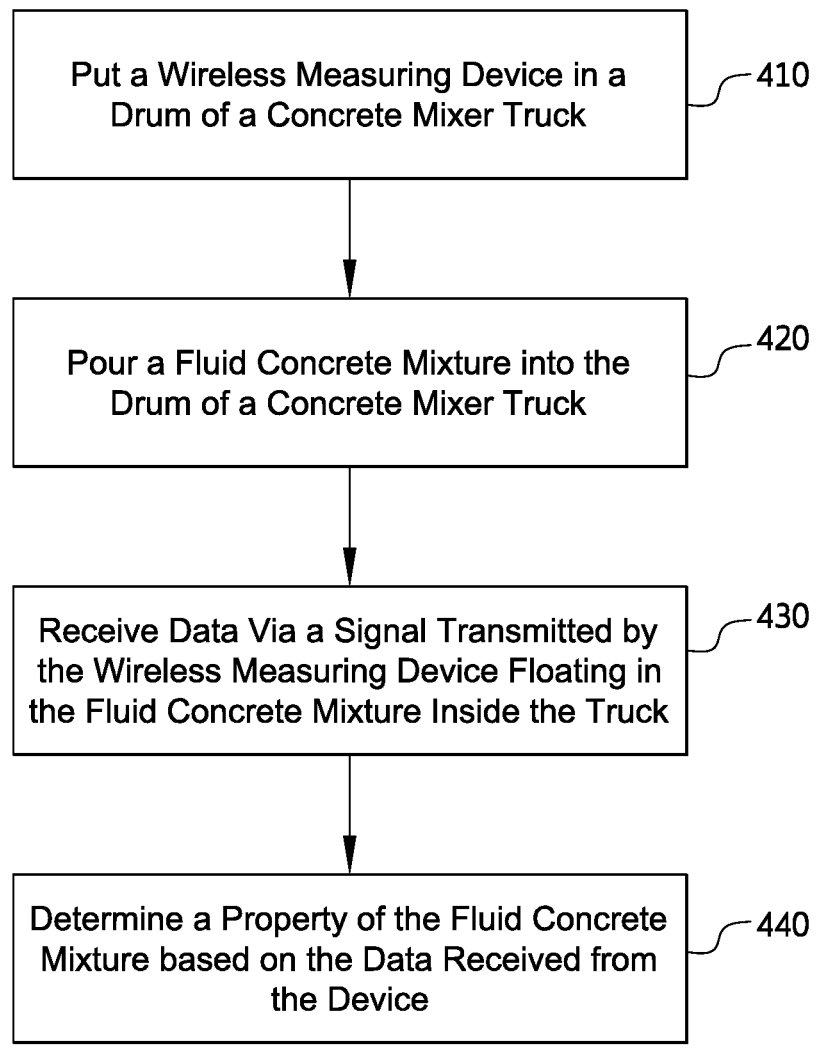
FIG. 4 is a flowchart of a method of determining a property of a concrete mixture in accordance with an embodiment.

For example, in an illustrative embodiment, device 10 may be used to determine a property, such as the slump, of a fluid concrete mixture while the concrete is inside of a truck. FIG. 4 is a flowchart of a method of determining a property of a fluid concrete mixture in accordance with an embodiment. At step 410, a wireless measuring device is put in a drum of a mixer truck. At step 420, a fluid concrete mixture is poured into the drum of the mixer truck. As described above, device 10 is put inside drum 15 of truck 16, and fluid concrete 11 is poured into the drum. As the drum 15 is agitated, the fluid concrete 11 moves and device 10 moves in the fluid concrete.

In other embodiments, dry components of concrete (instead of fluid concrete) are inserted into the drum of the mixer truck. Water is then added into the drum to produce fluid concrete. Device 10 may be added into the drum at any time during this process. Device 10 may be added to dry components of concrete or to fluid concrete.

In the illustrative embodiment, device 10 comprises an accelerometer and generates data indicating certain aspects of the device's motion. Device 10 may also include a GPS unit capable of generating location data. In other embodiments, other types of data, concerning various parameters relating to the device itself, or relating to the truck 16, or relating to the properties of the fluid concrete 11 inside the truck 16, may be obtained from a device floating in the fluid concrete 11 inside the truck 16.

At step 430, data is received via a signal transmitted by a device floating in a concrete mixture in a truck. In the illustrative embodiment, device 10 transmits signals containing motion data. The signals may also contain location data produced using the device's GPS capabilities. As described above, the signals are detected by antenna 12 and transmitted to receiving device 13 outside of the truck 16.

Device 13 receives the signals and extracts the motion data and location data from the signal. The motion data and location data may be stored in database 14, for example.

At step 440, a property of the concrete mixture is determined based on the data received from the device. In the illustrative embodiment, device 13 determines the slump of the fluid concrete 11 based on the motion data and location data received from device 10. The slump of a fluid concrete mixture may be determined from the motion data and location data using well-known methods.

In other embodiments, other properties of a fluid concrete mixture may be determined based on data received from device 10. For example, data from device 10 may be used to determine the water/cementitious ratio of a concrete mixture inside a truck.

In another embodiment, a plurality of devices similar to device 10 may be shot into drum 15, and float in the fluid concrete mixture inside the truck 16. Any number of devices may be shot into drum 15. In one embodiment, about one hundred (100) devices may be shot into the drum 15. When the concrete mixture is laid down at a construction site, the devices are allowed to remain in the mixture; the devices remain in the concrete as the concrete hardens, and thereafter. Each device continues to transmit data concerning various measurements as long as possible (e.g., until transmission is no longer possible or until the device's power source fails). For example, each device may transmit location data, temperature readings, pH measurements, inductance measurements, impedance measurements, resistivity measurements, sonic measurements, pressure measurements, conductivity measurements, elevation measurements, etc.

Figure 5:
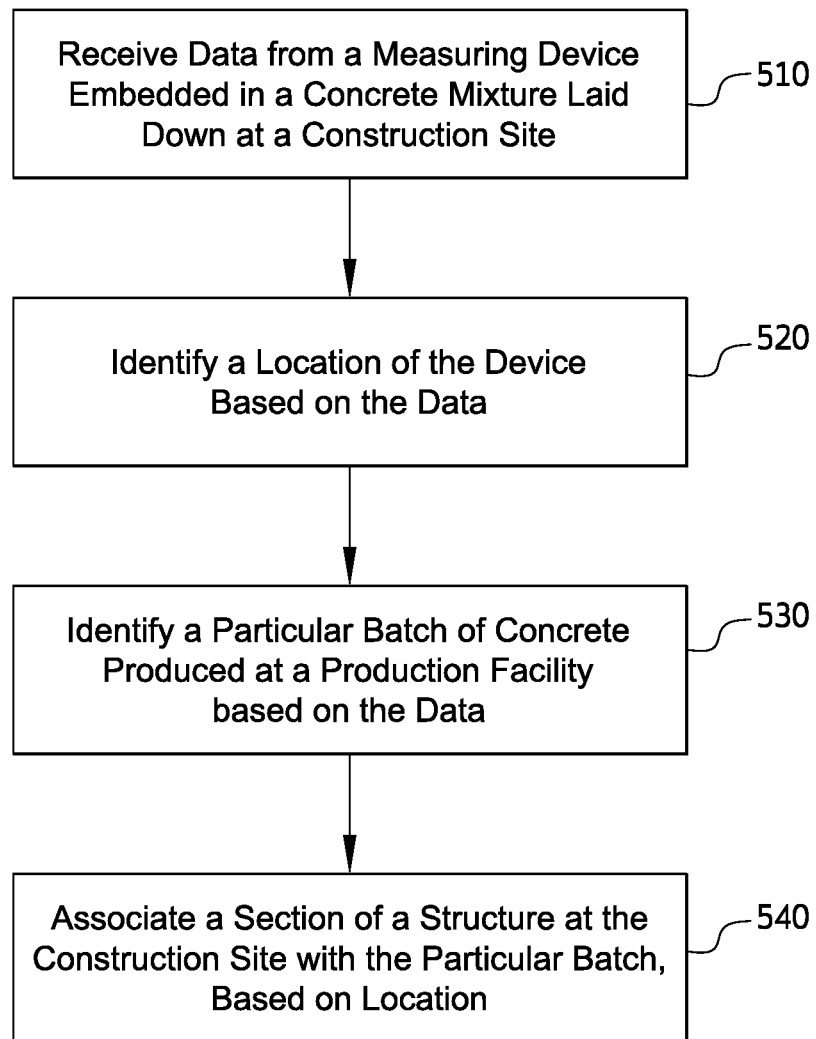
FIG. 5 is a flowchart of a method of associating a batch of a fluid concrete mixture with a section of a structure at a construction site in accordance with an embodiment.

FIG. 5 is a flowchart of a method in accordance with an embodiment. Suppose, in an illustrative example, that a plurality of devices (such as device 10) are shot into drum 15 and subsequently remain in the fluid concrete 11 as the concrete is laid down. Suppose further that the construction project requires ten truckloads of concrete. For convenience, in this example, each truckload represents one batch. Data received from the devices may be used to keep track of where each respective batch is laid. Thus, at step 510, data is received from a measuring device embedded in a concrete mixture laid down at a construction site. Data including location data, elevation data, etc., is received from one or more devices embedded in the concrete that has been laid down. At step 520, a location of the device is identified based on the data. The location data from a particular device may indicate that the device is located in a particular section of a parking lot, for example. At step 530, a particular batch of concrete produced at a production facility is identified based on the data. The device may provide identifying information from which it may be determined which truck the device was in. For example, each device may transmit a unique identifier. Knowledge of which truck the device was in may be used to determine the batch of concrete that the device is in. At step 540, a section of a structure at the construction site is associated with the particular batch, based on the location; for example, a linkage may be established between an RFID tag of a device and the batch when the device is introduced into concrete at the production facility, discharge chute or pump, or manually thrown into a structural element. The batch of concrete may then be associated with the identified section of the structure at the construction site (e.g., the section of the parking lot). Data associating respective batches with respective locations at a construction site may be stored for future use.

Using a plurality of devices in this manner advantageously enables a producer, or the manager of the construction site, to monitor the progress of a construction project. Leaving one or more devices in the concrete at the worksite also advantageously enables a producer or site manager to monitor when and where each particular batch or truckload of concrete is laid down. Possession of such information may enable a producer to monitor the performance of each batch of concrete produced, and thereby to achieve better control over the quality of the final product.

In another embodiment, a device similar to device 10 may store measurement data in a memory within the device without transmitting the data. The device may be retrieved at a later time, for example, when the concrete mixture is laid down, and the data retrieved from the device's memory.

Figure 6:
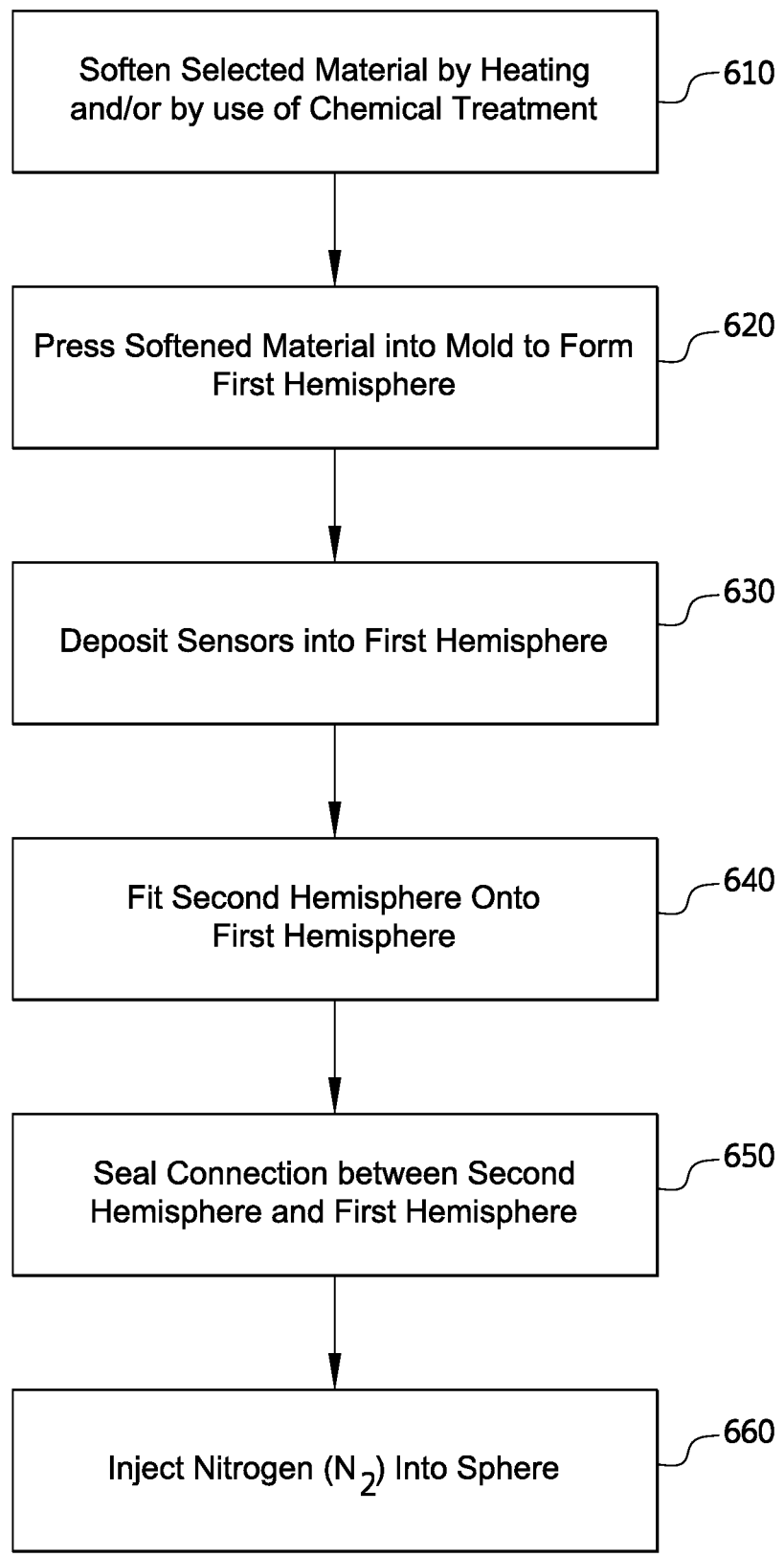
FIG. 6 is a flowchart of a method of manufacturing a measuring device in accordance with an embodiment.

In accordance with another embodiment, a method of manufacturing a measuring device such as device 10 is provided. FIG. 6 is a flowchart of a method of manufacturing a measuring device in accordance with an embodiment. At step 610, a selected material is softened by heating and/or by use of chemical treatment. For example, in an embodiment in which a polystyrene material is used, the polystyrene is heated, causing the material to soften.

Figure 7:
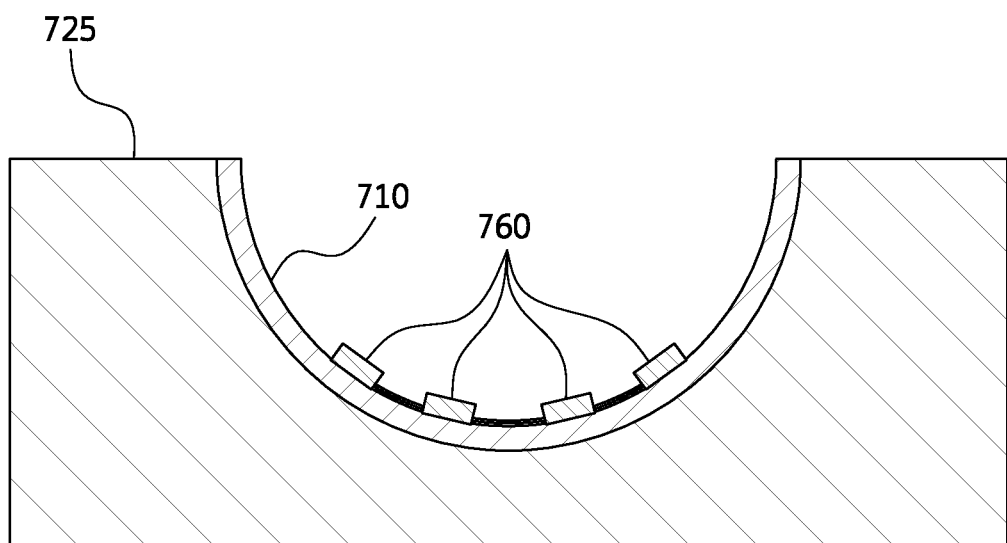
FIG. 7 shows a cross section of a mold in which a softened material has been pressed in accordance with an embodiment.

At step 620, the softened material is pressed into a mold to form a first hemisphere. FIG. 7 shows a cross section of a mold 725 in which a softened material 710 has been pressed in accordance with an embodiment. The mold forms a hemispherical shape.

At step 630, sensors are deposited into the first hemisphere. In the illustrative embodiment of FIG. 7, sensors 760 are embedded in the exposed internal surface of softened material layer 710, while the material is in the mold.

Figure 8A:
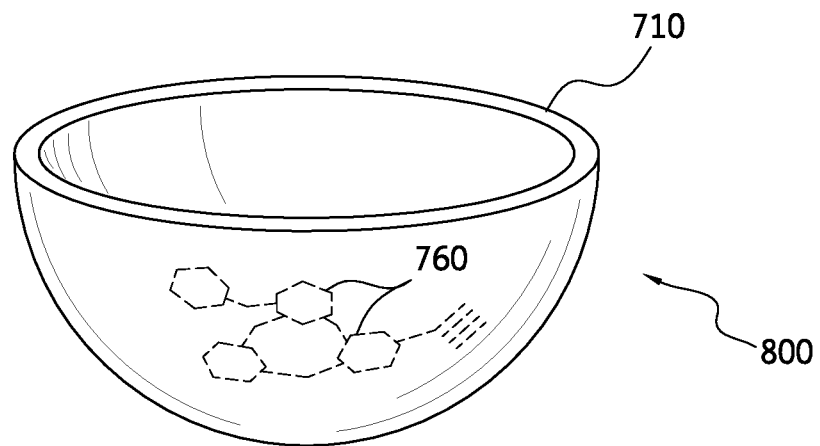
FIGS. 8A-8B show a side view and a top view, respectively, of a hemisphere formed of a material layer, after removal from a mold in accordance with an embodiment.
Figure 8B:
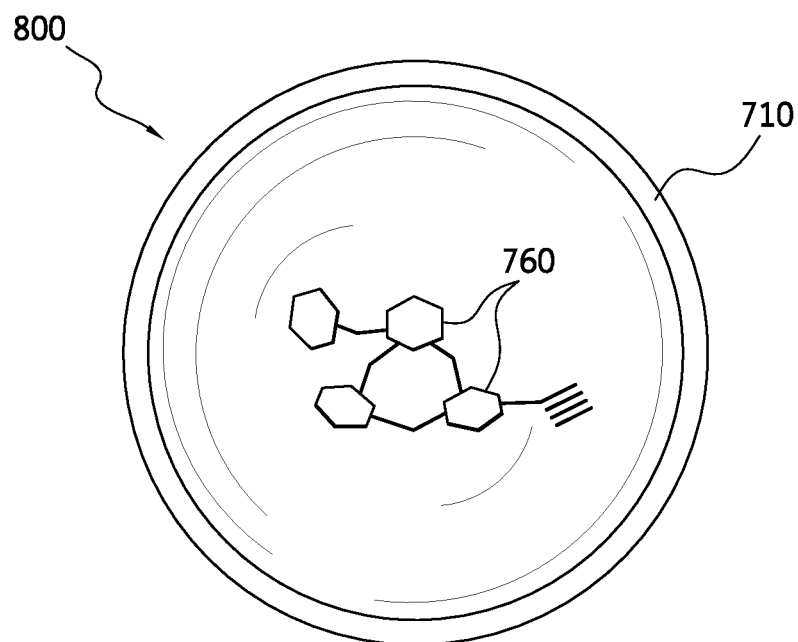

After the material hardens, the hemisphere may be removed from mold 725. FIGS. 8A-8B show a side view and a top view, respectively, of a hemisphere 800 formed of material layer 710, after removal from mold 725 in accordance with an embodiment. Sensors 760 are embedded on the inside surface of hemisphere 800.

Figure 9:
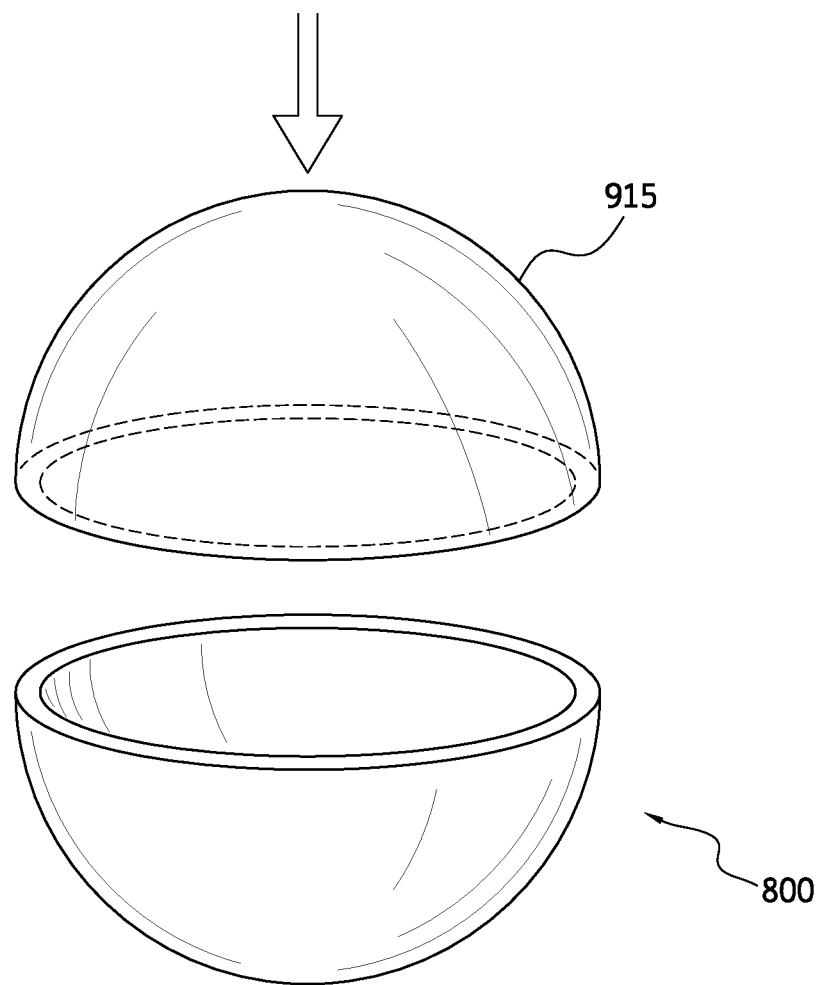
FIG. 9 shows a second hemisphere attached to a first hemisphere in accordance with an embodiment.
Figure 10:
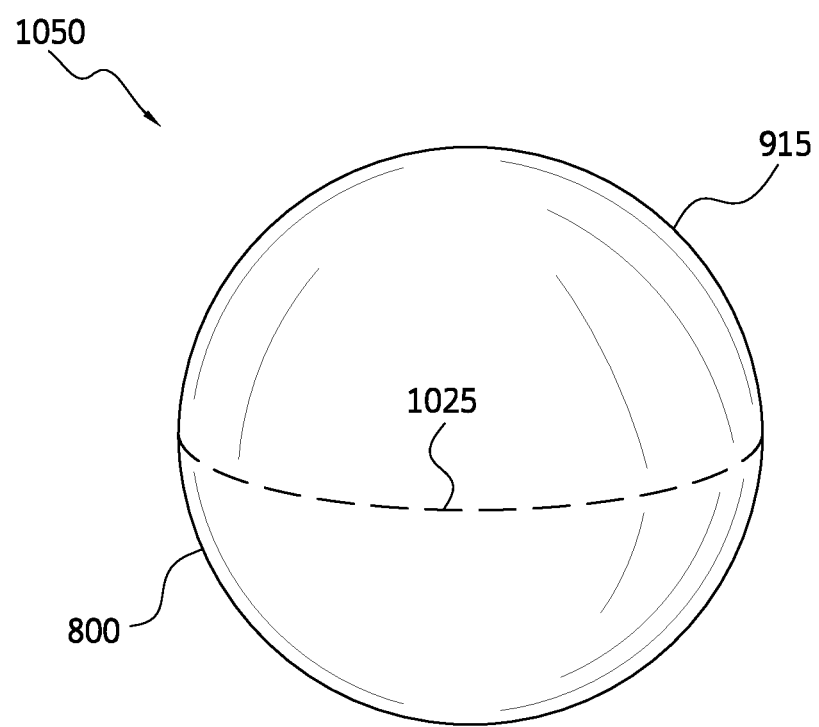
FIG. 10 shows a sphere comprising a first hemisphere, a second hemisphere, and a connection in accordance with an embodiment.

At step 640, a second hemisphere is fitted onto the first hemisphere, creating a sphere. In an illustrative embodiment shown in FIGS. 9-10, a second hemisphere 915 is fitted onto first hemisphere 800, forming a shell 1050 which is in the form of a sphere. Second hemisphere 915 may a hemisphere manufactured in a manner similar to that described above; however, second hemisphere 915 may, or may not, comprise sensors. Hemispheres 800 and 915 are joined at a connection 1025.

At step 650, the connection between the first hemisphere and the second hemisphere is sealed. In the illustrative embodiment, connection 1025 is sealed, for example, by using an appropriate glue.

At step 660, nitrogen ($N_2$) is injected into the sphere. Known techniques may be used to pump nitrogen into spherical shell 1050. In other embodiments, other gases may be used.

Figure 11:
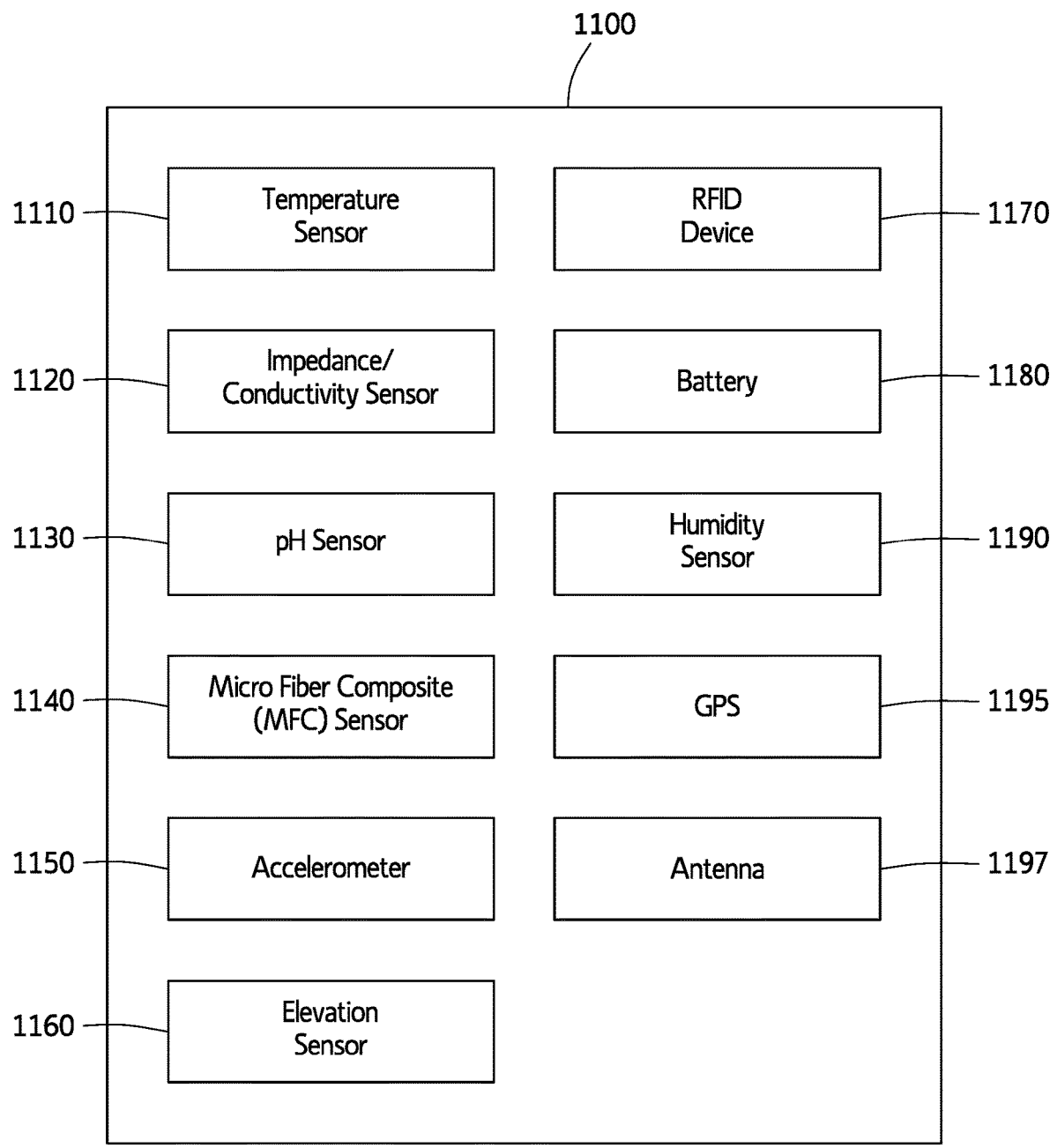
FIG. 11 shows components of a sensing device in accordance with another embodiment.

FIG. 11 shows components of a sensing device in accordance with another embodiment. Sensing device 1100 includes a temperature sensor 1110, an impedance/conductivity sensor 1120, a pH sensor 1130, a micro fiber composite (MFC) sensor 1140, an accelerometer 1150, an elevation sensor 1160, a radio frequency identification (RFID) device 1170, a battery 1180, a humidity sensor 1190, a GPS-based geolocation sensor 1195, and an antenna 1197. In another embodiment, sensing device 1100 may include a salinity sensor. For example, a salinity sensor may include a chloride ion electrode.

Temperature sensor 1110 detects the temperature of a concrete mixture or of another fluid in which the sensing device is floating. Temperature information can be used to analyze concrete maturity. For example, curing rate temperature dependency may be analyzed using the ASTM C74 method. In-place, in-structure strength may be estimated probabilistically as a function of curing age. Because concrete gains strength by maturity, it is valuable to builders to be able determine its curing age at a standard reference temperature.

Impedance/conductivity sensor 1120 measures the impedance and conductivity of concrete. Impedance and conductivity measurements may be used to determine real-time strength estimates, for example. Real-time strength estimates may be corrected for unrecorded water additions on the basis of real-time conductivity measurements. Conductivity of a concrete mixture decreases with age and correlates with the degree of hydration. DC conductivity may be measured. Alternatively, AC conductivity may be measured.

pH sensor 1130 measures the pH of a concrete mixture. pH measurements may capture unexpected overly retarded or accelerated setting due to concrete/chemical admix mismatches. pH measurements may be used in estimating concrete setting behavior, placeability, and pumpability performance.

Micro fiber composite (MFC) sensor 1140 measures a cumulative deformational voltage. MFC sensor 1140 may include a piezoelectric substance that generates a voltage when strained, for example. As MFC sensor 1140 is deformed, a voltage is generated indicating the degree of deformation. This voltage information may be used to determine a degree of concrete agitation, a measure of viscous drag forces experienced by sensing 1100, for example. Such information may be used to determine characteristics of the concrete mixture, for example, estimates of mixing energy, slump, etc. Such information may be used in conjunction with data obtained by accelerometer 1150 to determine characteristics of the concrete mixture such as slump, mixing energy, etc.

MFC sensor 1140 may be calibrated for concrete based on, for example, measurements in water.

Accelerometer 1150 obtains data relating to the motion of sensing device 1100. For example, accelerometer 1150 may measure a degree of acceleration due to mixing of concrete in a truck, transport of the concrete, and placement of the concrete. Accelerometer 1150 may measure non-steady motion, a degree of fluid drag resisting motion as compared to water, etc. Data from accelerometer 1150 may be used to determine a measure of slump, flowability, etc. For example, in a spinning tank containing concrete having a high water content, accelerometer 1150 may indicate a relatively low drag; in a spinning tank containing concrete having a low water content, accelerometer 1150 may indicate a high drag.

Elevation sensor 1160 detects the elevation of sensing device 1100. For example, this may allow an operator to determine where the sensing device is located in a structure after the concrete has been poured. In some embodiments, a large number of sensing devices may be distributed throughout the poured concrete and, consequently, sensing devices may be distributed throughout different locations and different levels of the structure being constructed. An operator may continue to receive data from each of the sensing devices and use the data to monitor the drying and performance of the concrete.

RFID device 1170 transmits a signal containing one or more identifiers. The identifier may be associated with a batch, a mixture, a structure, a project, etc. The identifier may include a pod serial number, for example. The identifier may be used to link data generated by the sensing device during manufacturing, transportation, placement, and data generated while in the structure to a specific batch, mixture, project, etc. As a result, each sensing device may have access to other data already obtained and stored in a closed-loop system database, such as batched performance specifications such as slump, strength, batched materials contents such as water, cementitious, water/cm ratio, expected strength at point of delivery if lab cured at 20 dC, etc.

In one embodiment, sensing device 1100 transmits location coordinates and its RFID serial number or identifier. Each sensing device has a unique RFID serial number/identifier. When a sensing device is inserted into a concrete mixture, a batch ticket associated with the concrete batch is linked in a one-to-one relationship to the RFID serial number.

Battery 1180 may be any suitable battery or other type of power device. Battery 1180 may be a watch-type battery, for example.

Humidity sensor 1190 measures the humidity of a concrete mixture. Humidity sensor 1190 may measure concrete pore humidity, for example. In many instances, concrete needs close to 100% humidity to cure and develop strength. When humidity drops below 80% concrete curing and hydration may cease. In-place concrete strength may be modeled by delivering probable strength as a baseline, analyzing historical humidity and temperature measurements from sensing device 1100, etc. Delivered probable strength as a baseline may be corrected for on-location water additions using conductivity measurements.

GPS based geolocation sensor 1195 uses GPS measurements to detect the location of sensing device 1100. Location measurements may be used to determine where the sensing device is located and thus be used to determine where concrete-related activities such as transportation, pouring, etc., occur.

Antenna 1197 transmits data, and may receive data. Antenna 1197 may be Bluetooth and/or Wi Fi capable. Antenna 1197 may be integrated with GPS sensor 1195.

Figure 12:
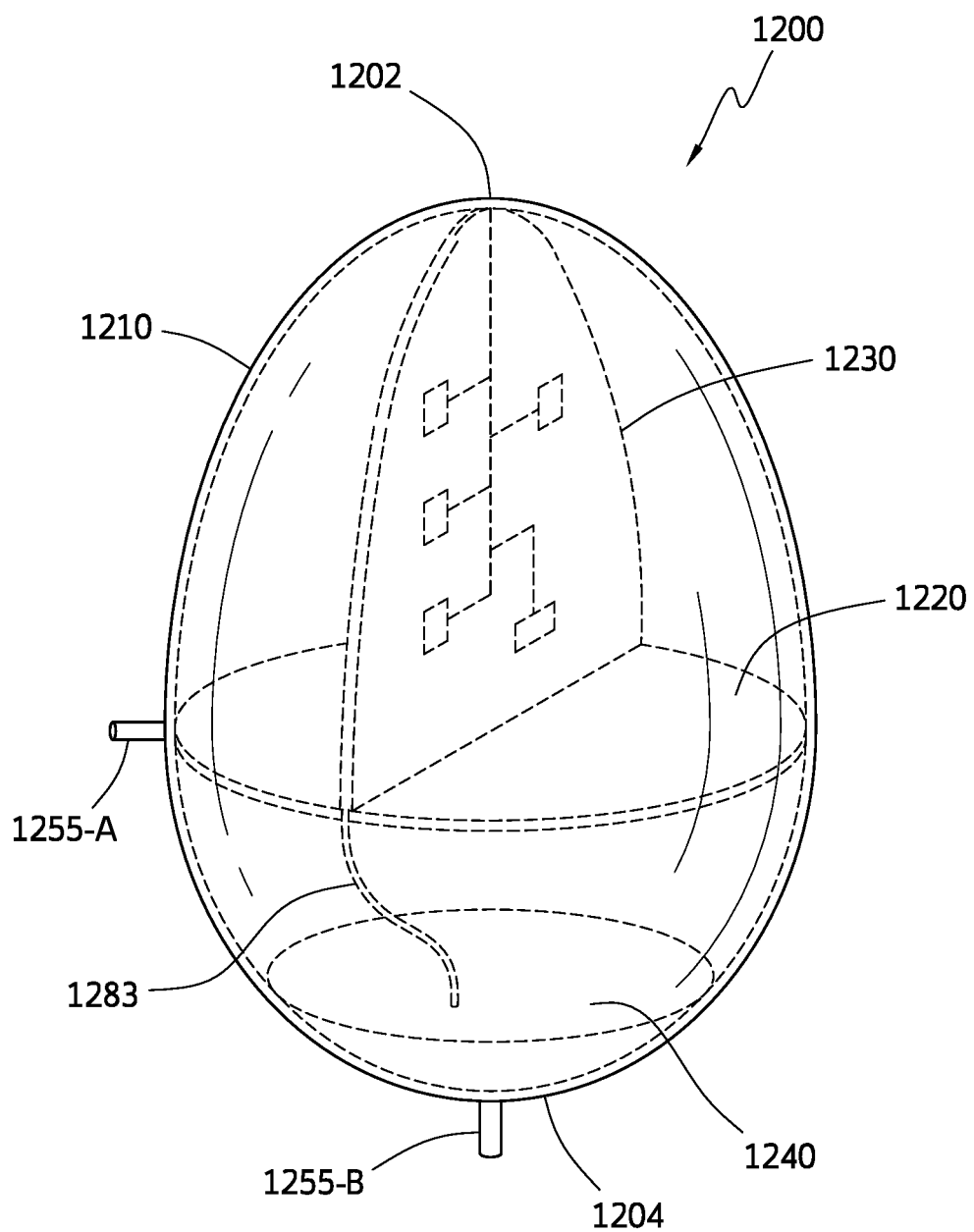
FIG. 12 shows a sensing device in accordance with an embodiment.

FIG. 12 shows a sensing device 1200 in accordance with an embodiment. Sensing device 1200 includes a shell 1210. Shell 1210 has an egg shape and includes a narrower end 1202 and a flatter end 1204. In other embodiments, shell 1210 may have a different shape. Shell 1210 is made of an elastomeric material such as silicone rubber, neoprene, a thermoplastic elastomer, or a similar material. Shell 1210 may be approximately 2-3 mm thick, for example, and have an aspect ratio between about 1.4 to 2.0, for example. The diameter of shell 1210 may be between about 0.10 inch and 2.0 inch, for example. The height of shell 1210 may be between about 0.25 inch and 3.0 inches, for example.

Sensing device 1200 has a low center of gravity. Sensing device 1200 has an effective specific gravity between about 0.9 to 1.5.

Sensing device 1200 may be pressurized with nitrogen gas at about 2-3 atmospheres.

Sensing device 1200 includes a disc 1220, which provides structure. Disc 1220 may function as a thermally and electrically conducting disc. Disc 1220 may therefore function as a temperature measuring disc. Disc 1220 is a circular disc disposed perpendicular to the axis of the sensing device (the axis being defined as the line between the narrower end 1202 and the flatter end 1204).

Sensing device 1200 also includes a metallic and electrically conducting substance 1240 at the flatter end 1204 to provide a weight at the flatter end 1204; the additional weight causes sensing device 1200 to float with an orientation such that the narrower end 1202 remains above the water-line or fluid-line while the flatter end 1204 remains submerged. Substance 1240 may be embedded in the inside surface of shell 1210 at the flatter end 1204, or otherwise attached to the inside surface of shell 1210 at flatter end 1204. Substance 1240 may include a predetermined amount of a metallic and conducting substance, for example. Substance 1240 may be copper or brass, for example. The end of sensing device 1200 with flatter end 1204 is heavier than the end of sensing device 1200 with narrower end 1020. Substance 1240 weighs down the flatter end 1204 for controlled buoyancy.

Due to the structure of sensing device 1200, and substance 1240 in particular, sensing device 1200 is buoyant and floats in liquid or fluid (such as fluid concrete) with flatter end 1204 submerged and narrower end 1202 remaining above the liquid/fluid. Narrower end 1202 remains "above water" while flatter end 1204 remains submerged.

Sensing device 1200 includes a first electrode 1255-A and a second electrode 1255-B. Electrode 1255-A includes a conductive material fitted through a hole in the side of shell 1210. Electrode 1255-A is connected to disc 1220. Second electrode 1255-B includes a conductive material fitted through a hole in shell 1210. Second electrode 1255-B is connected to substance 1240. First and second electrodes 1255-A, 1255-B may be used to obtain pH measurements, impedance measurements, conductivity measurements, measurements of dielectric properties, etc.

A wire 1283 or other conducting connection may connect substance 1240 to disc 1220.

Sensing device 1200 also includes a plate 1230. In the illustrative embodiment, plate 1230 is disposed perpendicular to disc 1220. Plate 1230 may include circuitry/electronics. Plate 1230 may include an integrated chip set, for example. Accordingly, plate 1230 may include electronics/circuitry to implement antenna 1197, for example and GPS-based location sensor 1195, for example. Plate 1230 may also include circuitry/electronics implementing all or a portion of one or more of the following components: temperature sensor 1110, impedance/conductivity sensor 1120, pH sensor 1130, micro fiber composite (MFC) sensor 1140, accelerometer 1150, elevation sensor 1160, radio frequency identification (RFID) device 1170, humidity sensor 1190, salinity sensor, etc. In one embodiment, a salinity sensor may include a chloride ion electrode, for example.

In some embodiments, plate 1230 may be plugged into disc 1220 to facilitate manufacturing of sensing device 1200.

Figure 14A:
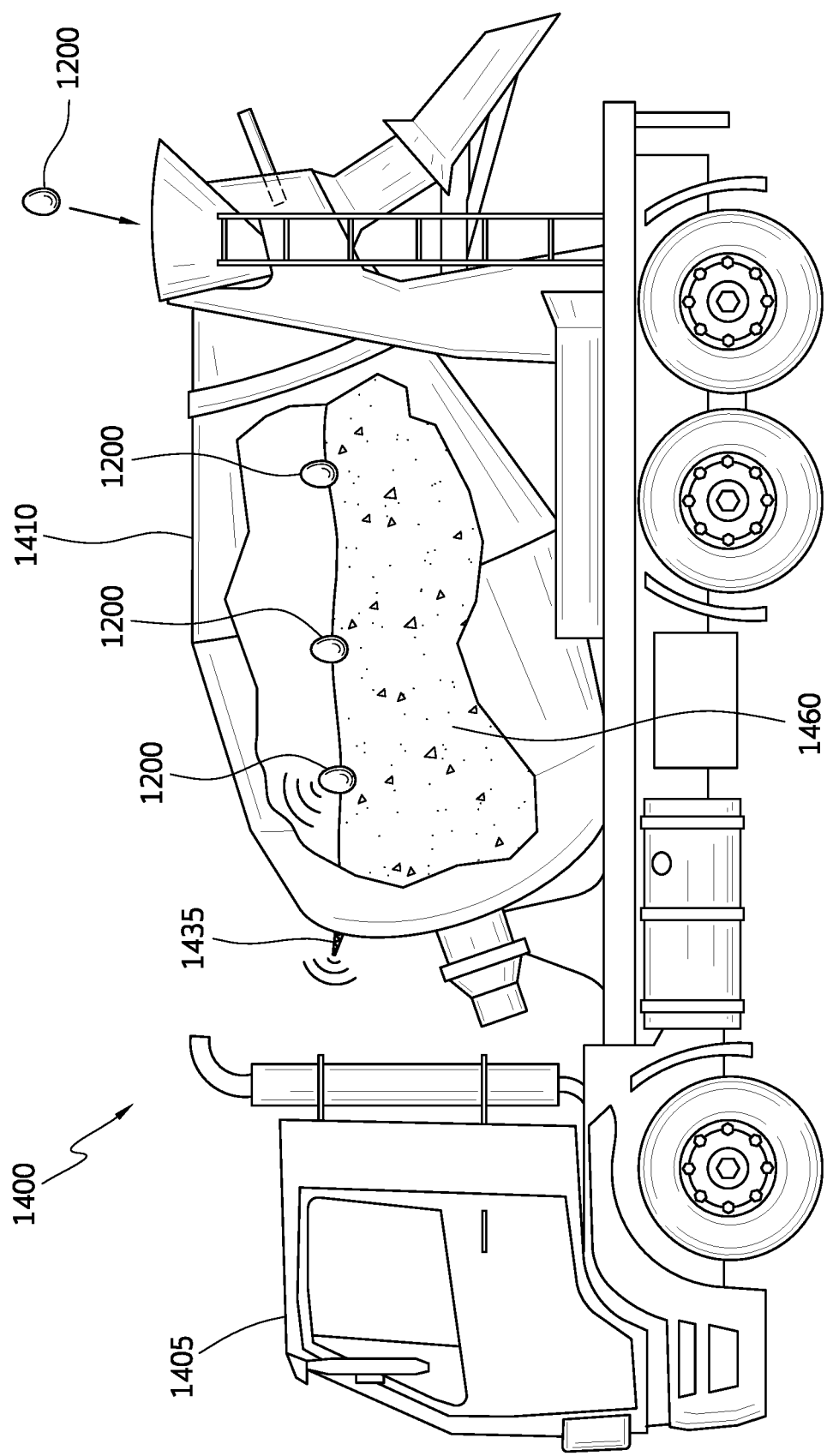
FIG. 14A shows a plurality of sensing devices disposed in a concrete mixture while the mixture is in a drum of a mixing truck in accordance with an embodiment.

One or more sensing devices such as sensing device 1100 or 1200 may be added to a concrete mixture at various stages of a manufacturing and delivery system. Referring to FIG. 13, in one embodiment, for example, one or more sensing devices 1200 may be added to a concrete mixture 1320 while the mixture is in a bin 1310 at a concrete production facility. Referring to FIG. 14A, in another embodiment, one or more sensing devices 1200 may be added to a concrete mixture 1460 while the mixture is in a drum 1410 of a concrete mixing truck 1400. In this illustrative example, an antenna 1435 is located on drum 1410. Antenna 1435 may include a Bluetooth antenna, for example. Antenna 1435 may receive signals from sensing devices 1200 which are disposed in the mixture 1460 within drum 1410.

Signals from antenna 1435 may be transmitted to a processing device (not shown) in the cab of truck 1400. For example, the driver of the truck may operate a laptop computer that receives the data from antenna 1435 and transmits it via the Internet (e.g., to master database module 1611 shown in FIG. 16).

Figure 14B:
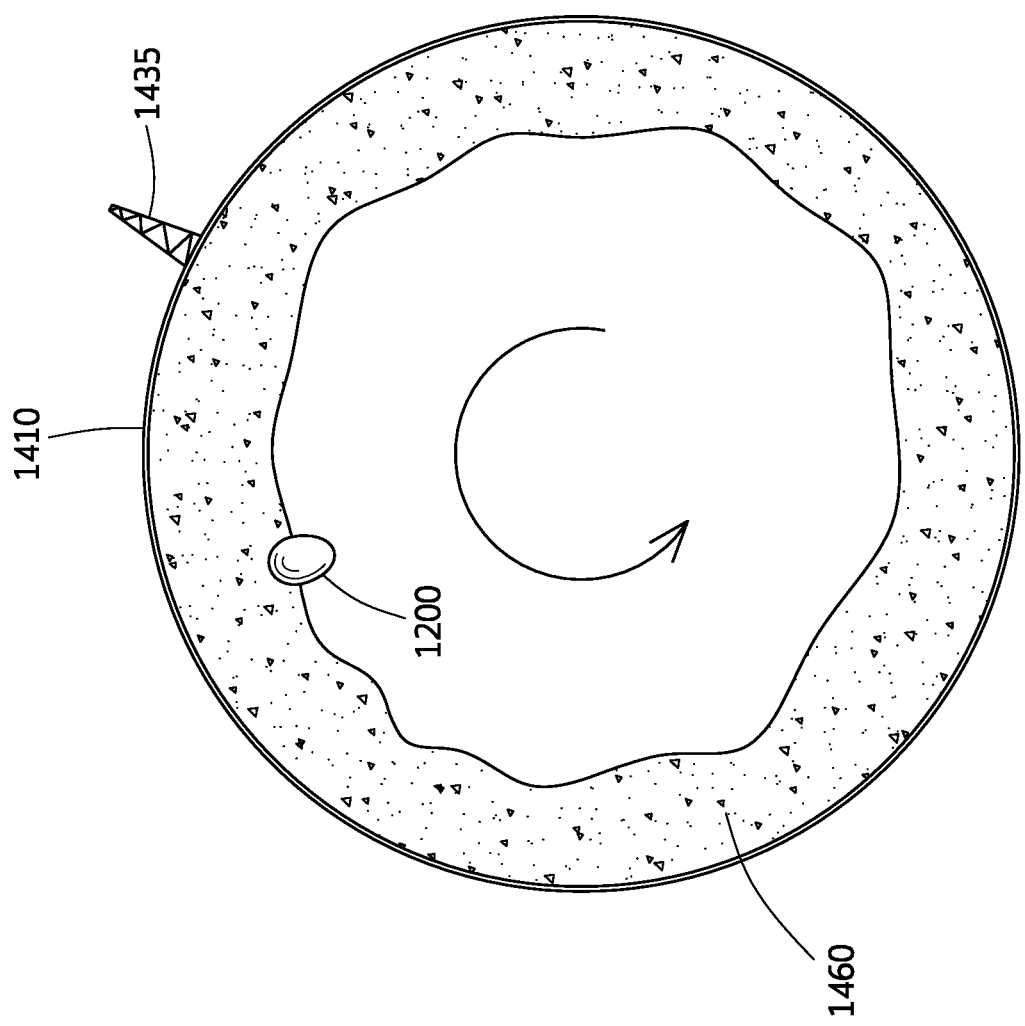
FIG. 14B shows a plurality of sensing devices disposed in a concrete mixture while the mixture is in a drum of a mixing truck in accordance with an embodiment.

FIG. 14B shows a view along an axis of drum 1410 as the drum spins. Concrete mixture 1460 spins within drum 1410. Sensing device(s) 1200 float within the concrete mixture. Sensing device(s) 1200 may spin around the inside of drum 1410 within the concrete due to centripetal and other forces. The narrow end of each sensing device 1200 remains above the fluid level of the concrete. Sensing device 1200 may transmit data from time to time; such data is received by antenna 1435 (which is located on drum 1410).

Figure 15:
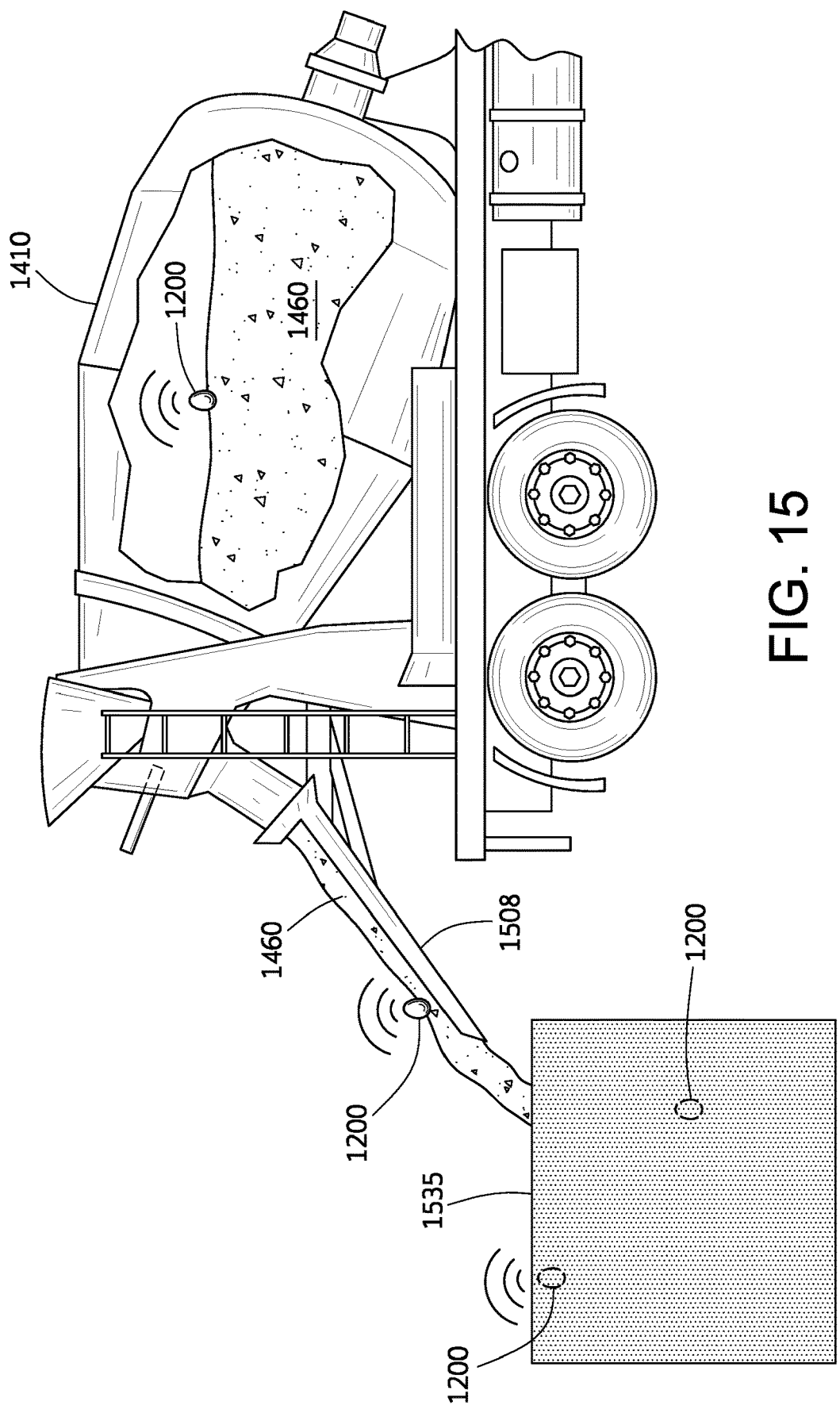
FIG. 15 shows a construction site in accordance with an embodiment.

FIG. 15 shows a construction site in accordance with an embodiment. The concrete mixture 1460 is poured along a chute 1508 from inside the drum 1410 of the truck. Concrete mixture 1460 is poured into a form to create a structure 1535. Sensing devices 1200 flow with the concrete mixture from the drum 1410 down along chute 1508 and into structure 1535. Sensing devices 1200 continue to transmit data from inside drum 1410, transmit data as the devices travel along chute 1508, and transmit data after placement within structure 1535. After the concrete mixture sets to form structure 1535, sensing devices 1200 (disposed at different levels within the structure) continue to transmit data. The data may be received by a receiving device at the site, for example, and/or transmitted via the Internet or via a cellular network.

In other embodiments, one or more sensing devices may be added to a concrete mixture at other stages in the production, transport, and delivery process. For example, workers at a construction site may place a sensing device into a concrete mixture after the mixture has been laid at the site. Workers may drop a sensing device into the chute containing concrete as the concrete is being poured from the truck. Sensing devices may be added at other stages not discussed herein. A sensing device such as sensing device 1100 or 1200 may be added to dry components of concrete or to fluid concrete.

Figure 16:
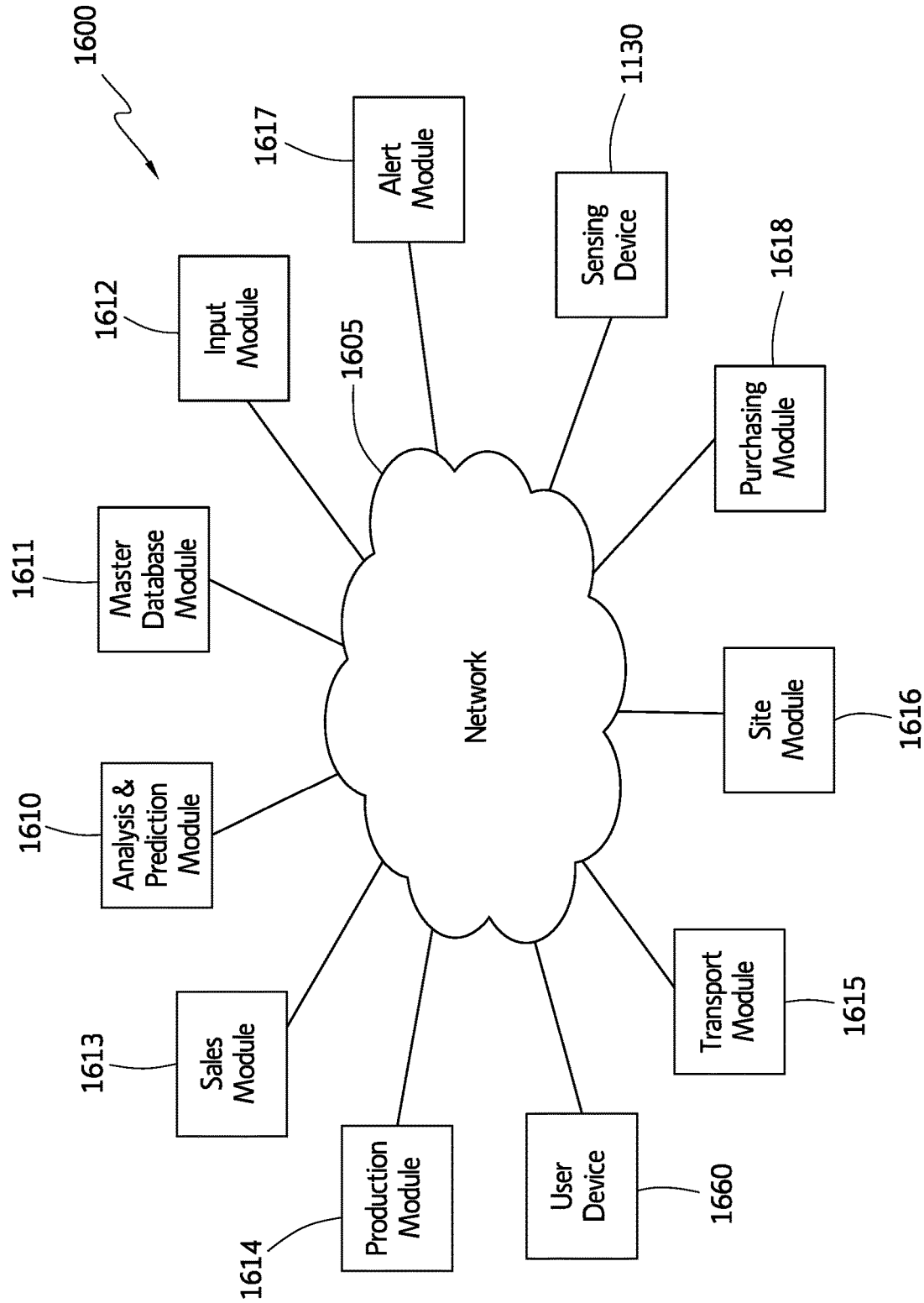
FIG. 16 shows a closed-loop production system in accordance with an embodiment.

In another embodiment, sensing devices such as sensing device 1100 or 1200 may function within a closed-loop production and delivery system. FIG. 16 shows a closed-loop production system in accordance with an embodiment. Product management system 1600 includes a master database module 1611, an input module 1612, a sales module 1613, a production module 1614, a transport module 1615, a site module 1616, an alert module 1617 and a purchasing module 1618. Production management system 1600 also includes a sensing device 1130, which may be similar to sensing device 1100 illustrated in FIG. 11 or sensing device 1200 illustrated in FIG. 12. Production management system 1600 also includes an analysis & prediction module 1610.

System 1600 may include more than one sensing device 1130. Sensing device(s) 1130 transmit data representing various measurements obtained by sensors, such measurements obtained by various sensors illustrated in FIG. 11, to master database module 1611 via a network 1605.

Production management system 1600 also includes a user device 1660, which may be a processing device such as a laptop computer, a cell phone, a personal computer, etc., employed by a user to communicate with production management system 1600.

Master database module 1611 may be implemented using a server computer equipped with a processor, a memory and/or storage, a screen and a keyboard, for example.

Modules 1610-1618 may be implemented by suitable computers or other processing devices with screens for displaying and keep displaying data and keyboards for inputting data to the module.

Master database module 1611 maintains one or more product formulations associated with respective products. In the illustrative embodiment, formulations are stored in a database; however, in other embodiments, formulations may be stored in another type of data structure. Master database module 1611 also stores other data related to various aspects of production management system 1600. For example, master database module 1611 may store information concerning acceptable tolerances for various components, mixtures, production processes, etc., that may be used in system 1610 to produce various products. Stored tolerance information may include tolerances regarding technical/physical aspects of components and processes, and may also include tolerances related to costs. Master database module 1611 may also store cost data for various components and processes that may be used in system 1600.

Each module 1610-1618, as well as sensing device 1130 and user device 1660, transmit data to, and may receive data from, master database module 1611 via network 1605, which may include the Internet and/or other types of networks such as a wireless network, a wide area network, a local area network, an Ethernet network, etc.

Master database module 1611 stores data inputted from modules 1610-1618, sensing device 1130, and user device 1660. Master database module 1611 stores data in a memory or storage using a suitable data structure such as a database. In other embodiments, other data structures may be used. In some embodiments, master database module 1611 may store data remotely, for example, in a cloud-based storage network.

Analysis & prediction module 1610 analyzes data stored in master database module 1611 and generates calculations and predictions based on such information. For example, analysis & prediction module 1610 may analyze certain measurements stored in master database module 1611, such as measurements of a concrete mixture's conductivity, temperature, humidity, motion, location, elevation, etc., and generate a value of or prediction of a characteristic of a concrete mixture, such as the concrete mixture's strength, setting behavior, slump, age, maturity, etc.

Input module 1612 transmits to master database module 1611 data for storage in the form of mixture formulations associated with respective mixtures, procedures for making the mixtures, individual ingredients or components used to make the mixture, specifics about the components, the theoretical costs for each component, the costs associated with mixing the components so as to make the product or mixture, the theoretical characteristics of the product, acceptable tolerances for variations in the components used to make the product, the time for making and delivering the product to the site and costs associated shipping the product.

Sales module 1613, production module 1614, transport module 1615, and site module 1616 communicate various items of information relating to orders received from customers for specified concrete mixtures, schedules for production of the mixtures, completion of production, transport of the mixtures from production facilities to delivery sites, delivery of concrete mixtures to specified sites, use of mixtures in construction at sites, etc. Such information is stored at master database module 1611. Alert module 1617 transmits alerts to master database module 1611, to customers, and/or to others.

Production management system 1600 also includes sensing device(s) 1130. Sensing device(s) 1130 may be added to a concrete mixture at any stage of production, transport or delivery. Sensing device 1130 generates and transmits data relating to various characteristics of the concrete mixture, measurements of the environment, etc. These measurements are received by and stored at master database module 1611.

The terms "product" and "mixture" are used interchangeably herein.

Data transmitted by input module 1612 to master database module 1611 and stored in master database module 1611 may be historical in nature. Such historical data may be used by the sales personnel through sales module 1613 to make sales of a product.

In one embodiment, sales module 1613 receives product data from master database module 1611 relating to various products or mixtures that are managed by system 1600, the components that make up those products/mixtures, the theoretical costs associates with the components, making the mixture and delivery of the mixture, times for delivery of the mixture and theoretical characteristics and performance specifications of the product.

Figure 17:
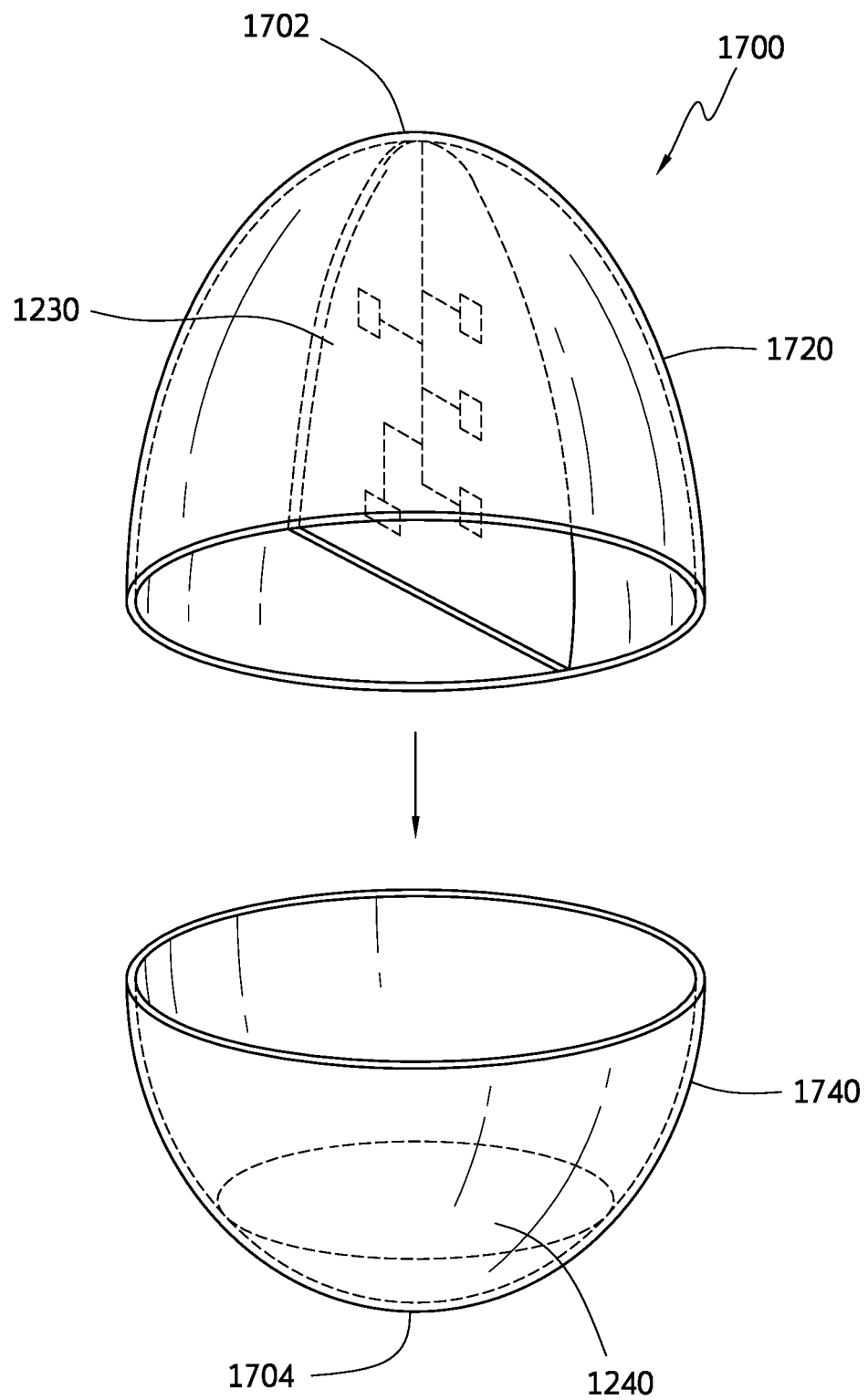
FIG. 17 shows a sensing device made of a first portion and a second portion.

In one embodiment, a sensing device similar to sensing device 1100 or 1200 may have two portions. Referring to FIG. 17, sensing device 1700 includes a first portion 1720 of the shell associated with a narrower end 1702, and a second portion 1740 of the shell associated with a flatter end 1704. The two portions of the shell may be manufactured, the plate 1230 and electronics inserted into first portion 1720, and substance 1240 inserted into second portion 1740. Electrode 1255-A is inserted in first portion 1720; electrode 1255-B is inserted in second portion 1740. The two portions 1720 and 1740 may then be joined and sealed to create a sensing device. In some embodiments, pressurized nitrogen gas may be injected into the sensing device.

In the illustrative embodiment, second portion 1740 is heavier than first portion 1720; as a result, when placed in a liquid or fluid, sensing device 1700 floats with flatter end 1704 submerged and narrower end 1702 remaining above the fluid level. In one embodiment, the second portion of the shell 1740 (having the flatter end 1704) is heavier than the first portion 1720 (having the narrower end 1702).

In other embodiments, both electrodes may be disposed in first portion 1720, or in second portion 1740.

In another embodiment, a sensing device such as sensing device 1100 or 1200 may be manufactured using three-dimensional printing technology. For example, two portions of the shell may be designed to have two portions—an upper portion associated with narrow end 1202 and a lower portion associated with flatter end 1204. Each portion may be mathematically modeled and the mathematical model then provided to a 3D printing device for production. For example, the upper portion may be mathematically defined based on an ellipsoid curve. The lower portion may be defined based on an ellipsoid curve (different from the ellipsoid curve used for the upper portion), or defined based on a circle. Other curves, or other types of mathematical formulations may be used.

In another embodiment, a production system such as that shown in FIG. 16 may maintain and offer to customers a formulation for a concrete mixture that includes several components for manufacturing concrete. The formulation may also specify a desired quantity of (i.e., one or more) sensing devices as an optional component. The formulation may also specify a stage of the manufacturing cycle (e.g., at the production plant, when the mixture is in the truck, at the construction site, etc.) at which the sensing devices are to be inserted into the mixture. If the customer orders a formulation that includes a predetermined number of sensing devices, then the concrete mixture is manufactured according to the formulation, and the predetermined number of sensing devices are added to the mixture at the specified stage in the manufacturing process (e.g., at the production facility, inserted into the mixing truck, added at the construction site, etc.)

Figure 18:
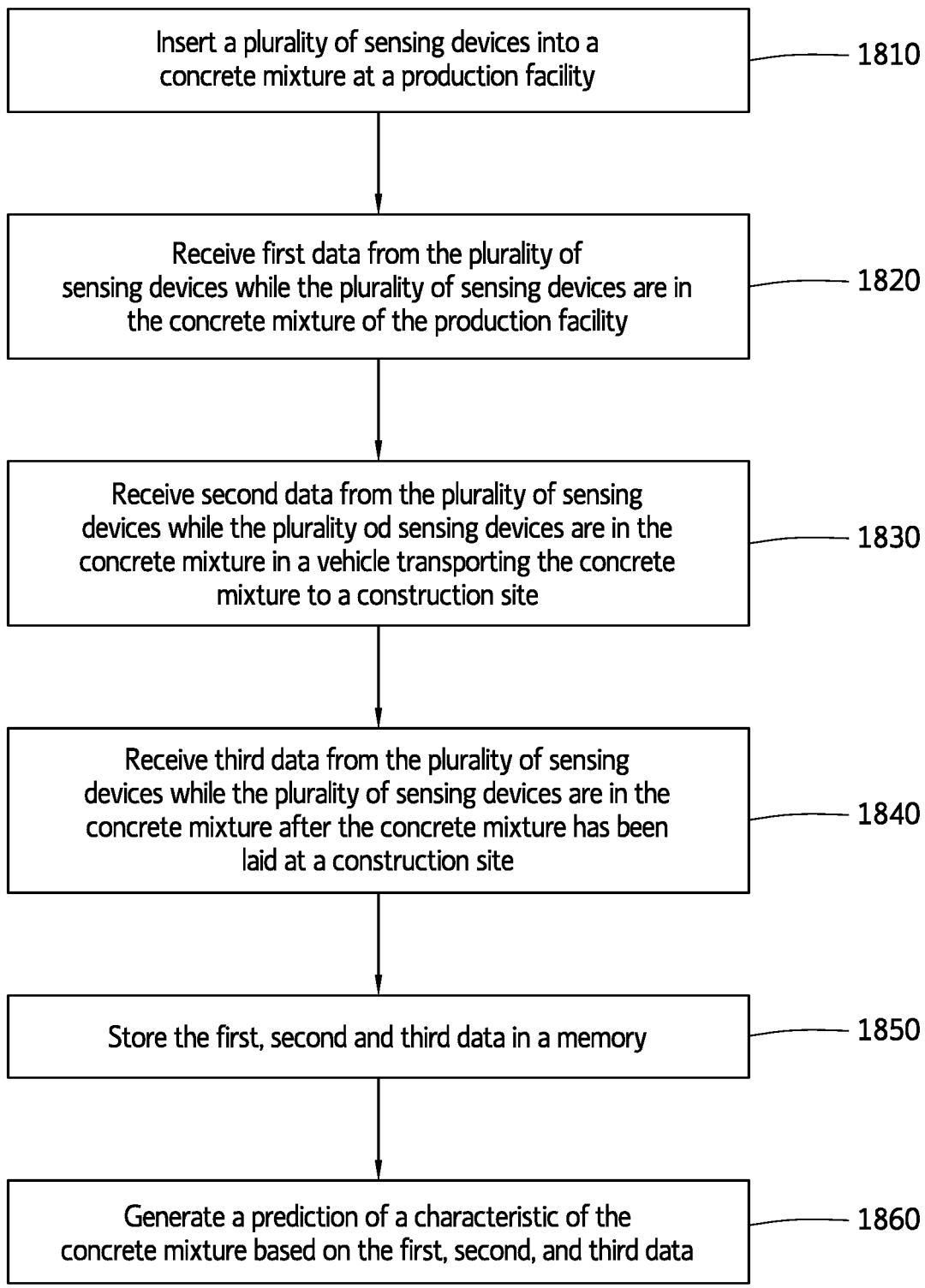
FIG. 18 is a flowchart of a method of managing a closed-loop production system in accordance with an embodiment.

FIG. 18 is a flowchart of a method of managing a closed-loop production system in accordance with an embodiment. At step 1810, a plurality of sensing devices are inserted into a concrete mixture at a production facility. Thus, as illustrated in FIG. 13, for example, a plurality of sensing devices 1200 are inserted into a concrete mixture at a production facility. In some embodiments, one or more sensing devices may be added to a dry mixture at the production facility. In other embodiments, sensing devices may be added to a wet mixture at the production facility.

At step 1820, first data is received from the plurality of sensing devices while the plurality of sensing devices are in the concrete mixture at the production facility. Sensing devices 1200 may begin to obtain measurements and transmit data immediately upon being inserted into the mixture. The data may be received by wireless receivers (not shown in FIG. 13) and transmitted to master database module 1611. At step 1830, second data is received from the plurality of sensing devices while the plurality of sensing devices are in the concrete mixture in a vehicle transporting the concrete mixture to a construction site. As illustrated in FIG. 14B, sensing devices 1200 may continue to transmit data while floating in the concrete mixture inside the drum of a mixing truck. The data is received by antenna 1435, which in turn may transmit it to master database module 1611 (or to another device in the truck which transmits it to master database module 1611.) At step 1840, third data is received from the plurality of sensing devices while the plurality of sensing devices are in the concrete mixture after the concrete mixture has been laid at a construction site. As illustrated in FIG. 15, sensing devices 1200 remain in concrete mixture 1460 while the concrete is poured at a construction site. After the concrete has been laid to form a structure 1535, sensing devices 1200 remain in the concrete and continue to transmit data. The data received from sensing devices is received by master database module 1611. At step 1850, the first, second and third data are stored in a memory. Master database module 1611 stores he data received from sensing devices at different stages of the production cycle in a memory, for example, in a database or other data structure.

At step 1860, a prediction of a characteristic of the concrete mixture is generated based on the first, second and third data. For example, analysis & prediction module 1610 may access the data generated by sensing devices 1200 and generate predictions concerning the strength, maturity, age, slump, etc., of the concrete mixture, or predictions of other characteristics. The predictions may be provided to master database module 1611 and stored, for example.

In accordance with another embodiment, data received from a plurality of sensing devices distributed throughout concrete in a building or other structure being built at a construction site as part of a project may be used to provide real-time data concerning the project. Suppose, for example, that a plurality of sensing devices are embedded in the concrete laid at different floors or levels of a building. After the concrete sets, data received from the sensing devices throughout the structure may continue to provide data concerning performance of the concrete in the structure. Such data may then be used as a basis for determining various items of information such as the strength of the concrete used in different sections of the structure, the cost of materials in different sections of the structure, the pour rate for concrete in different sections of the structure, and the pour rate cost per hour for different sections of the structure, and/or other characteristics. The data from the sensing devices may be combined with other data to generate some or all of such information. Master database module 1611 may then allow a user employing user device 1660 to access the information.

Figure 19:
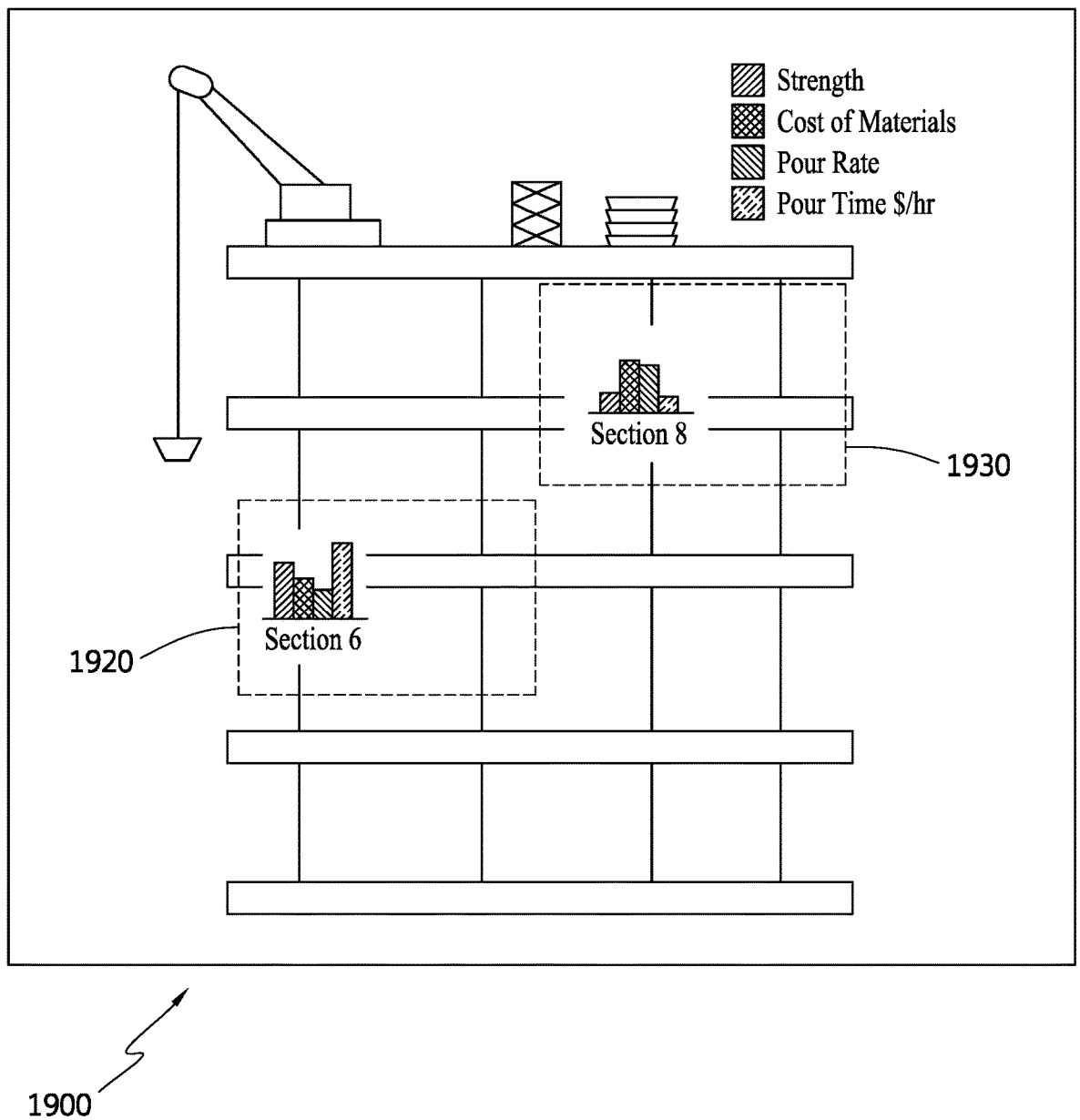
FIG. 19 shows a web page showing information related to a construction site in accordance with an embodiment.

For example, master database module 1611 may generate a web page such as that shown in FIG. 19. Web page 1900 shows a construction site that includes a building under construction. Several sections of building are defined. A user may select (by clicking on a section of the image, for example) a desired section of the structure to obtain information relating to the section. In the illustrative embodiment, the user has selected a Section 6 (1920) and a Section 8 (1930) of the structure. When the user selects a section of the structure, master database module 1611 causes a bar graph representing selected items of information relevant to the selected section to appear over the selected section in the image. In this example, a bar graph indicating strength, cost of materials, pour rate, and pour time cost per hour is displayed over the respective section. Other types of information may be displayed.

Figure 20:
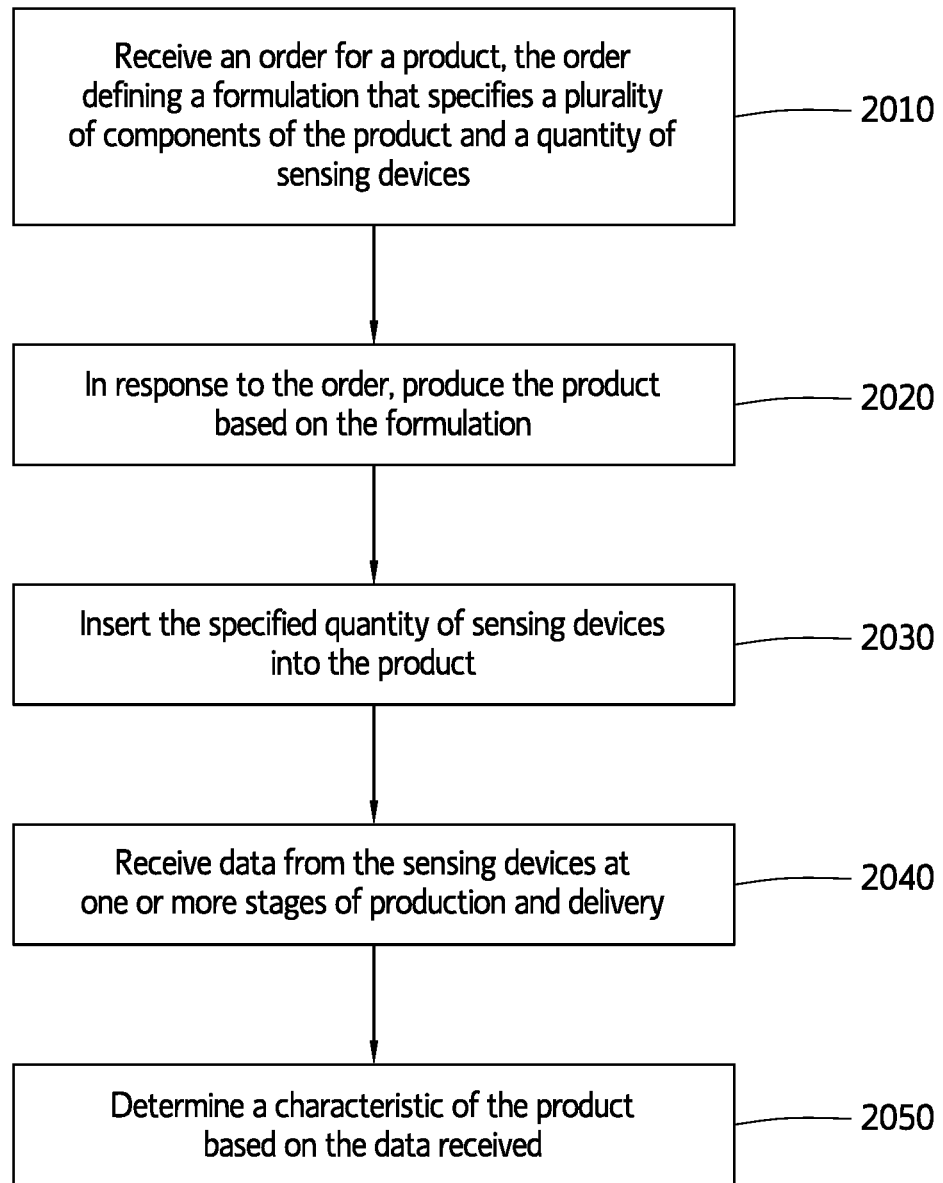
FIG. 20 shows a flowchart of a method of managing a production management system in accordance with an embodiment.

FIG. 20 is a flowchart of a method of managing a production management system in accordance with another embodiment. At step 2010, an order for a product is received, wherein the order defines a formulation that specifies a plurality of components of the product and a quantity of sensing devices. Thus, a customer may submit an order for a concrete mixture having desired components. The customer may also specify in the order a desired quantity of sensing devices to be inserted into the mixture. The order may be transmitted by sales module 1613 to master database module 1611, for example. At step 2020, in response to the order, the product is produced based on the formulation at a production facility. For example, master database module 1611 may transmit the order to a selected production facility, which receives the order and produces the product. At step 2030, the specified quantity of sensing devices are inserted into the product. Master database module 1611 may cause the specified quantity of sensing devices to be inserted into the mixture at a specified stage of production/delivery. The order may specify when and where to insert the sensing devices into the mixture. At step 2040, data is received from the sensing devices at one or more stages of production and delivery. As discussed herein, the sensing devices generate one or more measurements, which may be transmitted to master database module 1611. Master database module 1611 receives and stores the data. At step 2050, a characteristic of the product is determined based on the data. Master database module 1611 or another module may generate an estimate of strength, slump, maturity, or another characteristic, based on the data received.

In another embodiment, a sensing device similar to sensing device 1100 may function as a signal booster/retransmitter for signals received from other sensing devices. Such a sensing device may be dedicated to receiving data from other sensing devices located nearby (e.g., within a predetermined distance) and transmitting the data to the outside world (e.g., to a Bluetooth receiver, to a cellular network, etc.). In an illustrative embodiment, a predetermined percentage of sensing devices within a plurality of sensing devices (e.g., one out of five sensing devices, one out of ten sensing devices, etc.) may be adapted and/or programmed to perform a signal booster/retransmitter function. Thus, such a booster/retransmitter sensing device may receive signals from other sensing devices, optionally boost the signals, and retransmit the signals. Because wireless transmission consumes significant power, the stronger the wireless signal (longer distance) is, the more power is required. A sensing device functioning as a signal booster/retransmitter may use all or nearly all of its battery power to transmit signals over significant distances to a Bluetooth receiver or other type of receiver or network. Optionally, other sensing devices may conserve power through short haul transmission to a booster/retransmitter sensing device located within a short distance, e.g., 0.2 to 5 meters. Booster/retransmitter sensing devices may be shaped in a manner to optimize antenna efficiency.

Today a significant amounts of small polymeric and steel fibers are used to reinforce concrete and asphalt against micro cracking, and thereby increase structural longevity for public sector investments. Fibers are typically less than 1.0 mm in diameter and are up to several centimeters in length. In one embodiment, a sensing device such as sensing device 1100 may provide numerous monitoring and structural integrity related benefits to road and bridge surfaces. For example, in order to increase transmission efficiencies, fibers for addition to concrete may be specially embedded in an antenna of a sensing device. Typical steel fiber dosage to concrete is on the order 0.5 to 1 kg/m3, and the count is on the order of 2,000 (macro fiber) to more than 20,000 (micro fiber) per cubic meter. Thus, an antenna of a sensing device that includes a specially configured micro steel fiber at the rate of, e.g., 1 in 100, may result in a many device antennas dispersed through a road or bridge structure. This distribution may significantly increase the wireless transmission efficiencies of the sensing devices.

In various embodiments, the method steps described herein, including the method steps described in FIG. 4, 5, 6, 18 and/or 20 may be performed in an order different from the particular order described or shown. In other embodiments, other steps may be provided, or steps may be eliminated, from the described methods.

Systems, apparatus, and methods described herein may be implemented using digital circuitry, or using one or more computers using well-known computer processors, memory units, storage devices, computer software, and other components. Typically, a computer includes a processor for executing instructions and one or more memories for storing instructions and data. A computer may also include, or be coupled to, one or more mass storage devices, such as one or more magnetic disks, internal hard disks and removable disks, magneto-optical disks, optical disks, etc.

Systems, apparatus, and methods described herein may be implemented using computers operating in a client-server relationship. Typically, in such a system, the client computers are located remotely from the server computer and interact via a network. The client-server relationship may be defined and controlled by computer programs running on the respective client and server computers.

Systems, apparatus, and methods described herein may be used within a network-based cloud computing system. In such a network-based cloud computing system, a server or another processor that is connected to a network communicates with one or more client computers via a network. A client computer may communicate with the server via a network browser application residing and operating on the client computer, for example. A client computer may store data on the server and access the data via the network. A client computer may transmit requests for data, or requests for online services, to the server via the network. The server may perform requested services and provide data to the client computer(s). The server may also transmit data adapted to cause a client computer to perform a specified function, e.g., to perform a calculation, to display specified data on a screen, etc.

Systems, apparatus, and methods described herein may be implemented using a computer program product tangibly embodied in an information carrier, e.g., in a non-transitory machine-readable storage device, for execution by a programmable processor; and the method steps described herein, including one or more of the steps of FIG. 4, 5, 6, 18 and/or 20 may be implemented using one or more computer programs that are executable by such a processor. A computer program is a set of computer program instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

Figure 21:
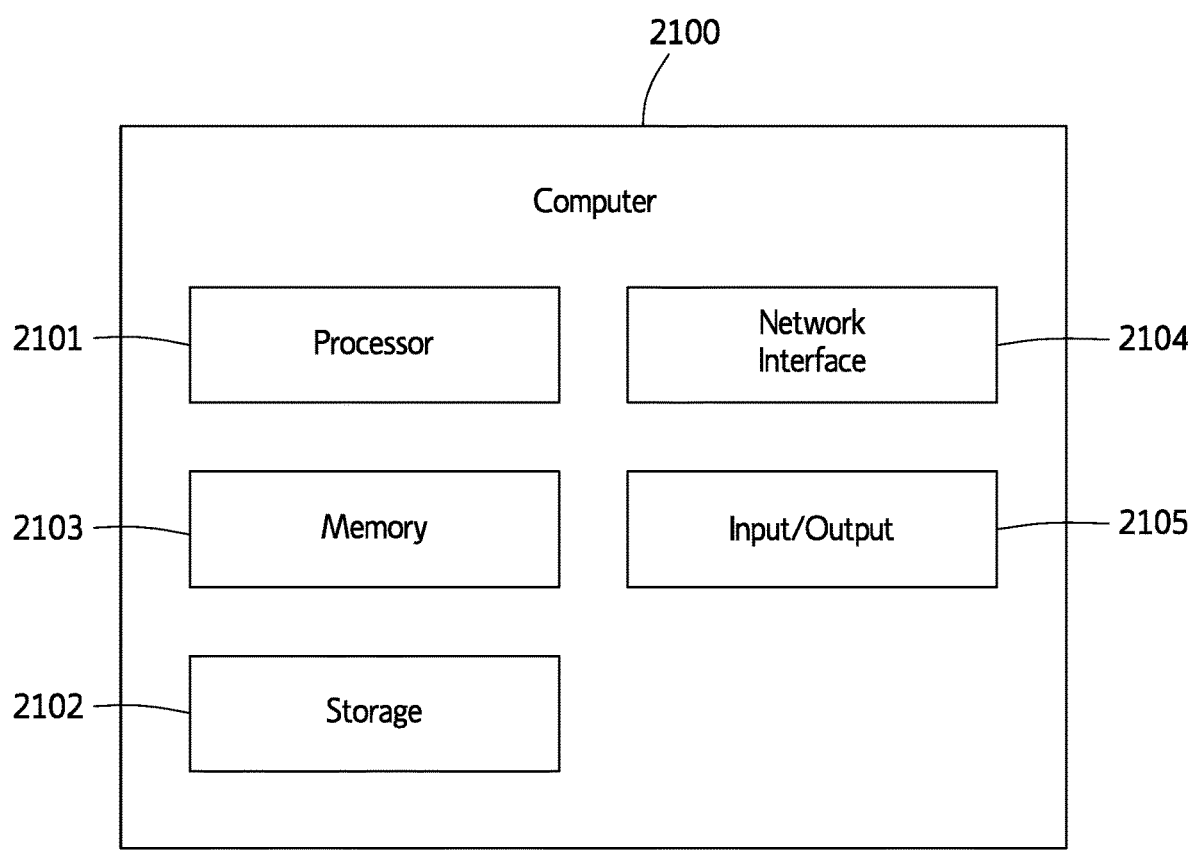
FIG. 21 shows components of an exemplary computer that may be used to implement embodiments of the invention.

A high-level block diagram of an exemplary computer that may be used to implement systems, apparatus and methods described herein is illustrated in FIG. 21. Computer 2100 includes a processor 2101 operatively coupled to a data storage device 2102 and a memory 2103. Processor 2101 controls the overall operation of computer 2100 by executing computer program instructions that define such operations. The computer program instructions may be stored in data storage device 2102, or other computer readable medium, and loaded into memory 2103 when execution of the computer program instructions is desired. Thus, the method steps of FIG. 4, 5, 6, 18 and/or 20 can be defined by the computer program instructions stored in memory 2103 and/or data storage device 2102 and controlled by the processor 2101 executing the computer program instructions. For example, the computer program instructions can be implemented as computer executable code programmed by one skilled in the art to perform an algorithm defined by the method steps of FIG. 4, 5, 6, 18 and/or 20. Accordingly, by executing the computer program instructions, the processor 2101 executes an algorithm defined by the method steps of FIG. 4, 5, 6, 18 and/or 20. Computer 2100 also includes one or more network interfaces 2104 for communicating with other devices via a network. Computer 2100 also includes one or more input/output devices 2105 that enable user interaction with computer 2100 (e.g., display, keyboard, mouse, speakers, buttons, etc.).

Processor 2101 may include both general and special purpose microprocessors, and may be the sole processor or one of multiple processors of computer 2100. Processor 2101 may include one or more central processing units (CPUs), for example. Processor 2101, data storage device 2102, and/or memory 2103 may include, be supplemented by, or incorporated in, one or more application-specific integrated circuits (ASICs) and/or one or more field programmable gate arrays (FPGAs).

Data storage device 2102 and memory 2103 each include a tangible non-transitory computer readable storage medium. Data storage device 2102, and memory 2103, may each include high-speed random access memory, such as dynamic random access memory (DRAM), static random access memory (SRAM), double data rate synchronous dynamic random access memory (DDR RAM), or other random access solid state memory devices, and may include non-volatile memory, such as one or more magnetic disk storage devices such as internal hard disks and removable disks, magneto-optical disk storage devices, optical disk storage devices, flash memory devices, semiconductor memory devices, such as erasable programmable read-only memory (EPROM), electrically erasable programmable read-only memory (EEPROM), compact disc read-only memory (CD-ROM), digital versatile disc read-only memory (DVD-ROM) disks, or other non-volatile solid state storage devices.

Input/output devices 2105 may include peripherals, such as a printer, scanner, display screen, etc. For example, input/output devices 2105 may include a display device such as a cathode ray tube (CRT) or liquid crystal display (LCD) monitor for displaying information to the user, a keyboard, and a pointing device such as a mouse or a trackball by which the user can provide input to computer 2100.

Any or all of the systems and apparatus discussed herein, including master database module 1611, analysis & prediction module 1610, input module 1612, sales module 1613, production module 1614, transport module 1615, site module 1616, alert module 1617, purchase module 1618, and user device 1660, and components thereof, may be implemented using a computer such as computer 2100.

One skilled in the art will recognize that an implementation of an actual computer or computer system may have other structures and may contain other components as well, and that FIG. 21 is a high level representation of some of the components of such a computer for illustrative purposes.

Figure 22A:
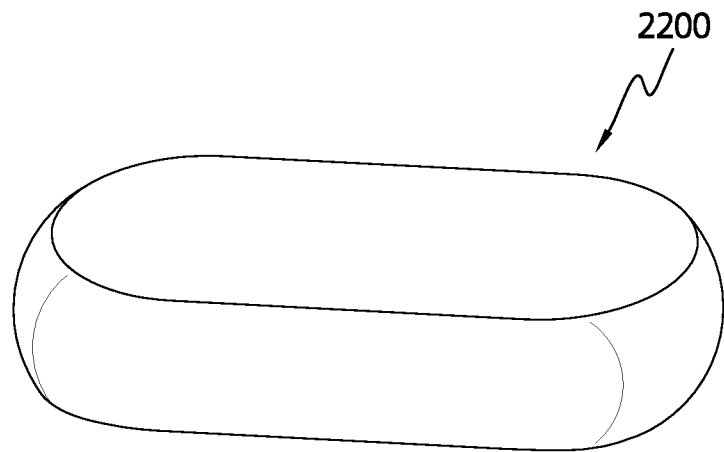
FIGS. 22A-22C show a sensing device in accordance with another embodiment.
Figure 22B:
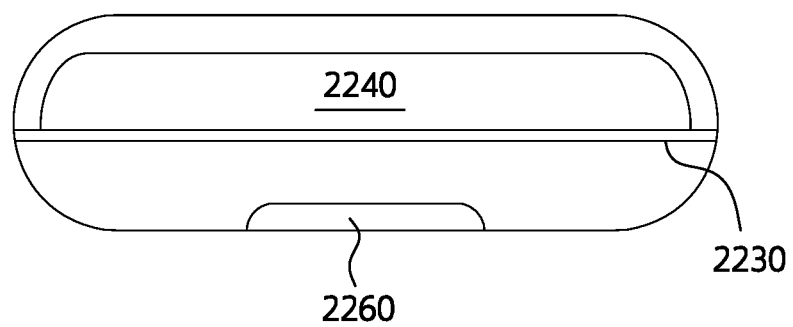
Figure 22C:
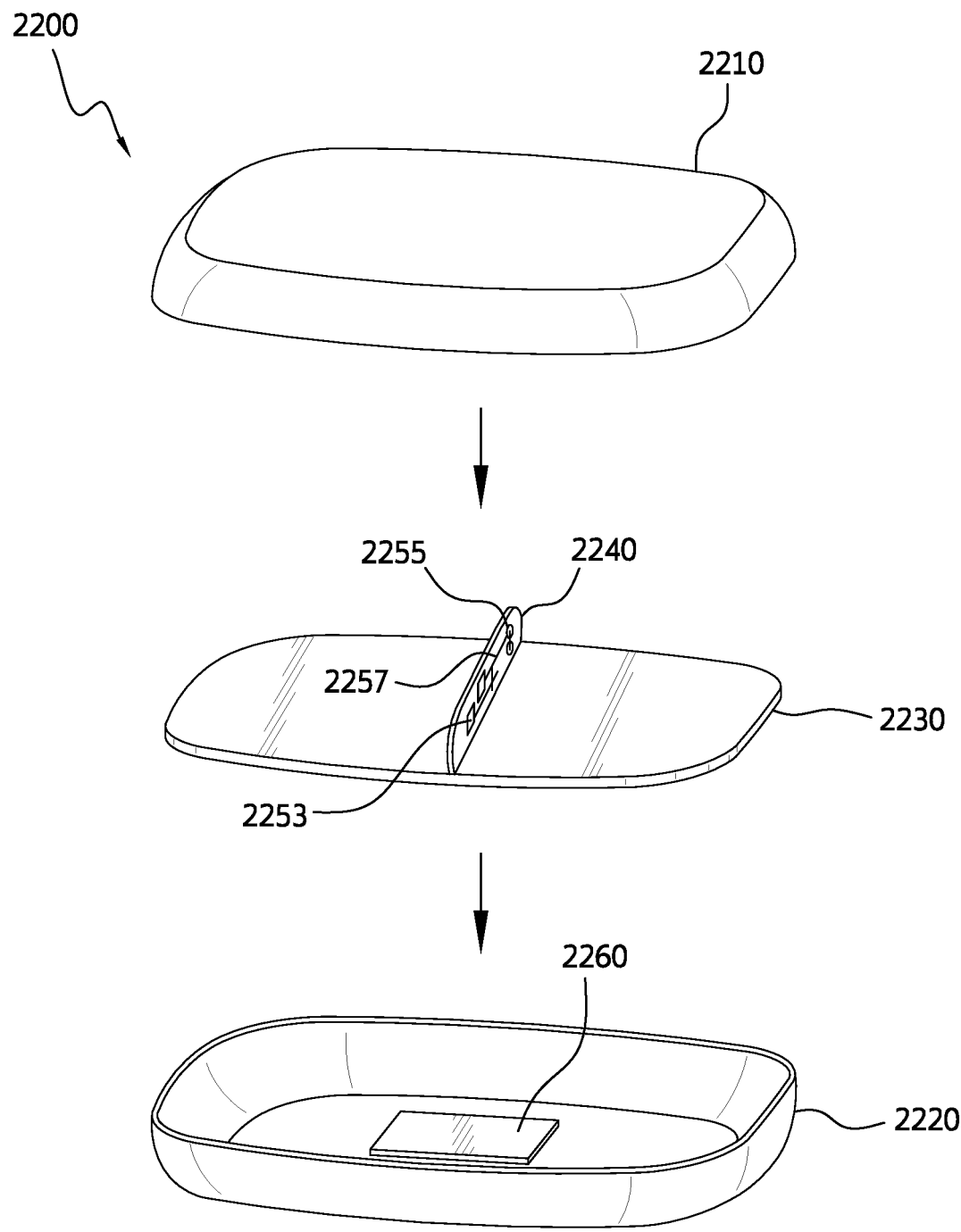

FIGS. 22A-22C show a sensing device 2200 in accordance with another embodiment. FIG. 22A shows a perspective view of sensing device 2200. FIG. 22B shows a cross-section of sensing device 2200. Sensing device 2200 has an oblong shape.

The density of sensing device 2200 is between 1.1 and 1.4. Advantageously, the density of sensing device 2200 is less than the density of concrete (which is typically greater than 2.0). As a result, sensing device 2200 floats in a concrete mixture.

In one embodiment, sensing device has a length of approximately millimeters, a width of approximately millimeters, and a height of approximately 8-15 millimeters.

FIG. 22C shows components of sensing device 2200. Sensing device 2200 includes a first portion 2210 and a second portion 2220 which are joined together. A platform 2230 holds a plate 2240 on which is disposed one or more sensors 2253, an antenna 2255, and associated electronic circuitry 2257.

A quantity of a material 2260, such as a metal, is disposed in a concave inside surface of second portion 2220 to provide a weight. Because of the placement of material 2260, second portion 2220 of sensing device 2200 is heavier than first portion 2210, and sensing device 2200 is accordingly weighted on one side. As a result, when sensing device 2200 is placed in a concrete mixture (or other liquid), sensing device 2200 automatically orients itself with second portion 2200 below first portion 2210. Advantageously, first portion 2210 is oriented toward the surface of the concrete mixture or liquid. Because of the buoyancy of sensing device 2200, sensing device 2200 rises to the surface of the concrete mixture or liquid, and first portion 2210 is at or above the surface. Advantageously, the position of first portion 2210 at or above the surface of the concrete mixture or liquid allows antenna 2255 to transmit signals without interference from the concrete mixture or liquid.

In some embodiments, a sensing device has a cuboid shape. A cuboid is a convex polyhedron bounded by six quadrilateral faces, whose polyhedral graph is the same as that of a cube. For example, each quadrilateral face may be a rectangle or a square. In some embodiments, a sensing device has a three-dimensional shape based on a cuboid; for example, corners may be rounded, intersections between faces may be rounded, etc.

Figure 23A:
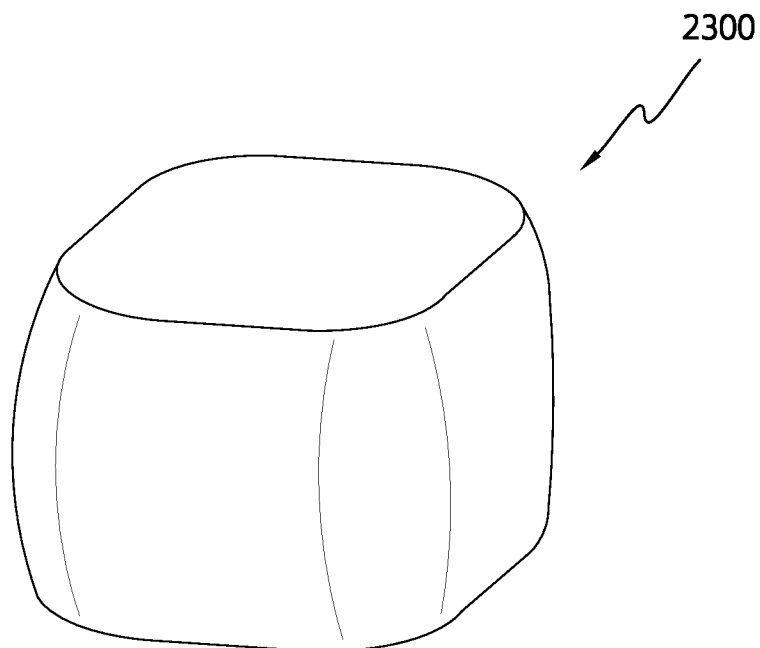
FIGS. 23A-23C show a sensing device in accordance with another embodiment.
Figure 23B:
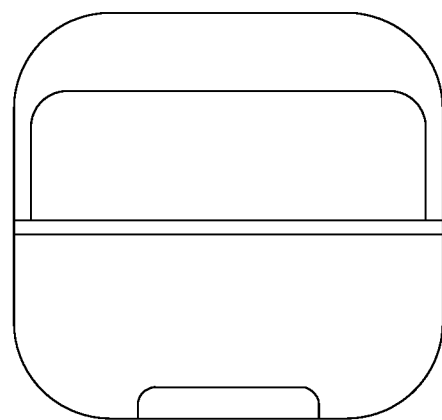
Figure 23C:
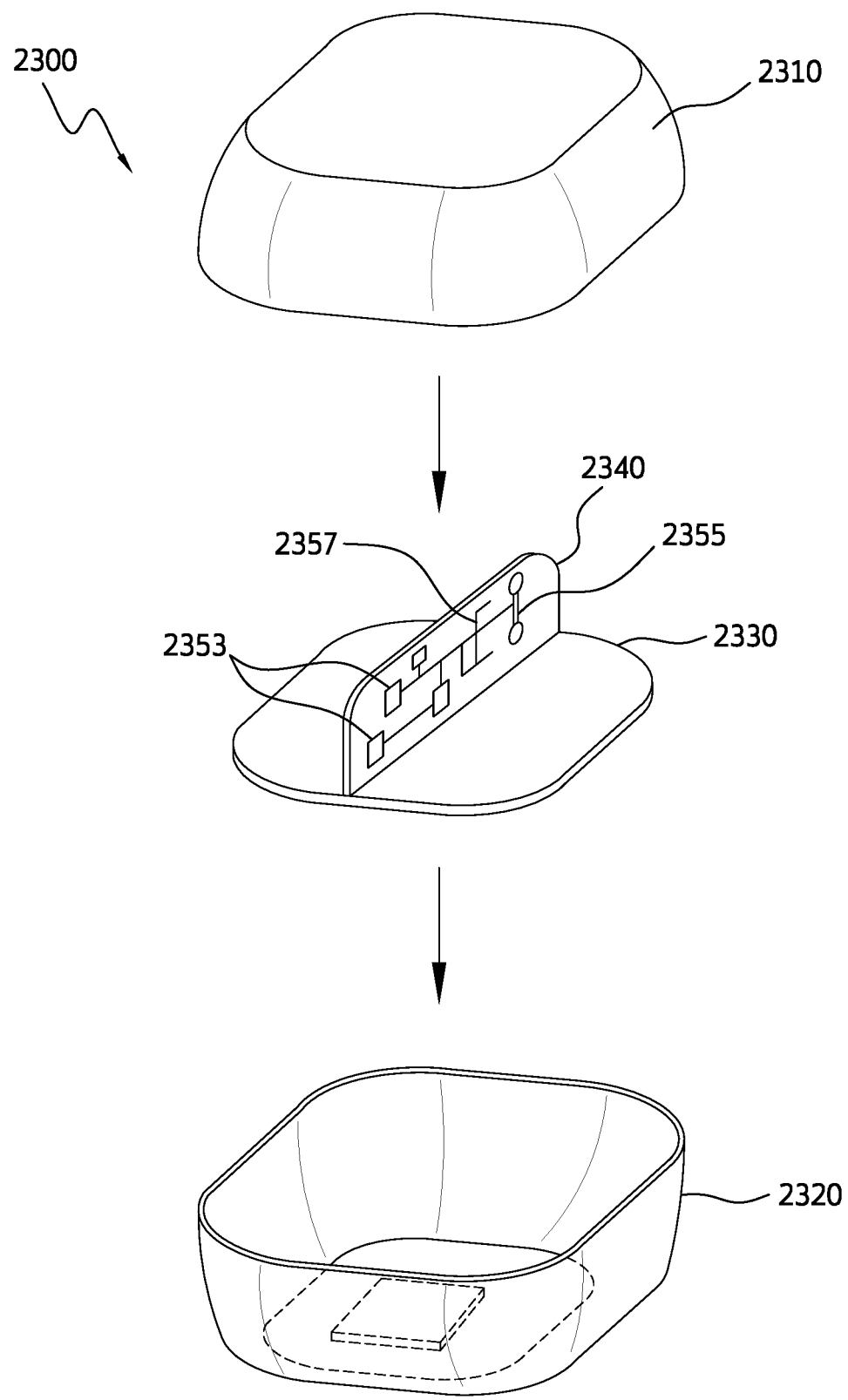

FIGS. 23A-23C show a sensing device in accordance with another embodiment. FIG. 23A shows a perspective view of sensing device 2300. FIG. 23B shows a cross-section of sensing device 2300. FIG. 23C shows components of sensing device 2300.

Sensing device 2300 has a cuboid shape with rounded corners. For example, sensing device 2300 have the shape of a cube, or of any rectangular prism, with rounded corners. Referring to FIG. 23C, sensing device 2300 includes a first portion 2310 and a second portion 2320 which are joined together. A platform 2330 holds a plate 2340 on which is disposed one or more sensors 2353, an antenna 2355, and associated electronic circuitry 2357. A quantity of a material 2360, such as a metal, is disposed in the concave inside surface of second portion 2320 to provide a weight. Sensors 2353 may include one or more of the following: a temperature sensor, an impedance/conductivity sensor, a pH sensor, a micro fiber composite (MFC) sensor, an accelerometer, an elevation sensor, a radio frequency identification (RFID) device, a humidity sensor, a GPS-based geolocation sensor, a salinity sensor, etc. In one embodiment, a salinity sensor may include a chloride ion electrode, for example.

Figure 23D:
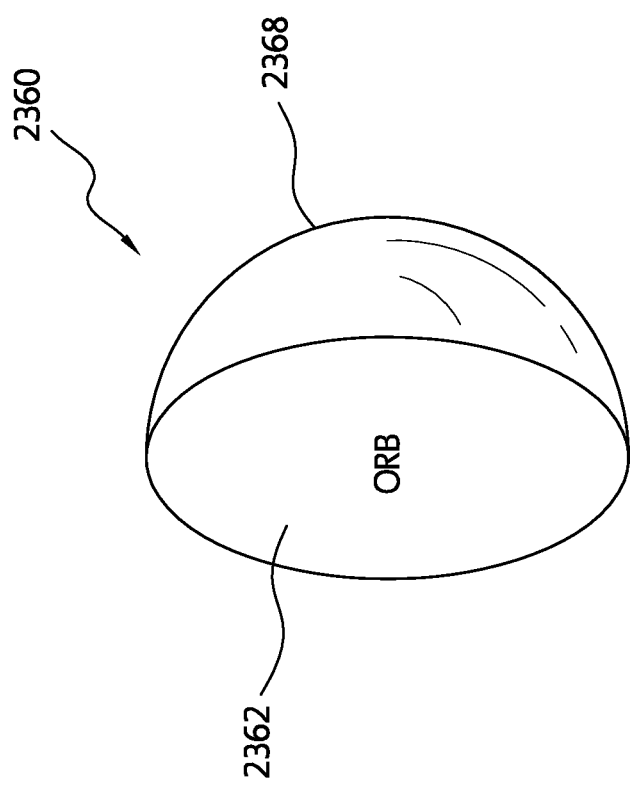
FIGS. 23D-23I show a sensing device in accordance with another embodiment.

FIGS. 23D-23I show a sensing device in accordance with another embodiment. Referring to FIG. 23D, a sensing device 2360 has a first side 2362 that is relatively flat (not semispherical) and a second side 2368 that has a semispherical shape.

Figure 23E:
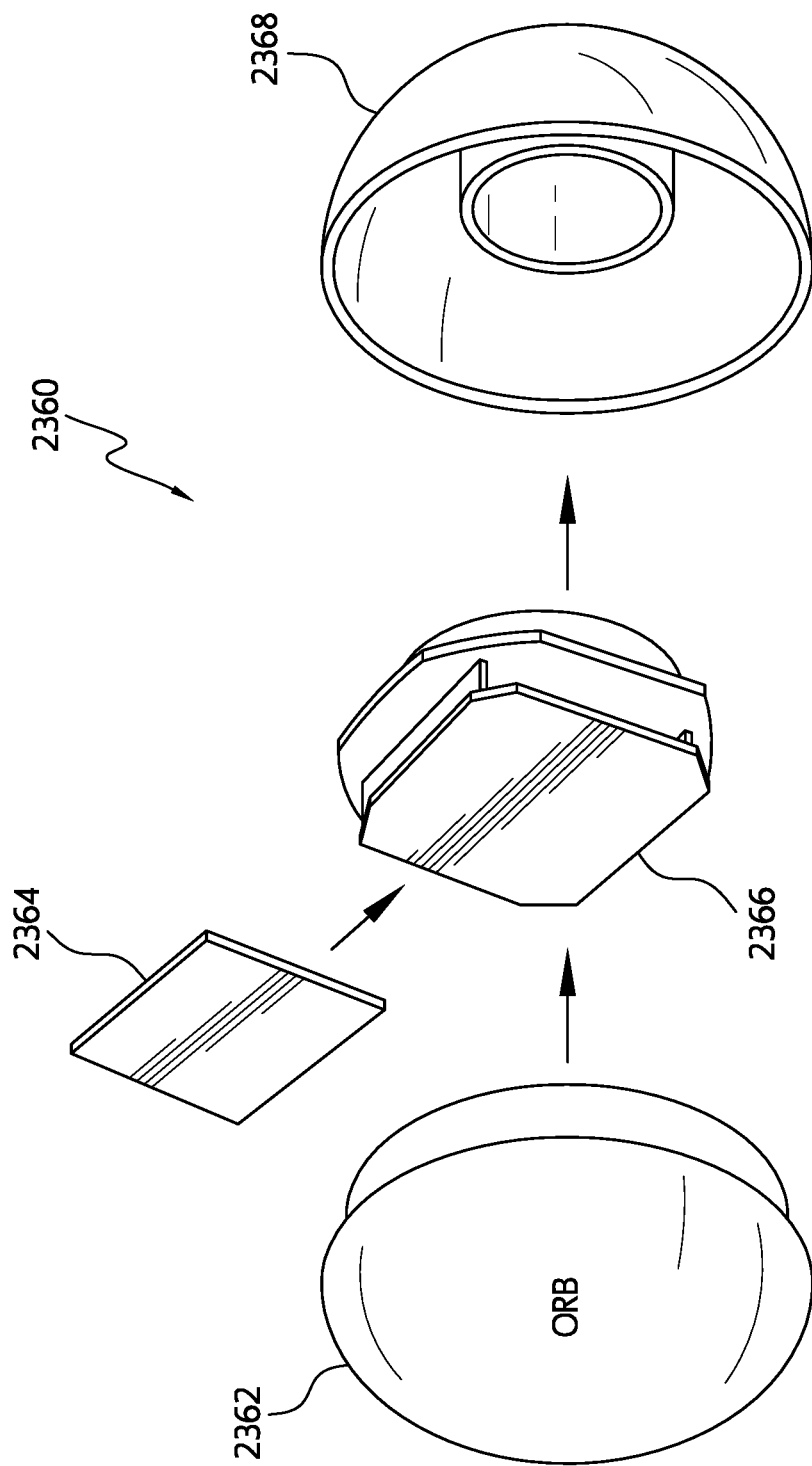

FIG. 23E shows components of sensing device 2360 in accordance with an embodiment. Sensing device 2360 includes a front cover portion 2362, a sensor device 2364, a sensor holder 2366, and a rear cover portion 2368. Front cover portion has a relatively flat surface. Rear cover portion 2368 has a semispherical shape. Sensor device 2364 fits into sensor holder 2366. Sensor holder 2366 is adapted to fit into and remain fixed within rear cover portion 2368. Front cover portion 2362 is adapted to be coupled to rear cover portion 2368, and thereby cover and protect sensor holder 2366 and sensor device 2364. In one embodiment, front cover portion 2362 is adapted to be coupled to rear cover portion 2368, with a seal being created at the junction of front cover portion 2362 and rear cover portion 2368. In other embodiments, sensing device 2360 may contain more than one sensor device.

Sensor device 2364 includes one or more sensors, including, for example, a temperature sensor, an impedance/ conductivity sensor, a pH sensor, a micro fiber composite (MFC) sensor, an accelerometer, an elevation sensor, a radio frequency identification (RFID) device, a humidity sensor, a GPS-based geolocation sensor, a salinity sensor, etc. In one embodiment, a salinity sensor may include a chloride ion electrode, for example. Sensor holder 2366 protects sensor device 2364 and may provide a protected environment in which sensor device 2364 may obtain measurements.

Figure 23F:
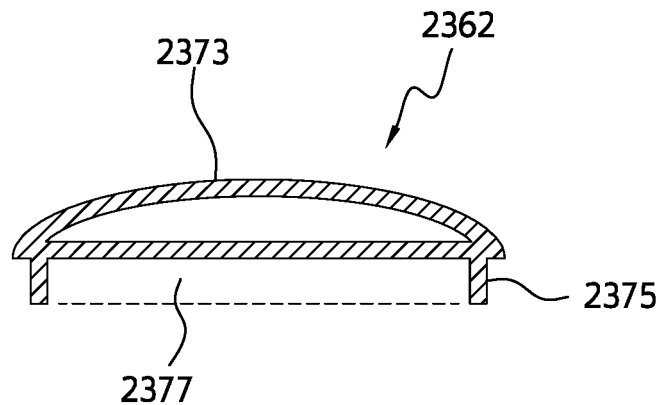

FIG. 23F shows a cross-section of front cover portion 2362 in accordance with an embodiment. Front cover portion 2362 includes a curved surface 2373 on a first side, and on a second side, a peripheral element 2375 defining an opening 2377. For example, peripheral element may have a circular shape and be disposed around the outer edge of front cover portion 2362.

Figure 23G:
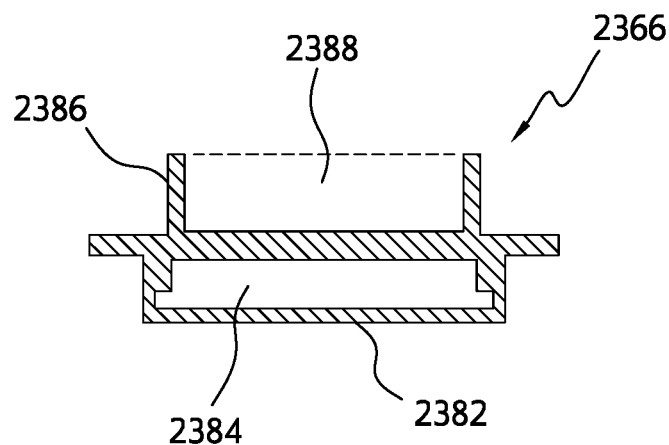

FIG. 23G shows a cross-section of sensor holder 2366 in accordance with an embodiment. Sensor holder 2366 includes a first part 2382 disposed on a first side of sensor holder 2366, which includes a volume 2384. Volume 2384 is adapted to receive and hold sensor 2364. For example, volume 2384 may provide a protected environment for sensor 2364, enabling sensor 2364 to obtain measurements. Sensor holder 2366 also includes a second element 2386 disposed on a second side. Second element 2386 defines an opening 2388. For example, second element 2386 may be disposed around a periphery of the second side of sensor holder 2366. For example, second element may be circular in shape.

Figure 23H:
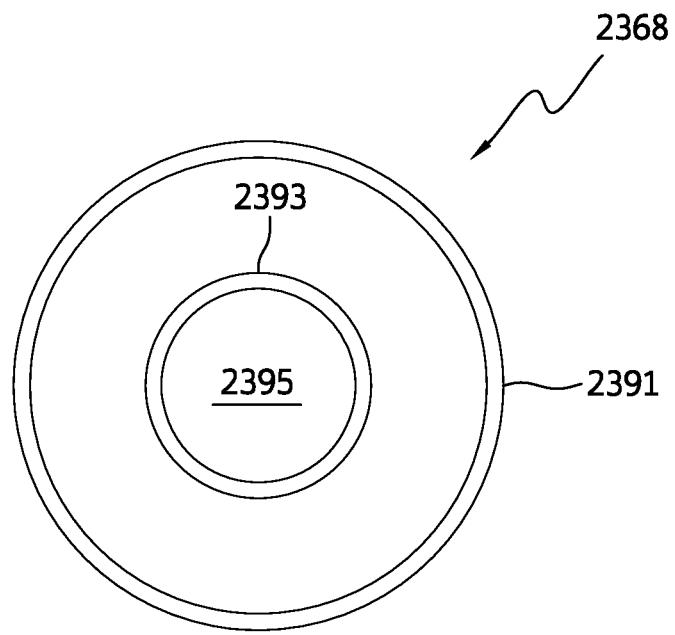

FIG. 23H shows a top view of rear cover portion 2368 in accordance with an embodiment. Rear cover portion 2368 includes semispherical surface 2391 and an inner element 2393, which defines an opening 2395. In one embodiment, the diameter of rear cover portion 2368 may be between 2.5 and 3.0 inches, for example. Other sizes may be used.

Figure 23I:
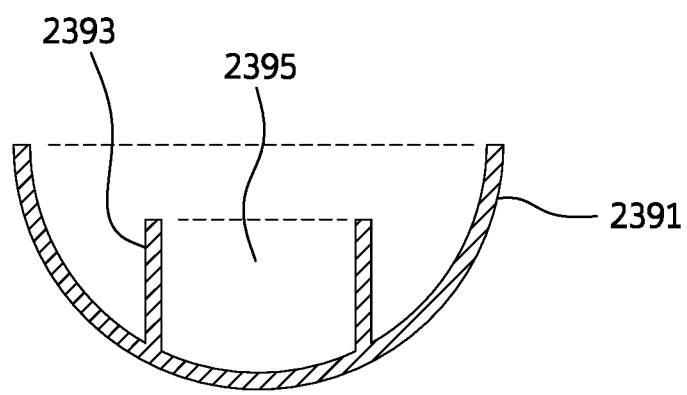

FIG. 23I shows a cross-section of rear cover portion 2368 in accordance with an embodiment. Inner element 2393 is disposed on inside surface of semispherical surface 2391. Inner element 2393 is adapted to engage with the second element 2386 of the second side of sensor holder 2366.

Figure 23J:
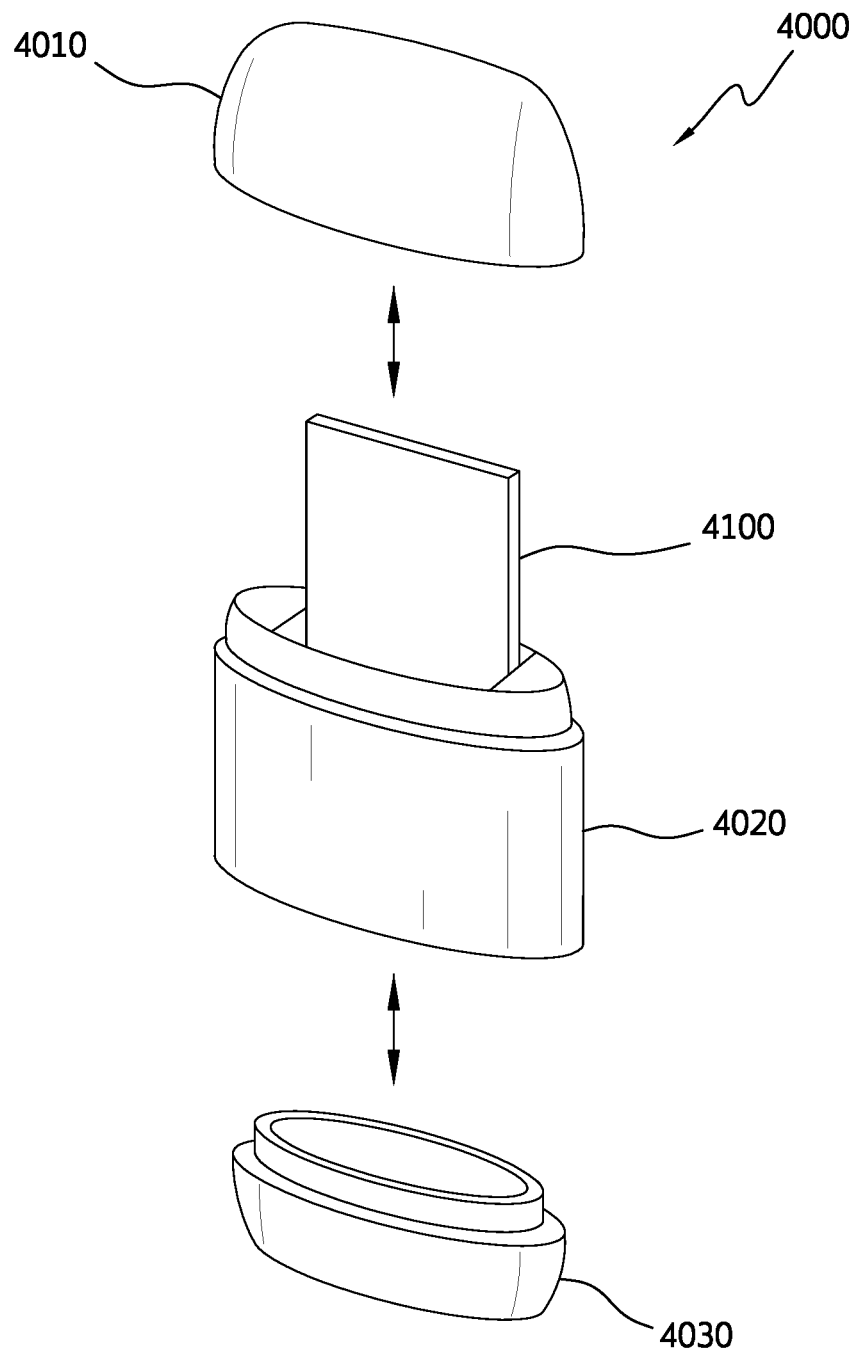
FIGS. 23J-23P show a sensing device in accordance with another embodiment.

FIGS. 23J-23P show a sensing device 4000 in accordance with another embodiment. FIG. 23J shows components of sensing device 4000. Sensing device 4000 includes a top cover portion 4010, a central cover portion 4020 and a bottom cover portion 4030. Sensing device 4000 also includes a sensor device 4100. Top cover portion 4010 is adapted to detachably connect to central cover portion 4020. Bottom cover portion 4030 is adapted to detachably connect to central cover portion 4020. Top cover portion 4010 and central cover portion 4020, when connected, define a volume. Sensor device 4100 is disposed within the volume defined by top cover portion 4010 and central cover portion 4020.

Sensor device 4100 includes one or more sensors, including, for example, a temperature sensor, an impedance/conductivity sensor, a pH sensor, a micro fiber composite (MFC) sensor, an accelerometer, an elevation sensor, a radio frequency identification (RFID) device, a humidity sensor, a GPS-based geolocation sensor, a salinity sensor, etc. In one embodiment, a salinity sensor may include a chloride ion electrode, for example. Top cover portion 4010 and central cover portion 4020 protect sensor device 4100 and may provide a protected environment in which sensor device 4100 may obtain measurements.

Figure 23K:
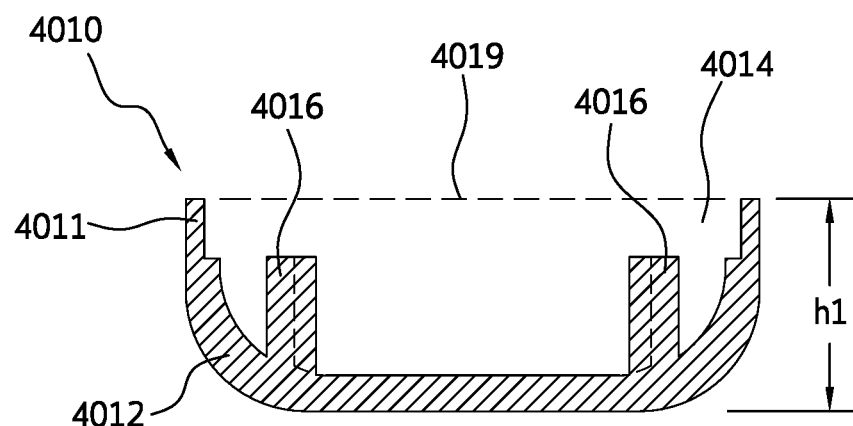
Figure 23L:
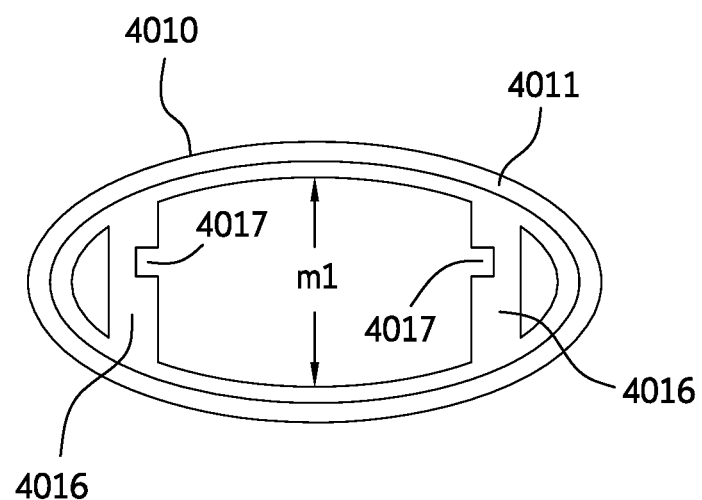

FIGS. 23K-23L show cross-sections of top cover portion 4010. Top cover portion 4010 includes an outer shell 4012 having an opening 4019. Top cover portion 4010 has a narrow peripheral section 4011 around the periphery of opening 4019. Top cover portion 4010 also includes two supports 4016. Each support 4016 includes a groove 4017. Grooves 4017 are adapted to receive sensor device 4100.

Top cover portion 4010 has a height dimension (h1), which may be between 20-30 mm, for example, more preferably 24.6 mm. Top cover portion has an internal width dimension (m1), which may be between 20-30 mm, for example, more preferably 24.0 mm.

Figure 23M:
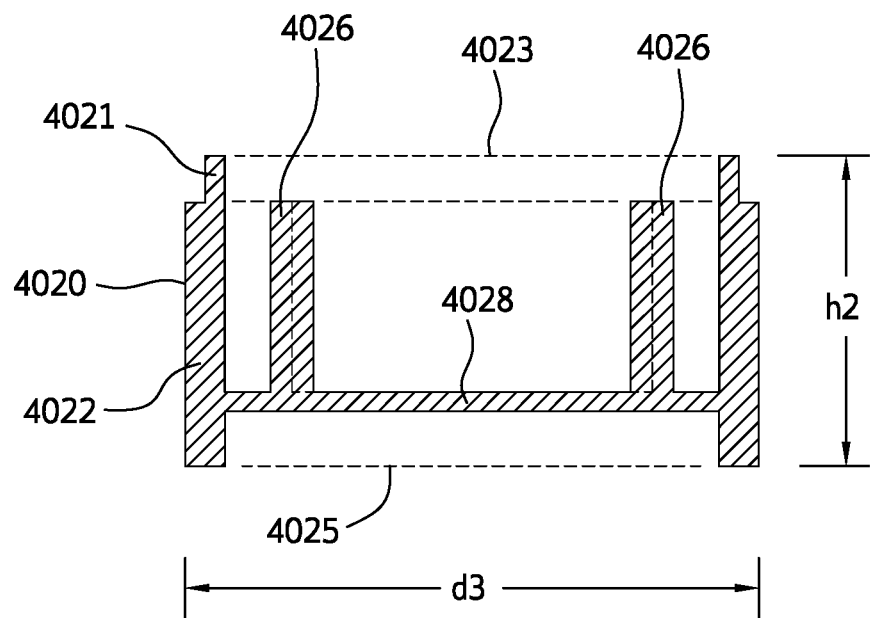
Figure 23N:
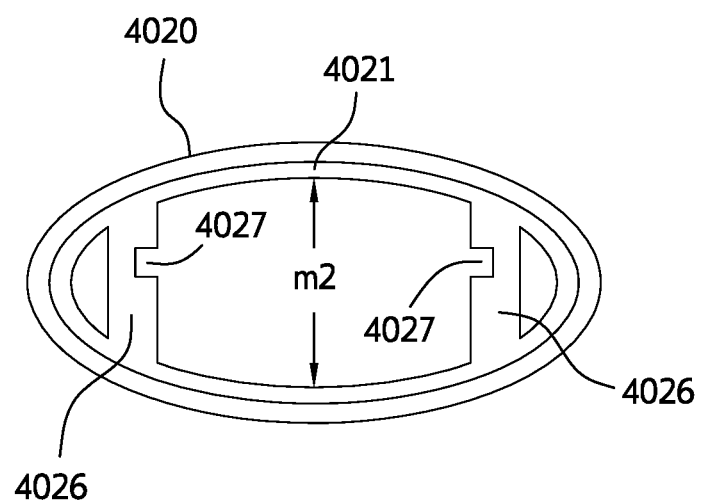

FIGS. 23M-23N show cross-sections of central cover portion 4020. Central cover portion 4020 has a top opening 4023 and a bottom opening 4025. Central cover portion 4020 has an outer shell 4022 with a narrow peripheral section 4021 around the periphery of upper opening 4023. Internally, central cover portion 4020 has a lower support 4028, and first and second internal supports 4026. Each internal support 4026 includes a groove 4027. Grooves 4027 are adapted to receive sensor device 4100.

Central cover portion 4020 has a width dimension (d3) which may be between 60-70 mm, for example, more preferably 65.4 mm. Central cover portion 4020 has a height dimension (h2) which may be between 30-40 mm, for example, more preferably 36.2 mm. Central cover portion 4020 has an internal width dimension (m2), which may be between 20-30 mm, for example, more preferably 24.0 mm.

Narrow peripheral section 4011 of upper cover portion 4010 is adapted to fit around and engage with narrow peripheral section 4021 of central cover portion 4020.

Figure 23O:
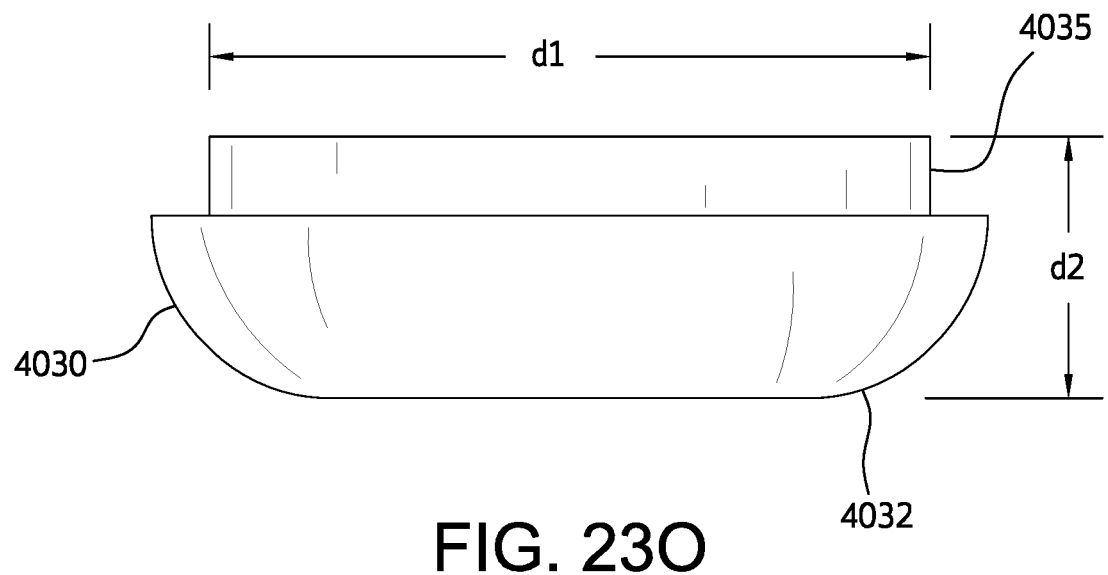
Figure 23P:
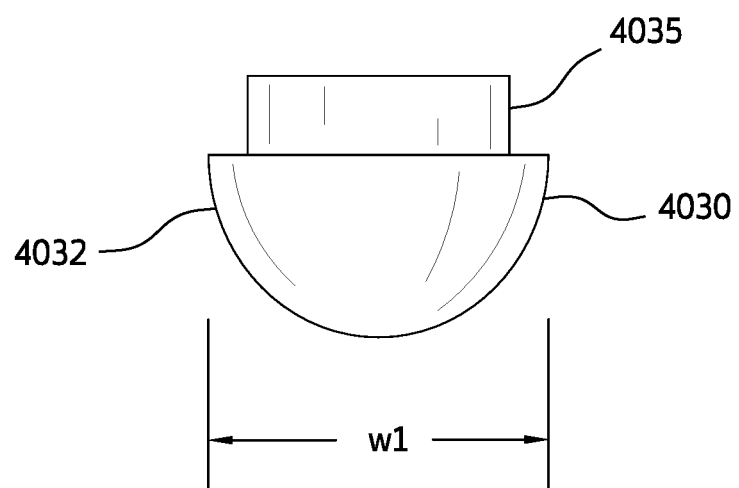

FIGS. 23O-23P show respective cross-sections of bottom cover portion 4030. Bottom cover portion 4030 includes an outer shell 4032 and a projecting portion 4035. Bottom cover portion 4030 has a height dimension (d2), which may be between 15-25 mm, more preferably 20.3 mm. Bottom cover portion 4030 has a width dimension (w1), which may be between 20-30 mm, more preferably 26.4 mm.

Projecting portion 4035 of bottom cover portion 4030 is adapted to fit into and engage with bottom opening 4025 of central cover portion 4020.

Sensor device 4100 is adapted to slide into and be secured within sensing device 4000. Specifically, sensor device 4100 is adapted to slide into grooves 4027 of central cover portion 4020. Sensor device 4100 may not fit entirely into central cover portion 4020, and a part of sensor device 4100 may remain exposed. Accordingly, when top cover portion 4010 is connected to central portion 4020, the exposed part of sensor device 4100 slides into grooves 4017 of top cover portion 4010. When top cover portion 4010 is coupled securely to central cover portion 4020, sensor device 4100 is secured within the sensing device 4000. Bottom cover portion 4030 is also coupled to central cover portion 4020.

Figure 24:
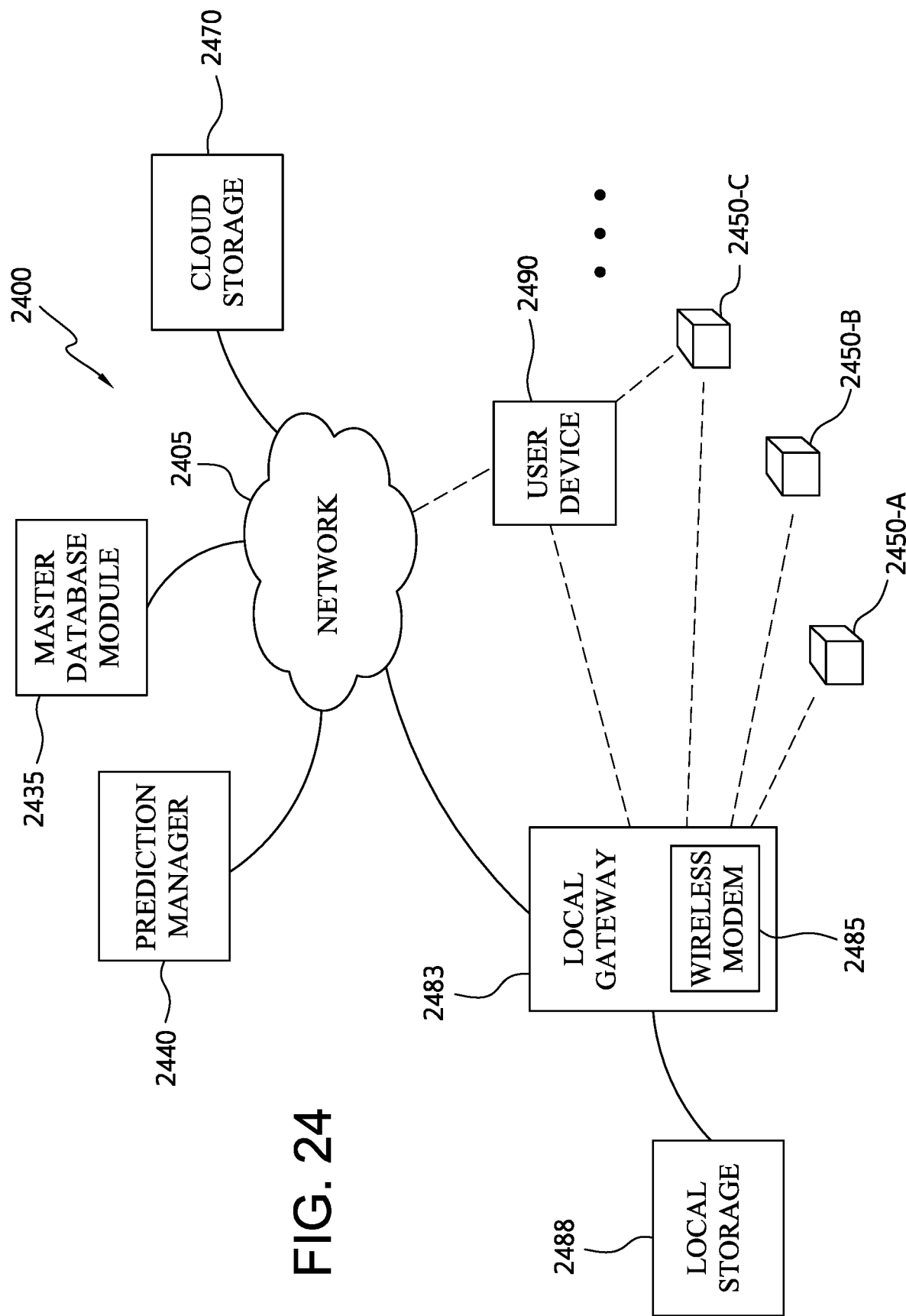
FIG. 24 shows a communication system in accordance with another embodiment.

FIG. 24 shows a communication system in accordance with another embodiment. Communication system 2400 includes a network 2405, which may include the Internet, for example, a master database module 2435, a prediction manager 2440, and a cloud storage 2470.

Communication system 2400 also includes a local gateway 2483, which is connected to network 2405. Local gateway 2483 includes a wireless modem 2485. Local gateway 2483 is linked to a plurality of sensing devices 2450-A, 2450-B, 2450-C, etc., which are disposed at various locations at a construction site, for example. Local gateway 2483 is also linked to a local storage 2488. Local gateway 2483 may from time to time store data, such as measurement data received from sensing devices 2450, in local storage 2488. Local gateway 2483 and local storage 2488 may be located at or near a construction site, for example.

Sensing devices 2450 are disposed at various sites at a construction site. Using methods and apparatus similar to those described above, each sensing device 2450 obtains measurements related to a respective concrete mixture. Each sensing device 2450 transmits measurement data to master database module 2435 via local gateway 2483 and network 2405. For example, each sensing device 2450 may transmit measurement data wirelessly to local gateway 2483, which transmits the measurement data to master database module 2435 via network 2405. Each sensing device 2450 may also transmit an identifier uniquely identifying itself. For example, an RFID tag embedded in each sensing device 2450 may transmit identification information. Communication system 2400 may include any number of sensing devices.

In one embodiment, multiple sensing devices 2450 may be located at a single location (e.g., a single construction site). In another embodiment, multiple sensing devices 2450 may be located at multiple locations (e.g., at multiple construction sites).

Communication system 2400 also includes a user device 2490, which may be a personal computer, laptop device, tablet device, cell phone, or other processing device which is located at a construction site and used by a technician at the site. User device 2490 may communicate with network 2405, with local gateway 2483, with a sensing device 2450, and/or with other devices within communication system 2400.

Master database module 2435 receives measurement data from one or more sensing devices 2450 and may analyze the measurement data. In the illustrative embodiment, master database module 2435 transmits the measurement data to prediction manager 2440 (or otherwise makes the data available to prediction manager 2440). Prediction manager 2440 may generate predictions concerning the behavior of one or more concrete specimens. For example, prediction manager 2440 may receive temperature, humidity, and/or location data from sensing device 2450-A and, based on the measurement data, generate predictions regarding the water-to-cementitious ratio, durability, strength, slump, maturity, etc., of the concrete mixture in which sensing device 2450-A is located. In one embodiment, the measurement data received by master database module 2435 is provided to a real-time model to project setting behavior and strength for the entire batch of concrete. In another embodiment, the measurement data is continually subject to statistical analysis to generate real-time projections, control charts, etc. Master database module 2435 may store the prediction data in cloud storage 2470. For example, prediction data may be stored in a database. Other data structures may be used to store prediction data.

In one embodiment, master database module 2435 may transmit measurement data and/or prediction information relating to water-to-cementitious ratio, durability, strength, slump, maturity, etc. to a user device such as user device 2490 to enable a technician to access and view the information. For example, user device 2490 may display measurement data and/or prediction data on a web page, or in another format.

In one embodiment, cloud storage 2470 may comprise a cloud storage system. Data obtained by a sensing device 2450 may be transmitted to and saved in cloud storage 2470 in real-time. A cloud implementation such as that illustrated by FIG. 24 may allow data from projects in multiple regions or multiple countries to be auto-consolidated in a single database.

Figure 25:
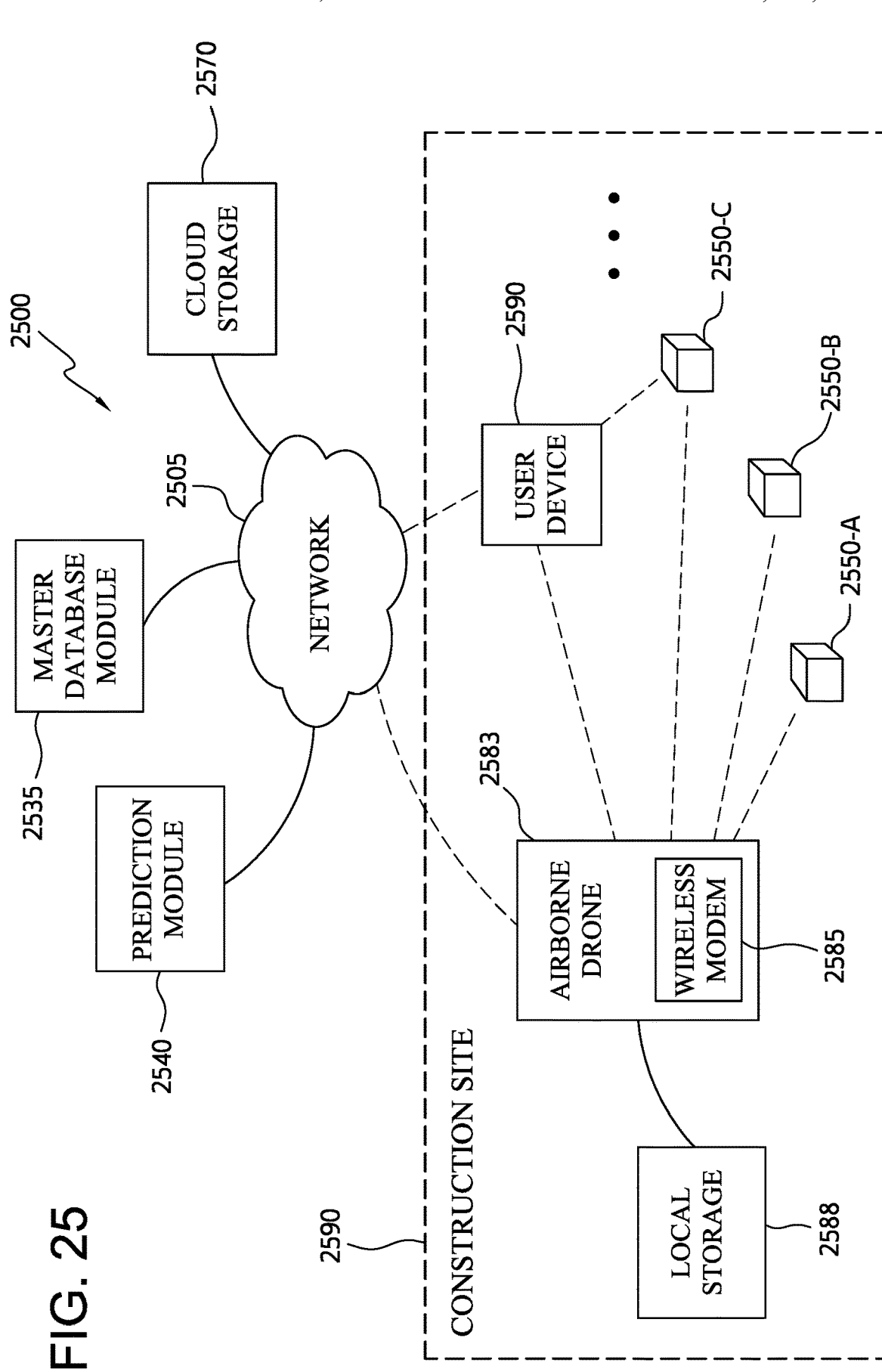
FIG. 25 shows a communication system in accordance with an embodiment.

In one embodiment, local gateway 2483 is located on an airborne drone device. For example, local gateway 2483 may be disposed on an airborne drone device that hovers over a construction site while work progresses. FIG. 25 shows a communication system in accordance with an embodiment. Communication system 2500 includes a network 2505, which may include the Internet, for example, a master database module 2535, a prediction manager 2540, and a cloud storage 2570.

Communication system 2500 also includes an airborne drone 2583, which flies above a construction site 2590. Airborne drone 2583 is connected to network 2505. Airborne drone 2583 includes a wireless modem/router 2585. A plurality of sensing devices including 2550-A, 2550-B, 2550-C, etc., are disposed at various locations at construction site 2590. Airborne drone 2583 is also linked to a local storage 2588. Airborne drone 2583 may from time to time store data, such as measurement data received from sensing devices 24550, in local storage 2588.

Figure 26:
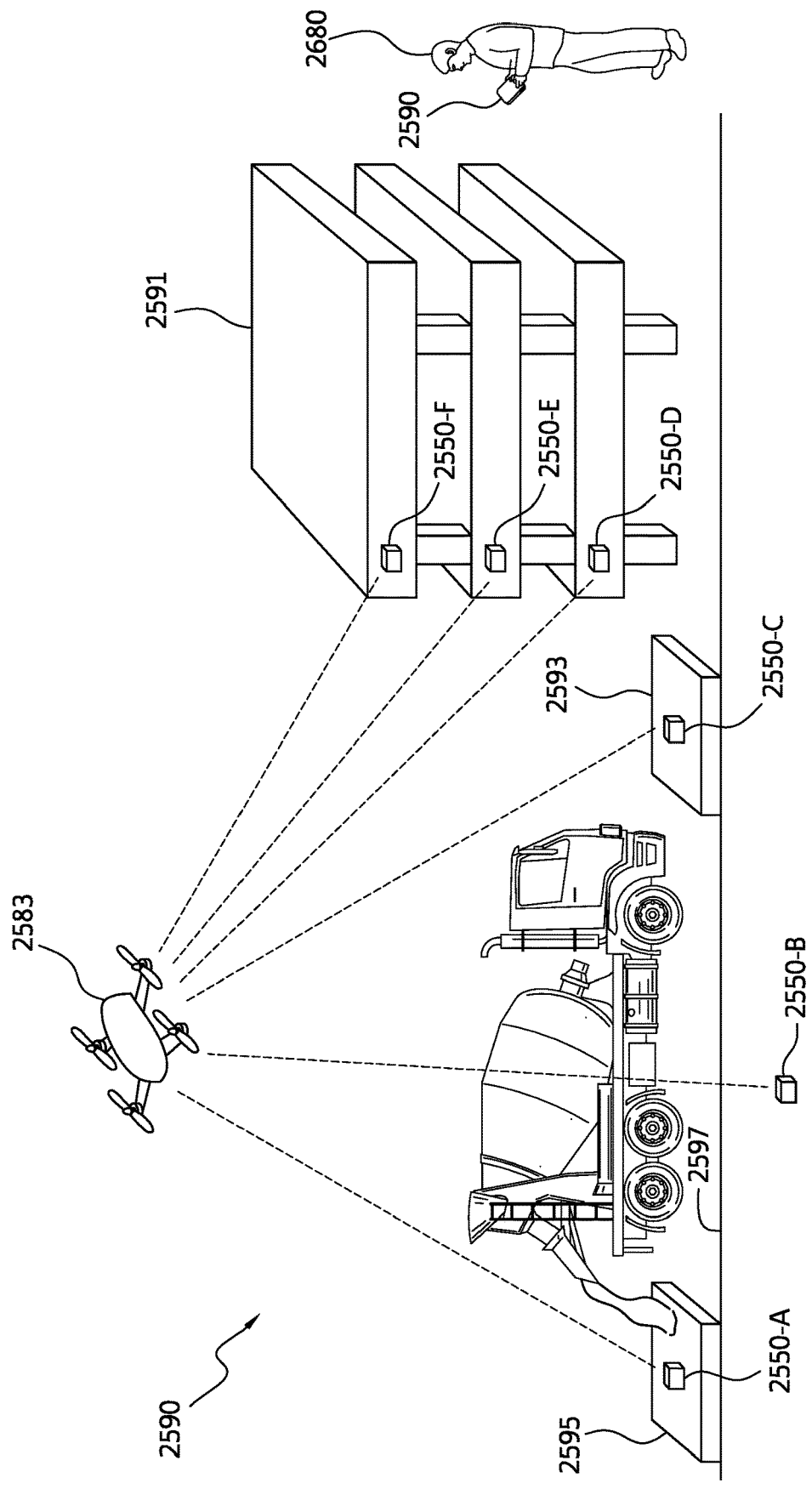
FIG. 26 shows a communication system operating at a construction site in accordance with an embodiment.

FIG. 26 shows a communication system operating at a construction site in accordance with an embodiment. Airborne drone 2583 flies above construction site 2590, which includes a plurality of concrete structures 2591, 2593, 2595, 2597, etc., which are in the process of being constructed. Sensing devices 2550-A, 2550-B, 2550-C, 2550-D, 2550-E, 2550-F are embedded in concrete within various structures at construction site 2590. For example, sensing device 2550-B is embedded in the concrete of a roadway 2597. Sensing devices 2550-D, 2550-E, and 2550-E are embedded in the concrete of different levels of a building. Each sensing device 2550 obtains measurements relating to the concrete in which it is embedded and transmits measurement data to airborne drone 2583.

Using methods and apparatus similar to those described above, each sensing device 2550 obtains measurements related to a respective concrete mixture. Each sensing device 2550 transmits measurement data to master database module 2535 via airborne drone 2583 and network 2505. For example, each sensing device 2550 may transmit measurement data wirelessly to airborne drone 2583, which transmits the measurement data to master database module 2535 via network 2505. Each sensing device 2550 may also transmit an identifier uniquely identifying itself. For example, an RFID tag embedded in each sensing device 2550 may transmit identification information. Communication system 2500 may include any number of sensing devices.

Communication system 2500 also includes a user device 2590, which may be a personal computer, laptop device, tablet device, cell phone, or other processing device which is located at a construction site and used by a technician at the site. User device 2590 may communicate with network 2505, with local gateway 2583, with a sensing device 2550, and/or with other devices within communication system 2500.

Master database module 2535 receives measurement data from one or more sensing devices 2550 and may analyze the measurement data. In the illustrative embodiment, master database module 2535 transmits the measurement data to prediction manager 2540 (or otherwise makes the data available to prediction manager 2540). Prediction manager 2540 may generate predictions concerning the behavior of one or more concrete specimens. For example, prediction manager 2540 may receive temperature, humidity, and/or location data from sensing device 2550-A and, based on the measurement data, generate predictions regarding the water-to-cementitious ratio, durability, strength, slump, maturity, etc., of the concrete mixture in which sensing device 2550-A is located. In one embodiment, the measurement data received by master database module 2535 is provided to a real-time model to project setting behavior and strength for the entire batch of concrete. In another embodiment, the measurement data is continually subject to statistical analysis to generate real-time projections, control charts, etc. Master database module 2535 may store the prediction data in cloud storage 2570. For example, prediction data may be stored in a database. Other data structures may be used to store prediction data.

In one embodiment, master database module 2535 may transmit measurement data and/or prediction information relating to water-to-cementitious ratio, durability, strength, slump, maturity, etc. to a user device such as user device 2590 to enable a technician to access and view the information. For example, user device 2590 may display measurement data and/or prediction data on a web page, or in another format.

In one embodiment, cloud storage 2570 may comprise a cloud storage system. Data obtained by a sensing device 2550 may be transmitted to and saved in cloud storage 2570 in real-time. A cloud implementation such as that illustrated by FIG. 25 may allow data from projects in multiple regions or multiple countries to be auto-consolidated in a single database.

The location of a particular sensing device using any suitable method. For example, each sensing device may have GPS capability; the sensing device may thus determine its location and transmit location data. Alternatively, the location of a sensing device may be determined using a triangulation method. For example, multiple receiving stations may receive a signal from a sensing device and use triangulation to determine the device's location.

In another alternative embodiment, a location of a sensing device may be determined based on an initial position and acceleration data. Thus, a sensing device may include an accelerometer and continually transmit acceleration and other motion data. An initial position of the sensing device may be determined (this may occur, for example, when a technician activates the sensing device at a construction site and drops the device into a concrete mixture). Master database module 2535 (or another component) may collect the initial position and the acceleration data and obtain the sensing device's current position based on the initial position data and the acceleration data representing movement from the initial position up to the current position.

Figure 27:
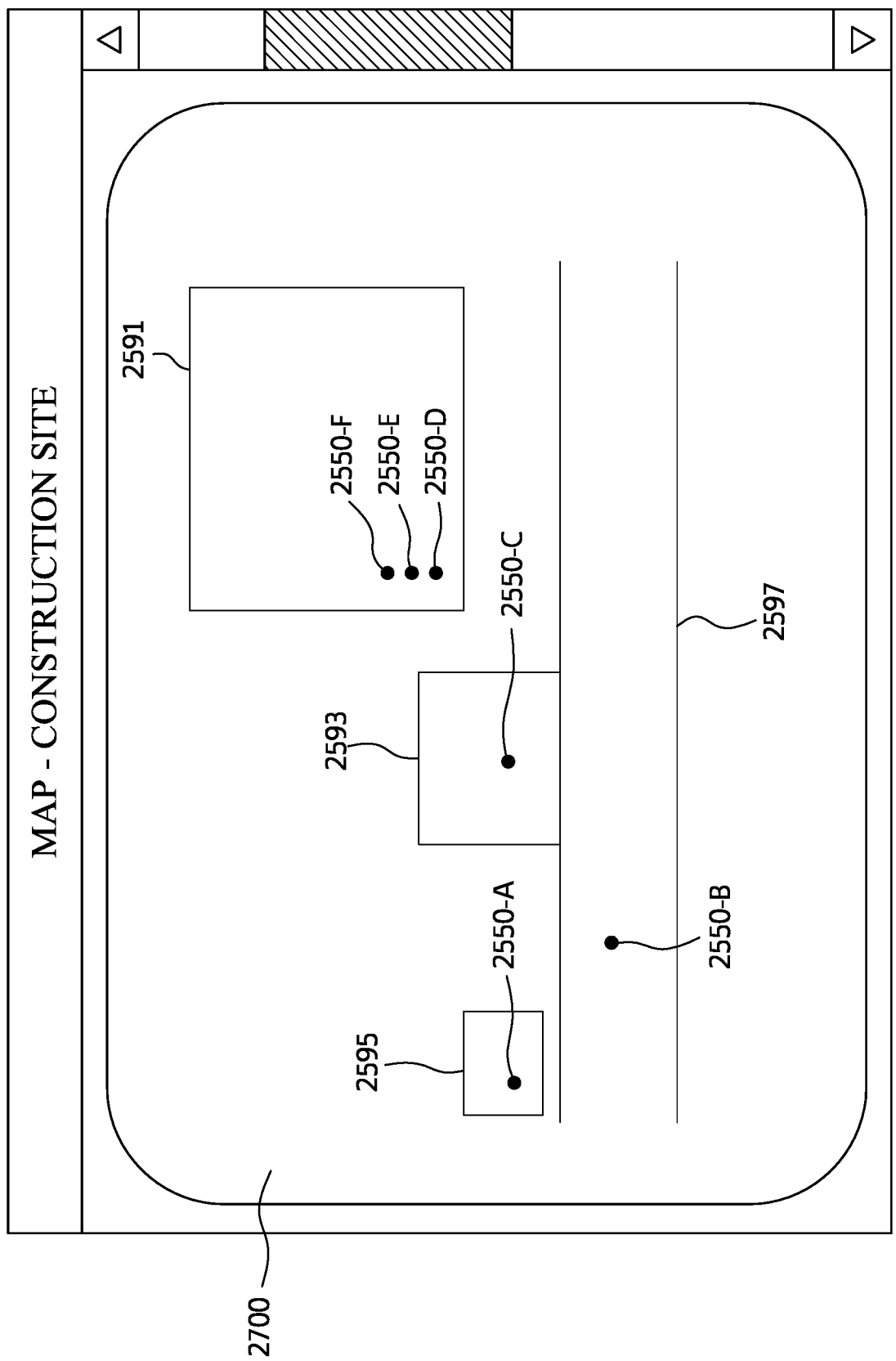
FIG. 27 shows a map of a construction site in accordance with an embodiment.

In accordance with another embodiment, master database module 2535 may compile data associated with a plurality of sensing devices 2550 and provides the information on a map. For example, master database module 2535 may generate a map of construction site 2590 showing the locations of various projects that are under construction and the locations of various sensing devices 2550 within the structures. FIG. 27 shows a map 2700 of construction site 2590 in accordance with an embodiment. Map 2700 shows structures 2591, 2593, 2595, 2597 and locations of sensing devices 2550-A, 2550-B, 2550-C, 2550-D, 2550-E, and 2550-F within the structures.

Master database module 2535 may provide the map in any suitable format to users. In the illustrative embodiment of FIG. 27, master database module 2535 presents map 2700 on a web page accessible via network 2505. For example, referring again to FIG. 26, a person 2680 at construction site 2590 may employ user device 2590 to access the web page and view map 2700.

Figure 28:
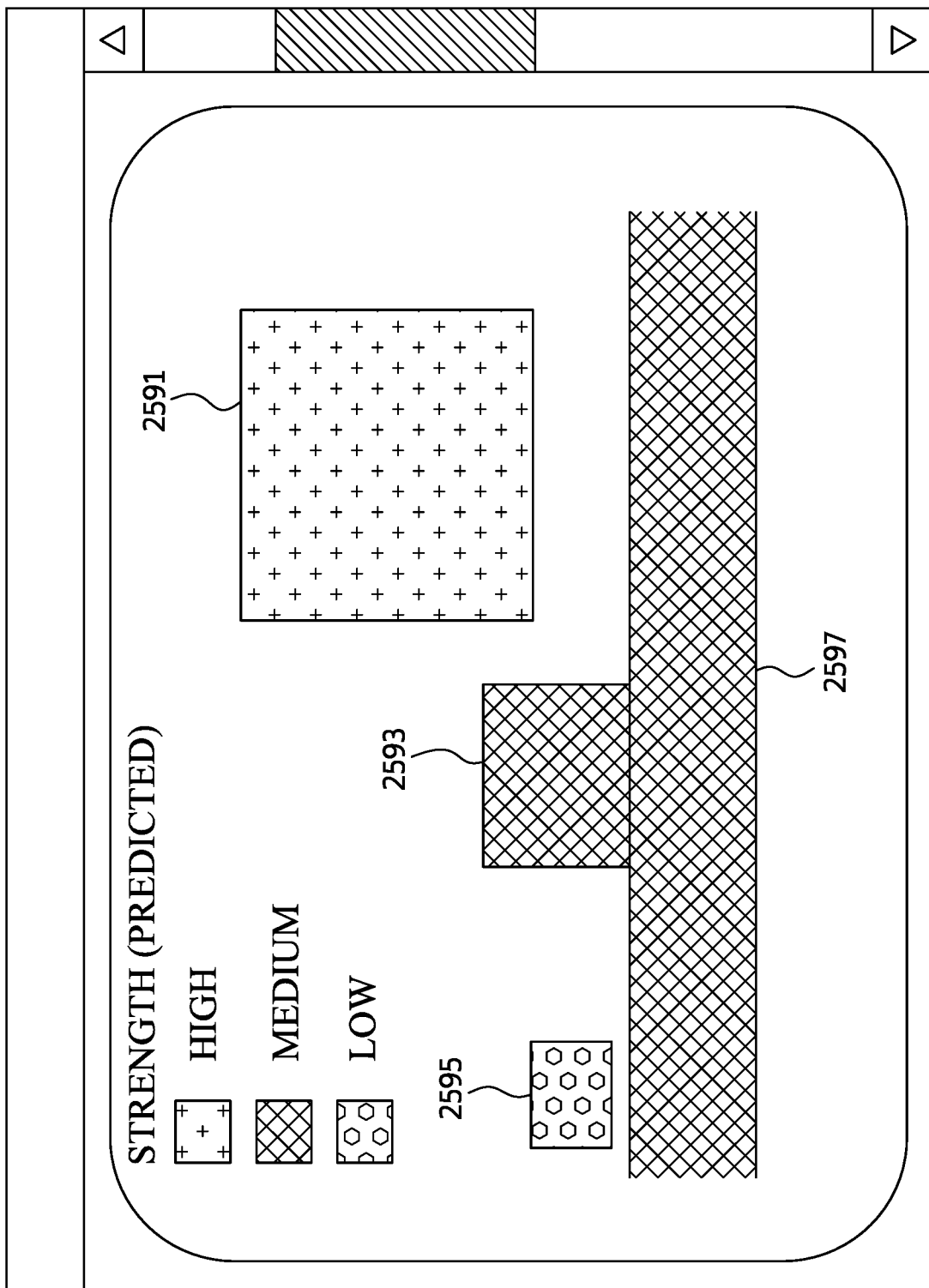
FIG. 28 shows a map of a construction site in accordance with another embodiment.

In accordance with another embodiment, master database module 2535 may generate a map of a construction site that displays prediction information generated by prediction module 2540. For example, master database module 2535 may generate a map such as that shown in FIG. 28. Map 2800 shows structures 2591, 2593, 2595, and 2597 at construction site 2590. Selected structures, or selected sections of structures, are color-coded, or shaded using different patterns, to indicate a prediction of the strength of the concrete for that respective structure or section. In the illustrative embodiment, structure 2595 is shown as having a (predicted) strength in a LOW range, structures 2593 and 2597 are shown as having a (predicted) strength in a MEDIUM range, and structure 2591 is shown as having a (predicted) strength in a HIGH range.

Figure 29:
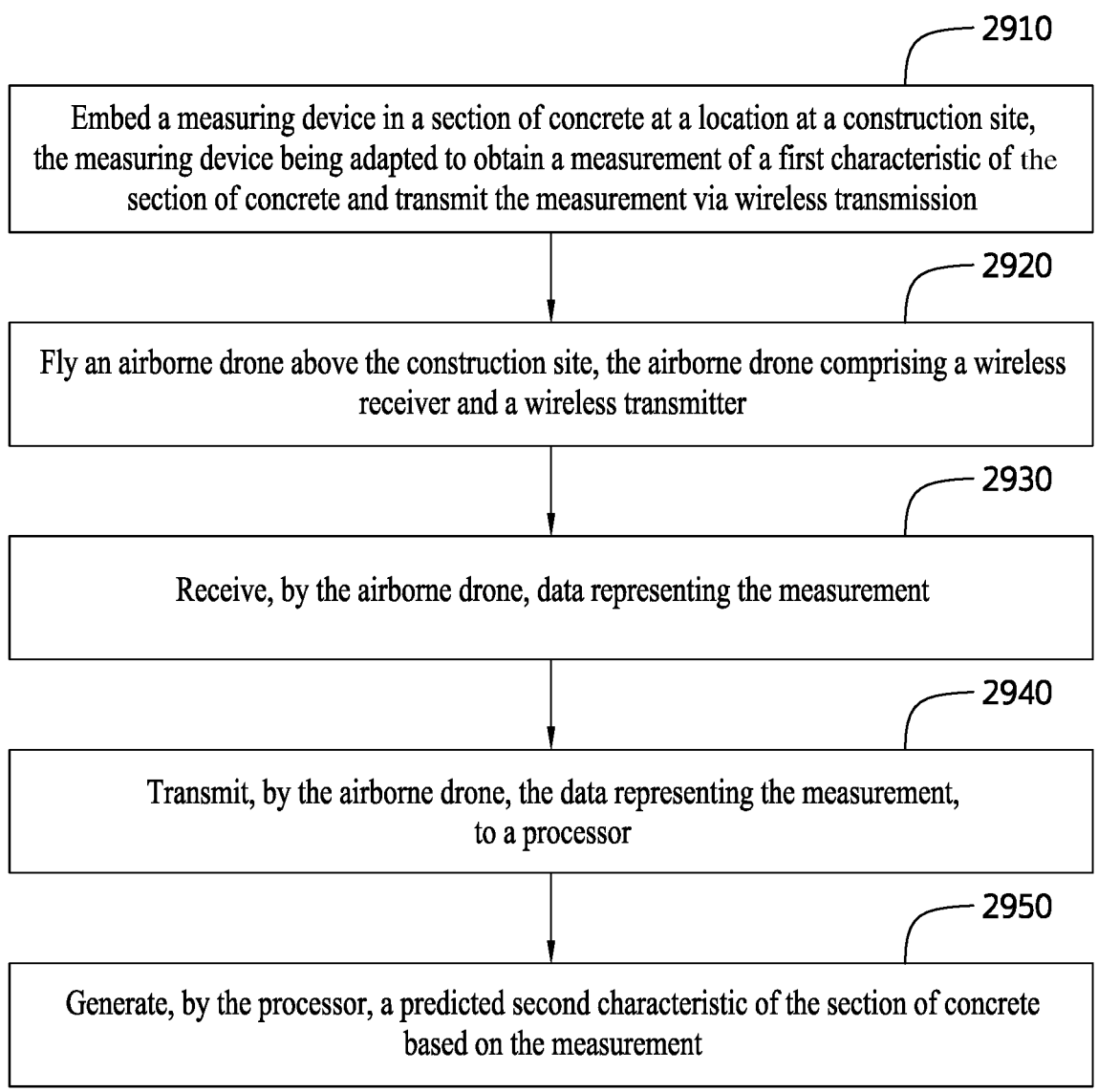
FIG. 29 is a flowchart of a method of obtaining and managing information relating to various structures at a construction site in accordance with an embodiment.

FIG. 29 is a flowchart of a method of obtaining and managing information relating to various structures at a construction site. The method of FIG. 29 is discussed with reference to FIGS. 25-28.

At step 2910, a measuring device is embedded in a section of concrete at a location at a construction site, the measuring device being adapted to obtain a measurement of a first characteristic of a section of concrete and transmit the measurement via wireless transmission. Sensing devices 2550-A, 2550-B, 2550-C, 2550-D, 2550-E, and 2550-F are embedded in the concrete used to build structures 2595, 2597, 2593, and 2591 at construction site 2590. The sensing devices may be placed in the concrete while the concrete is at a production facility, while the concrete is being transported in a concrete mixing truck, while the concrete is being poured from the truck into a form at the construction site (e.g., by dropping the sensing device into a chute proximate the truck), or after the concrete has been poured from the truck.

At step 2920, an airborne drone is flown above the construction site, the airborne drone comprising a wireless receiver and a wireless transmitter. Airborne drone 2583 is flown and operated above construction site 2590.

At step 2930, data representing the measurement is received by the airborne drone. Each of the sensing devices 2550 obtains one or more measurements of one or more characteristics of the concrete in which it is embedded. For example, each sensing device 2550 may obtain measurements of temperature, humidity, pH levels, location-related measurements, etc. Each sensing device 2550 transmits the measurement data wirelessly. Airborne drone 2583 receives the measurement data from each sensing device 2550.

At step 2940, the data representing the measurement is transmitted by the airborne drone to a processor. As airborne drone 2583 receives measurement data from sensing devices 2550, airborne drone 2583 transmits the measurement data to master database module 2535, via network 2505.

At step 2950, a predicted second characteristic of the section of concrete is generated, by the processor, based on the measurement. Master database module 2535 may generate a prediction, or may transmit the measurement data to prediction module 2540 and cause prediction module 2540 to generate prediction information, for one or more characteristics of a selected portion of concrete at construction site 2590. A prediction may be made for a characteristic of a section of concrete at construction site 2590 based on measurement data received from a sensing device embedded in the respective section of concrete. For example, a prediction of the strength of the concrete in structure 2595 may be generated based on measurement data received from sensing device 2550-A. A prediction of the strength of the concrete in structure 2597 may be generated based on measurement data received from sensing device 2550-B. A prediction of the strength of the concrete in structure 2593 may be generated based on measurement data received from sensing device 2550-C. A prediction of the strength of the concrete in structure 2591 may be generated based on measurement data received from sensing devices 2550-D, 2550-E, and 2550-F. Predictions of other characteristics of the concrete may be generated in a similar manner.

Master database module 2535 may provide a map such as that shown in FIG. 27 showing the locations of the various sensing devices. In the illustrative embodiment, master database module 2535 provides a web page showing map 2700. A user 2680 present at the construction site employs user device 2590 to access the web page and view the map. Master database module 2535 also provides map 2800

(shown in FIG. 28) showing predicted strength information in graphical form. Master database module 2535 may provide a second web page displaying map 2800. User 2680 accesses the web page to view map 2800.

In accordance with various embodiments described herein, a sensing device is disposed inside a drum of a concrete mixing truck. The sensing device is adapted to obtain one or more measurements of a characteristic of the concrete mixture and to transmit information representing the measurement(s). A concrete mixture is disposed in the drum of the mixing truck. The concrete mixture and the sensing device are transported in the concrete mixing truck from a first location to a second location. While the sensing device and the concrete mixture are inside the drum of the concrete mixing truck and being transported from the first location to the second location, the sensing device obtains one or more measurements of a first characteristic of the concrete mixture. For example, the sensing device may obtain one or more measurements of the temperature, humidity, or other characteristic, of the concrete mixture. The sensing device transmits information representing the measurement(s). For example, the sensing device may transmit a signal to an antenna disposed on the drum of the mixing truck. The antenna may receive the signal and transmit the signal outside the drum of the mixing truck. A second device disposed outside the concrete mixing truck receives the signal from the first device. For example, the second device may be a user device, such as a computer, cell phone, tablet device, etc., held by a person. Alternatively, the second device may be a personal computer device. Alternatively, the second device may be a wireless router, which transmits the signal via a network to a processor such as a master database module.

Figure 30:
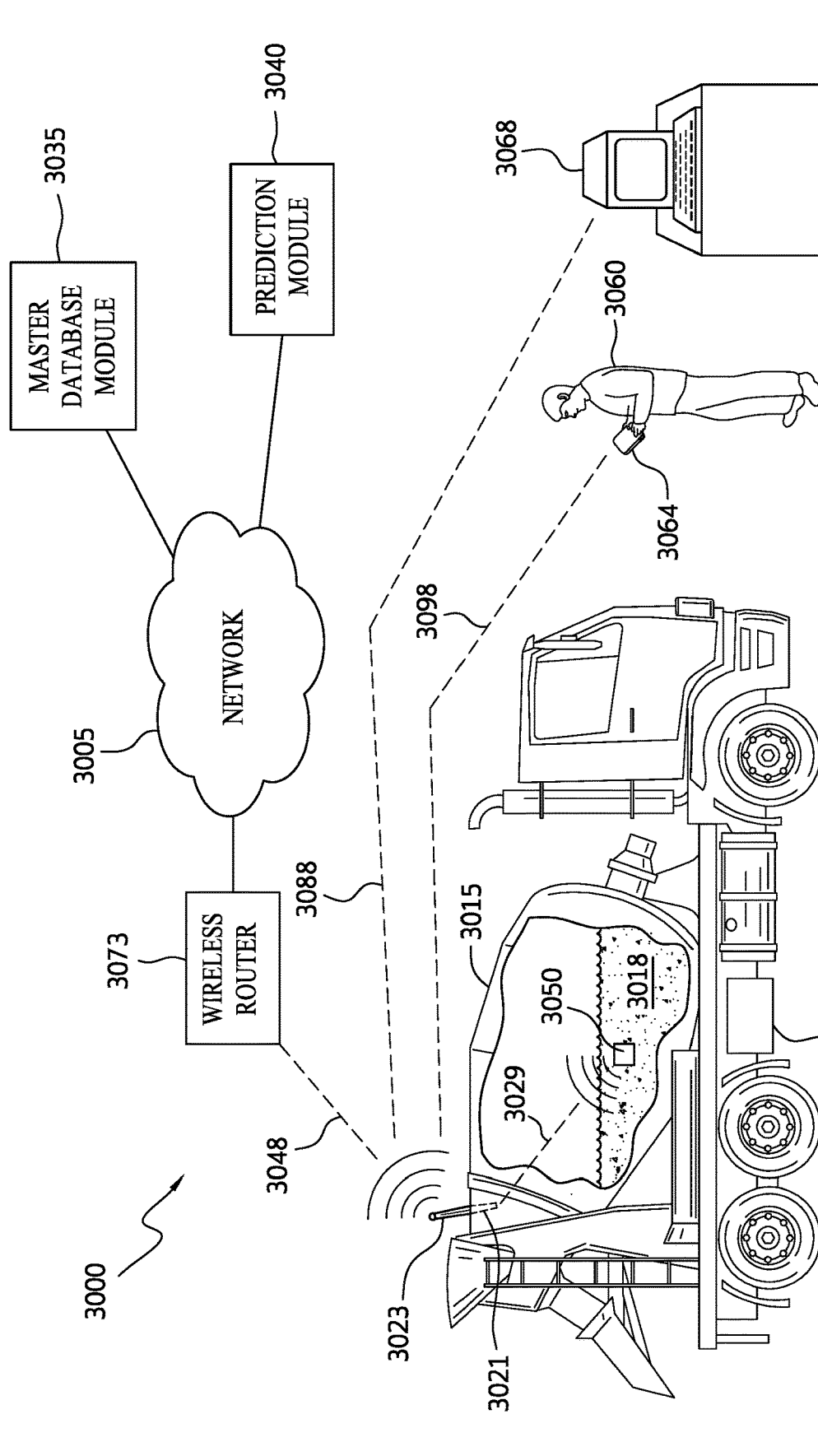
FIG. 30 shows a communication system in accordance with an embodiment.

FIG. 30 shows a communication system in accordance with an embodiment. Communication system 3000 includes a concrete mixing truck 3010 having a drum 3015. An antenna device having a first receiving portion 3021 inside drum 3015 and a second transmitter portion 3023 outside drum 3023 is disposed on drum 3015. Drum 3015 holds a concrete mixture 3018. A sensing device 3050 is disposed inside drum 3015. For example sensing device 3050 may be in concrete mixture 3018. System 3000 also includes a network 3005, which may be the Internet, for example. System 3000 also includes a wireless router 3073 connected to network 3005, a master database module 3035, and a prediction module 3040. Communication system also includes a user device 3064, which is employed by a user 3060, and a processing device 3068, which may be a personal computer, for example. User device 3064 may be a cell phone, a tablet device, a laptop device, etc.

In the illustrative embodiment, sensing device 3050 obtains one or more measurements of a first characteristic of concrete mixture 3018. Sensing device 3050 transmits a signal containing information representing the measurement(s), via wireless transmission. Antenna device 3023 receives the signal inside drum 3015 and transmits the signal outside drum 3015.

The signal may be received by wireless router 3073, which transmits the signal via network 3005 to master database module 3035. Master database module 3035 and/or prediction module 3040 then generates a prediction or calculation of a second characteristic of the concrete mixture based on the measurement(s). For example, a prediction or calculation of the strength of concrete mixture 3018 may be determined. The prediction or calculation of the second characteristic (e.g., the strength of concrete 3018) may be displayed on a display device (e.g., a display screen).

The signal may be received by user device 3064 (which may be a cell phone or tablet device, for example). Alternatively, the signal may be routed through wireless router 3073 to user device 3064. User device 3064 may then generate a prediction or calculation of a second characteristic of the concrete mixture based on the measurement(s). For example, a prediction or calculation of the strength of concrete mixture 3018 may be determined. The prediction or calculation of the second characteristic (e.g., the strength of concrete mixture 3018) may be displayed on a display device (e.g., a display screen).

The signal may be received by processing device 3068, which may generate a prediction or calculation of a second characteristic of the concrete mixture based on the measurement(s). For example, a prediction or calculation of the strength of concrete mixture 3018 may be determined. The prediction or calculation of the second characteristic (e.g., strength) may be displayed on a display device (e.g., a display screen).

Figure 31:
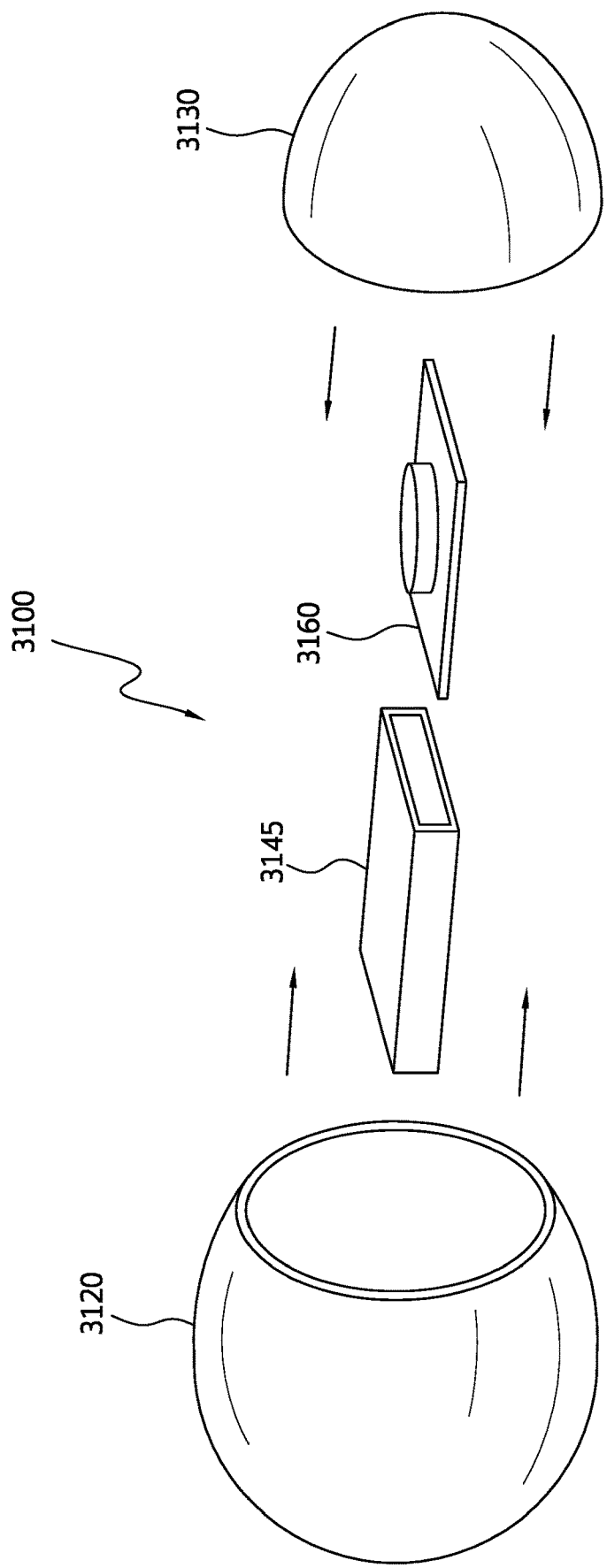
FIG. 31 shows components of a sensing device in accordance with an embodiment.

FIG. 31 shows components of a sensing device in accordance with another embodiment. Sensing device 3100 includes a first shell portion 3120 and a second shell portion 3130. First and second shell portions 3120, 3130 join to form an egg-shaped shell. Sensing device 3100 also includes sensor device enclosure 3145 and a sensor device 3160. Sensor device 3160 includes at least one sensor adapted to measure one or more parameters or characteristics, such as temperature, humidity, pH, salinity, conductivity, motion, acceleration, pressure, location, etc. Sensor device 3160 also includes a transmitter adapted to transmit measurement data wirelessly. Sensor device enclosure 3145 is adapted to receive and hold sensor device 3160. First shell portion 3120 is adapted to receive sensor device enclosure 3145. Sensor device enclosure 3145 is adapted to fit into first shell portion 3120.

In the illustrative embodiment, sensing device 3100 is assembled as follows: sensor device 3160 is fitted into sensor device enclosure 3145, sensor device enclosure 3145 is fitted into first shell portion 3120, first shell portion 3120 is joined to second shell portion 3130 to form an egg-shaped sensing device. The joint between first and second shell portions 3120, 3130 may be sealed, for example. When assembled, the outer shell of the device (formed from first shell portion 3120 and second shell portion 3130) is waterproof, allowing sensing device 3100 to operate submerged or partially submerged in a liquid (such as, for example, water, a concrete mixture, etc.)

Figure 32:
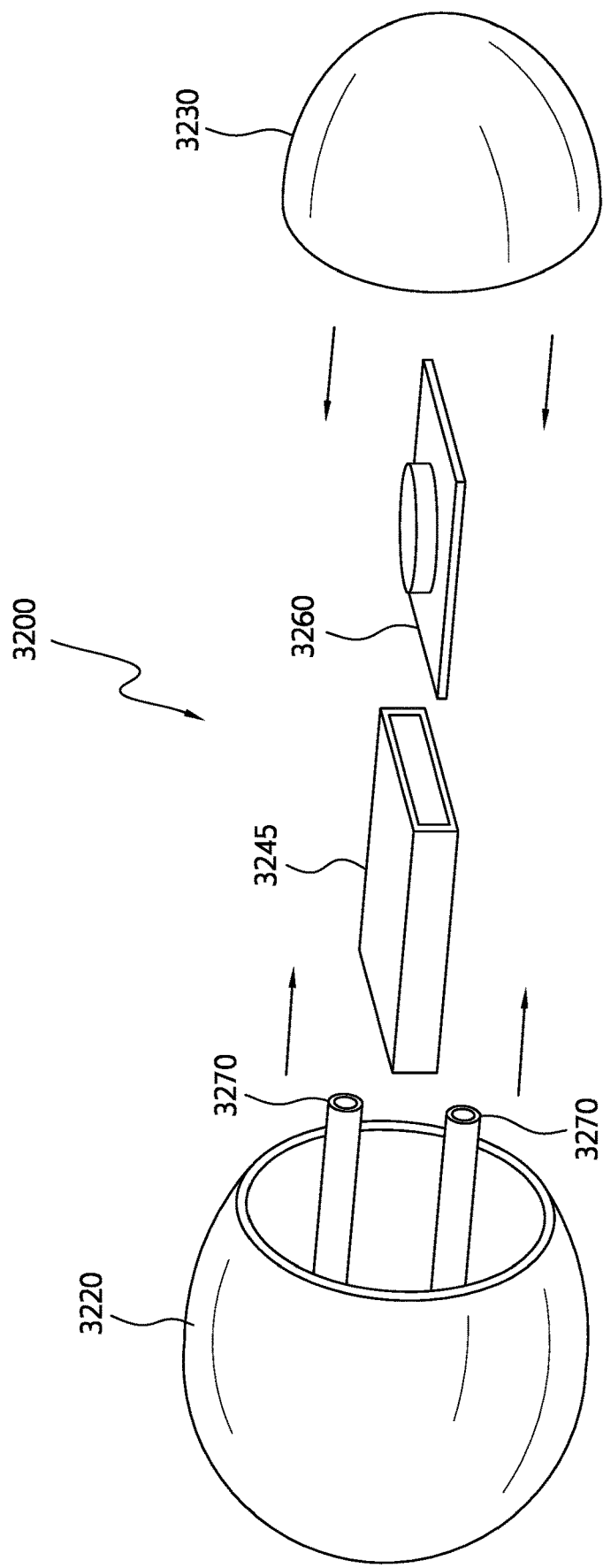
FIG. 32 shows components of a sensing device in accordance with an embodiment.

FIG. 32 shows components of a sensing device in accordance with another embodiment. Sensing device 3200 includes a first shell portion 3220 and a second shell portion 3230. First and second shell portions 3220, 3230 join to form an egg-shaped shell. Sensing device 3200 also includes sensor device enclosure 3245 and a sensor device 3260. Sensor device 3260 includes at least one sensor adapted to measure one or more parameters or characteristics, such as temperature, humidity, pH, salinity, conductivity, motion, acceleration, pressure, location, etc. Sensor device 3260 also includes a transmitter adapted to transmit measurement data wirelessly. Sensor device enclosure 3245 is adapted to receive and hold sensor device 3260. First shell portion 3220 is adapted to receive sensor device enclosure 3245. Sensor device enclosure 3125 is adapted to fit into first shell portion 3220.

First shell portion 3220 also includes first and second chimneys 3270. More chimneys may be used. Each chimney 3270 is a channel allowing the passage of gas and liquids between the outside of sensing device 3200 and the inside of sensing device. In the illustrative embodiment, each chimney 3270 is a hollow tube having a first open end inside of sensing device 3200 and a second open end on the outside surface of sensing device 3200. A chimney may have other shapes and sizes. In the illustrative embodiment, the chimney 3270 allows air and/or a liquid, including, for example, a concrete mixture, a water mixture, etc., to flow between the outside of sensing device 3200 and the inside of sensing device 3200.

Figure 33A:
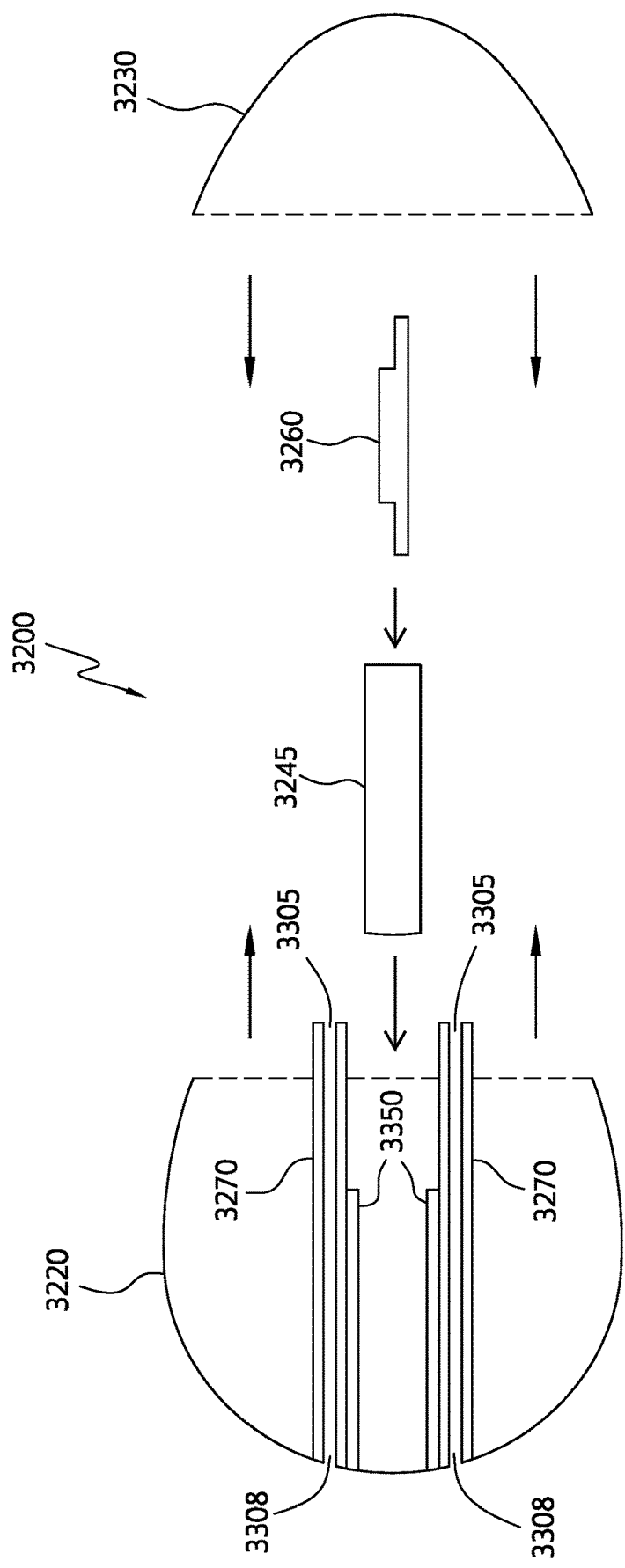
FIG. 33A shows a cross sectional view of components of a sensing device in accordance with an embodiment.
Figure 33B:
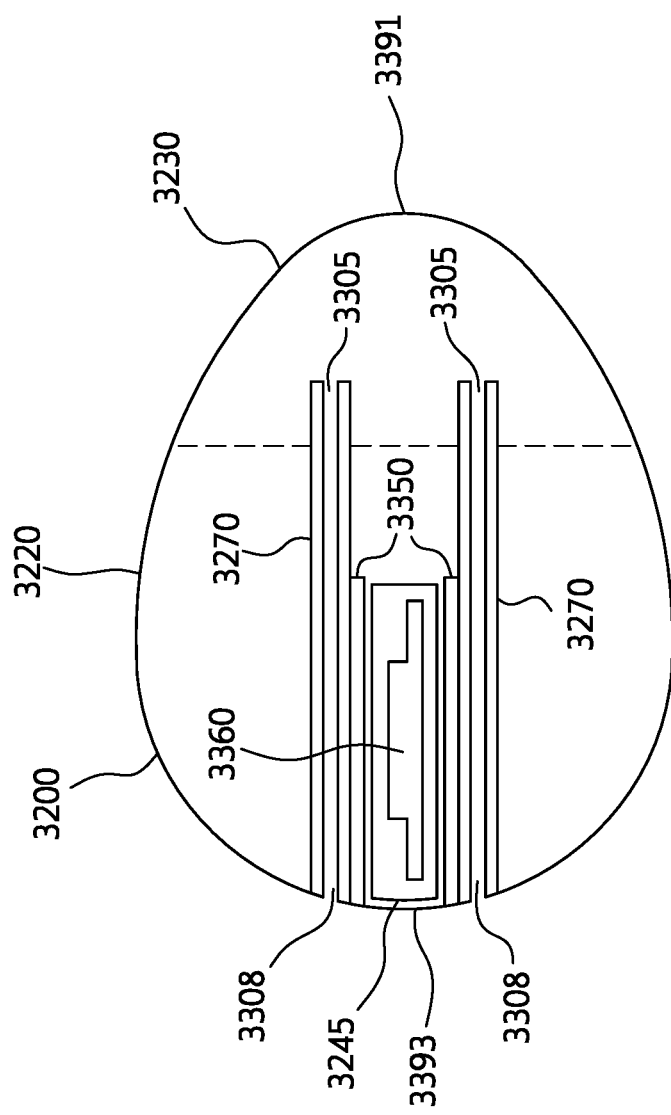
FIG. 33B shows a cross sectional view of a sensing device in accordance with an embodiment.

FIG. 33A shows a cross sectional view of components of a sensing device in accordance with an embodiment. FIG. 33B shows a cross sectional view of a sensing device in assembled form in accordance with an embodiment. As illustrated in FIG. 33A-33B, sensing device 3200 is assembled as follows: sensor device 3260 is fitted into sensor device enclosure 3245, and sensor device enclosure 3245 is fitted into first shell portion 3220. Sensor device enclosure 3245 is adapted to fit between chimneys 3305. First shell portion 3220 is joined to second shell portion 3230 to form an egg-shaped sensing device, as shown in FIG. 33B. The joint between first and second shell portions 3120, 3130 may be sealed, for example.

When assembled, sensing device 3200 has a first, flatter and wider end 3393 and a second, narrower end 3391, causing the sensing device to have a shape similar to that of an egg.

While in the illustrative embodiment sensing device 3200 includes two chimneys 3270, in other embodiments a sensing device may have a single chimney or may have more than two chimneys.

Figure 34:
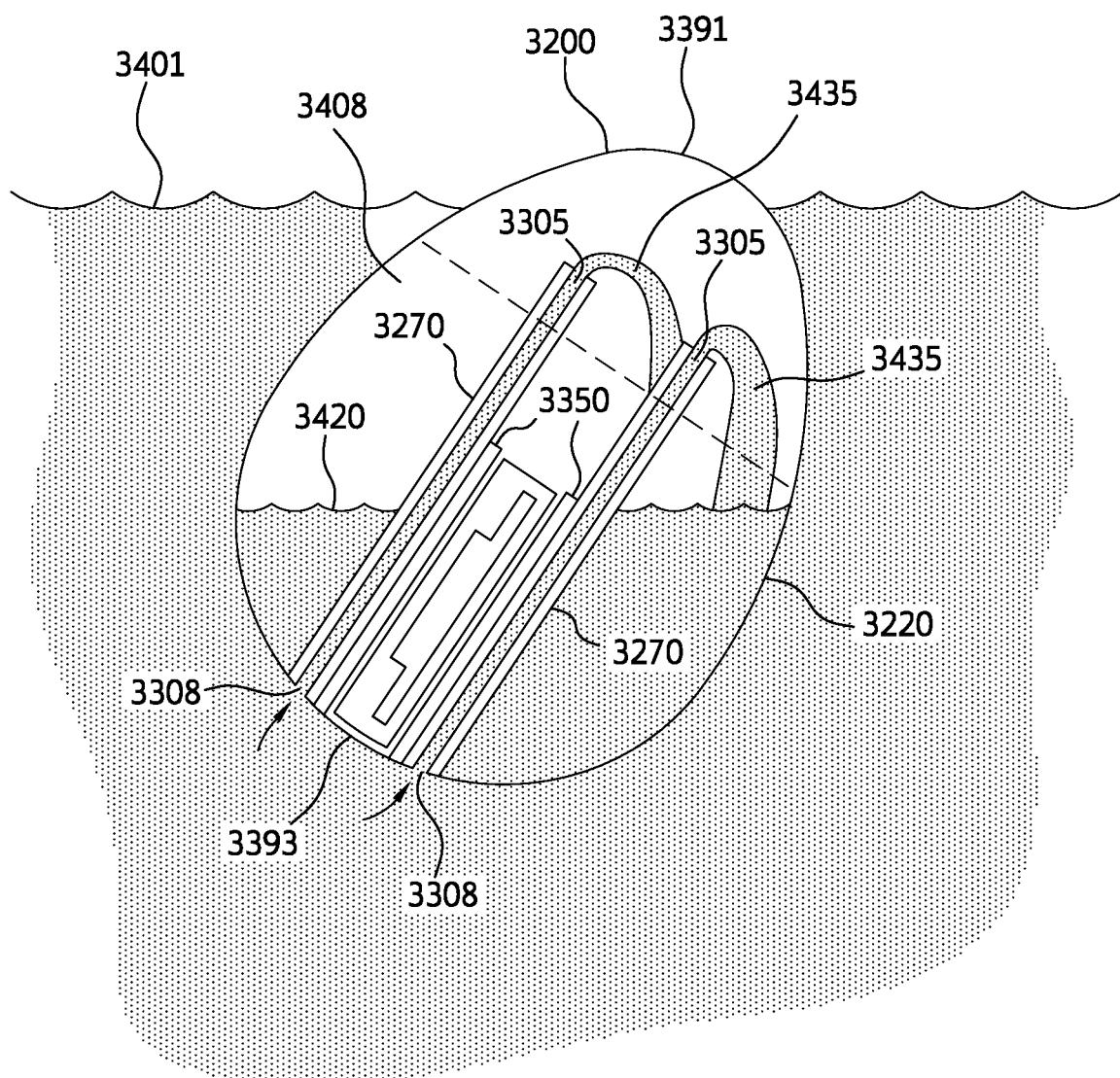
FIG. 34 shows a sensing device in a mixture in accordance with an embodiment.
Figure 35:
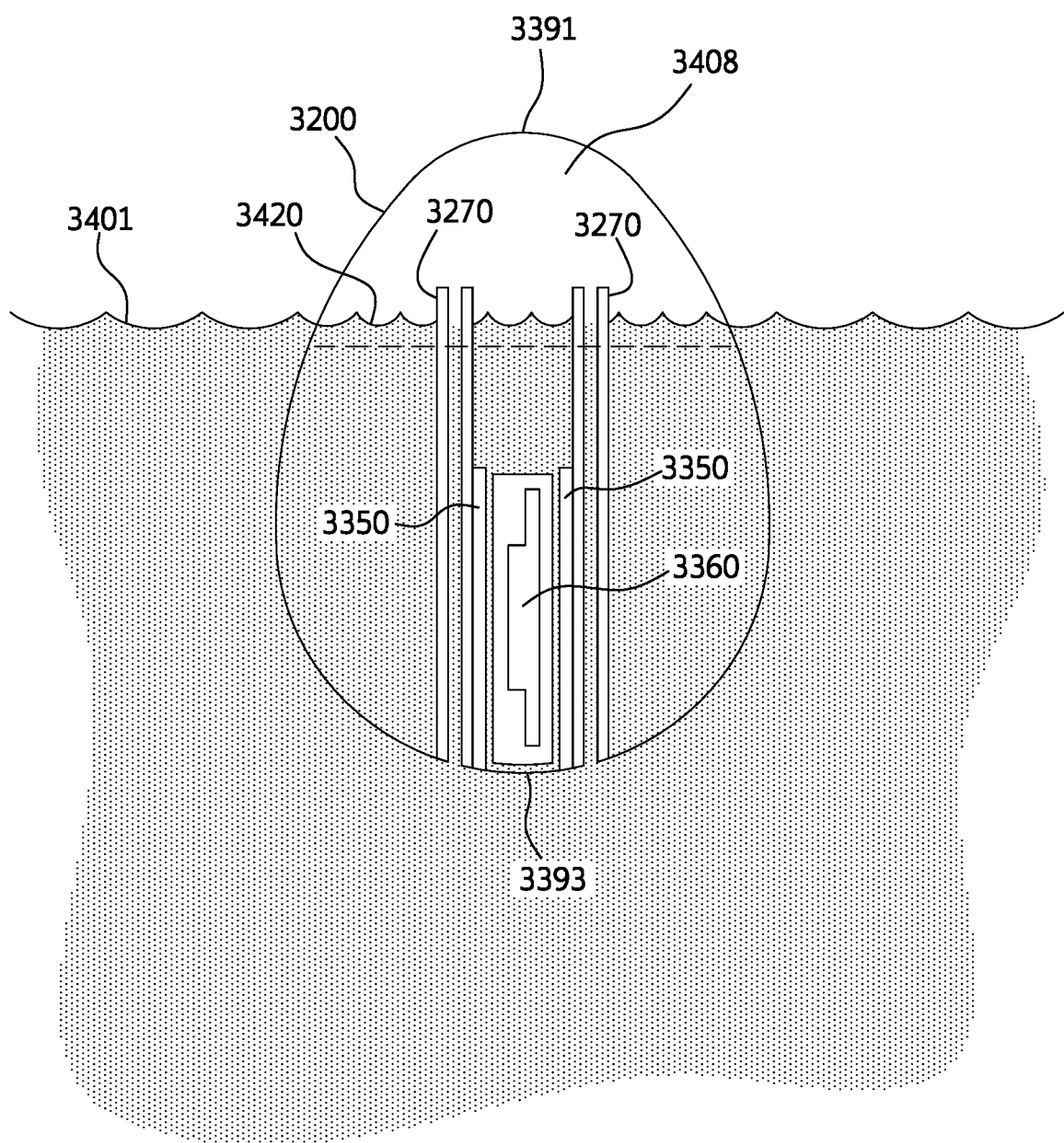
FIG. 35 shows a sensing device in a mixture in accordance with an embodiment.

In accordance with an embodiment, sensing device 3200 is inserted into a mixture, which may be, for example, a concrete mixture, a water mixture, or another liquid or semi-liquid substance. For example, sensing device 3200 may be placed in a concrete mixture that is to be used to form a structural element at a construction site. FIGS. 34-35 show a sensing device submerged in a mixture 3401 in accordance with an embodiment. Mixture 3401 may be a concrete mixture, a water mixture, etc. When sensing device is submerged or partially submerged in mixture 3401, as shown in FIG. 34, the mixture enters holes 3308 of chimneys 3270, passes through chimneys 3270 into the interior of sensing device 3200. Referring to FIG. 3200, a flow 3435 of mixture 3401 stream through chimneys 3270 and enters the interior of sensing device 3200. The flow accumulates inside of sensing device 3200, forming a quantity 3420 of the mixture inside the sensing device.

Due in part to the egg shape of sensing device 3200, the flatter, wider end 3393 of sensing device 3200 is heavier than narrow end 3391 and therefore the sensing device 3200 tends to orient itself with flatter end 3393 below narrow end 3391. Accordingly, the quantity 3420 of the mixture that flows from chimneys 3270 accumulates within the sensing device at or near the flatter, wider end 3393, as shown in FIG. 34. The added weight of quantity 3420 of the mixture reinforces the weight differential between the two ends of sensing device 3200. As a result, sensing device 3200 floats in the mixture 3401 with flatter, wider end 3393 pointing downward and narrower end 3391 pointing upward.

A volume 3408 of air remains inside of sensing device 3200, and migrates to the top, near narrower end 3391. Volume 3408 provides buoyancy and contributes to the weight differential between flatter end 3393 and narrower end 3391, further causing narrower end 3391 to remain above flatter end 3393. In the illustrative embodiment, flatter end 3393 remains submerged within mixture 3401 while narrower end 3391 remains above the surface of the mixture.

Referring to FIG. 35, an equilibrium is reached at which the flow of the mixture through chimneys 3270 ceases and sensing device 3200 floats in mixture 3401 with narrow end 3391 pointing upward. Volume 3408 of air provides buoyancy, while the shape of sensing device 3200, and the quantity 3420 of mixture that is inside of the sensing device, cause sensing device 3200 to float with flatter, wider end 3393 in a submerged position below narrower end 3391. The parameters of the equilibrium, including the quantity of mixture that must accumulate within the sensing device before equilibrium is reached, and how much of the sensing device remains submerged and how much remains above the surface) depend on a variety of factors including the size, shape, and weight of sensing device 3200, the nature of mixture 3401, etc.

After sensing device 3200 is placed within mixture 3401, sensing device 3200 obtains measurements relating to characteristics of mixture 3401. Using methods and systems similar to those described herein, sensing device 3200 transmits the measurement data to a processing device, and a predicted value of a second characteristic of the mixture is determined. The predicted value of the second characteristic may be displayed on a user device.

In accordance with another embodiment, a plurality of sensing devices are inserted at a plurality of locations within the material of a structure. The structure may have a plurality of structural elements such as wall, floors, pillars, etc. The sensing devices obtain measurements of one or more characteristics of the material and transmit the measurement data wirelessly. The measurement data is received by a processor. The processor determines, for each structural element, a characteristic of the material within the respective structural element based on the measurement information received from the device(s) embedded in the respective structural element. The processor generates a map of the structure showing the plurality of structural elements. For each structural element, a graphical indicator is displayed on the map representing the characteristic of the material used in the respective structural element. For example, the map may be color coded, or visual patterns (stripes, dot patterns, etc.) may be used to indicate the characteristic for each structural element in the structure. A user may employ a user device to access and view the color-coded map, for example.

Figure 36:
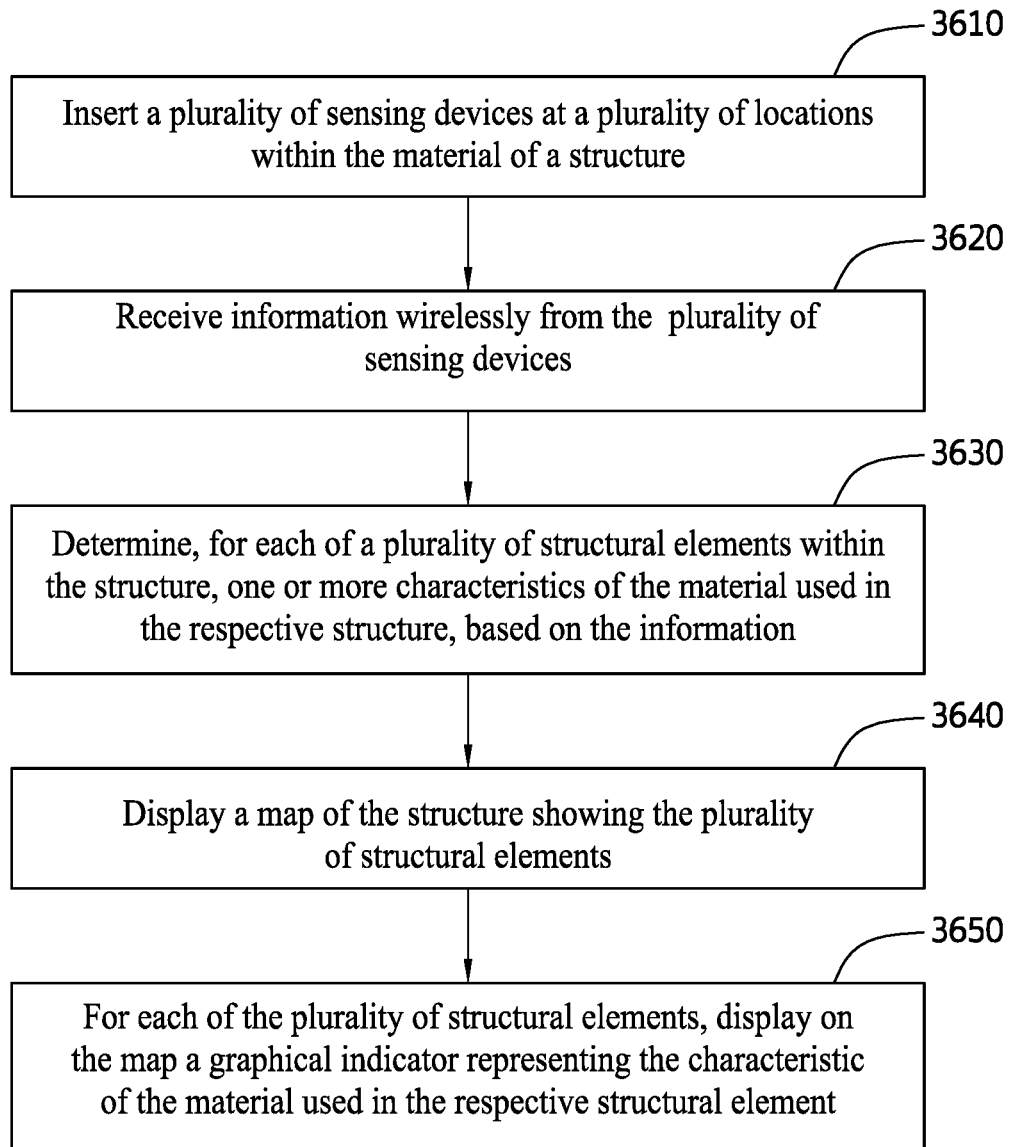
FIG. 36 is a flowchart of a method in accordance with an embodiment.

FIG. 36 is a flowchart of a method in accordance with an embodiment. At step 3610, a plurality of sensing devices are inserted at a plurality of locations within the material of a structure. At step 3620, information is received wirelessly from the plurality of sensing devices. At step 3630, for each of a plurality of structural elements within the structure, one or more characteristics of the material used in the respective structure are determined, based on the information. At step 3640, a map of the structure showing the plurality of structural elements is displayed. At step 3650, for each of the plurality of structural elements, a graphical indicator representing the characteristic of the material used in the respective structural element is displayed on the map.

In an illustrative embodiment, the method described in FIG. 36 is used in a structure containing structural elements made from concrete. Specifically, one or more sensing devices are inserted or embedded in a concrete mixture. The concrete mixture, with the sensing device(s) embedded within, is used at a construction site to form one or more structural elements of a structure. For example, a predetermined number (e.g., one thousand) sensing devices may be added, at regular intervals or at times selected by a technician, to a concrete mixture as the concrete mixture is poured down a chute from a concrete mixing truck. Consequently, several of the sensing devices are mixed into the concrete mixture, and are embedded in the concrete, as the concrete is laid in a form to create a particular structure such as a floor, wall, pillar, etc. Each sensing device remains within a respective structural element as the concrete in the structural element matures and hardens. Each sensing device is adapted to obtain measurements relating to one or more characteristics of the concrete within which it is embedded, such as temperature, humidity, pH measurements, salinity, conductivity, etc.

The various sensing devices embedded in various structural elements within a structure transmit measurement data wirelessly to a receiving device, which may be a local wireless router, for example. Multiple wireless routers may be used, as necessary. The local router then transmits the measurement data to a data manager, for example, via the Internet or other network. The data manager analyzes the measurement data and determines a second characteristic, such as strength, maturity, etc., of the concrete in the particular structural element, based on the measurement data. In this manner, the data manager obtains measurement data relating to a plurality of structural elements within a structure being built at the construction site. For example, the data manager may obtain measurement data from one or more sensing devices embedded in a first wall element, from one or more sensing devices embedded in a second wall element, from one or more sensing devices embedded in a floor element, from one or more sensing devices embedded within a pillar element, etc.

The data manager generates a map of the structure, or of a selected portion of the structure. The map indicates one or more structural elements of the structure. For each structural element, the data manager displays on the map a graphical indicator indicating a status or value of the second characteristic of the concrete associated with the respective structural element. For example, the data manager may generate a map showing various structural elements within a building that is under construction. The data manager may further add a color coding scheme in which each structural element has a color or visual pattern indicating a level of maturity or strength of the concrete used in the respective structural element.

The data manager causes the map and the graphical indicator(s) to be displayed on a user device. For example, an employee of the construction company responsible for the construction may access and view the map (and graphical indicators) using a personal computer at the company's offices. Alternatively, a technician at the construction site may employ a laptop device, tablet device, or cell phone to access and view the map (with graphical indicators).

Figure 37:
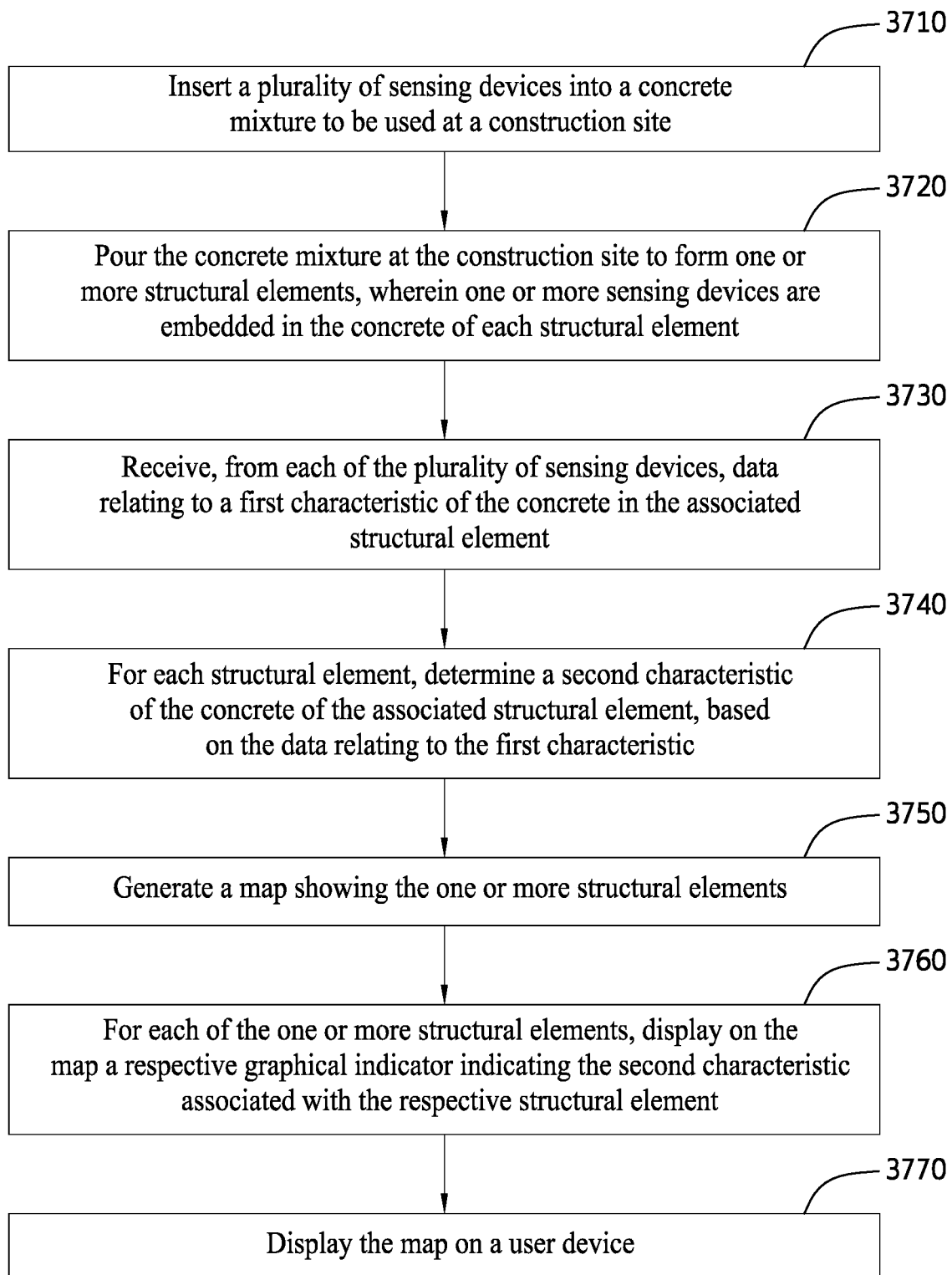
FIG. 37 is a flowchart of a method in accordance with an embodiment.
Figure 38:
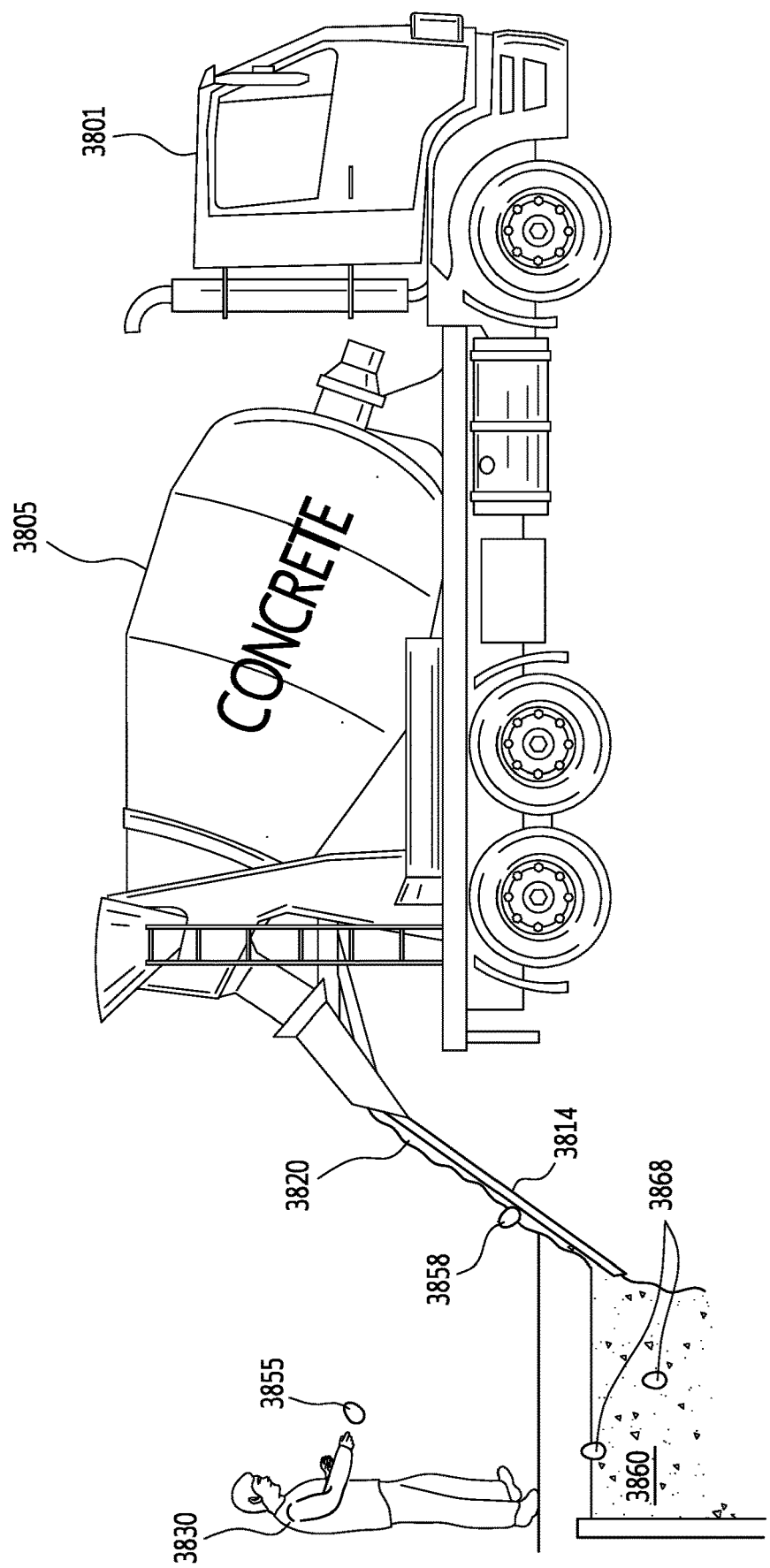
FIG. 38 shows a concrete mixing truck at a construction site in accordance with an embodiment.

FIG. 37 is a flowchart of a method in accordance with an embodiment. At step 3710, a plurality of sensing devices are inserted into a concrete mixture to be used at a construction site. Referring to FIG. 38, one or more sensing devices may be inserted into a concrete mixture as the concrete mixture is poured from a concrete mixing truck at a construction site. FIG. 38 shows a concrete mixing truck 3801, which holds a concrete mixture in a drum 3805, at a construction site. A concrete mixture 3820 is being poured from the drum 3805 via a chute 3814 into a form to create a structural element. A technician 3830 holds a sensing device 3855. The technician may drop or throw sensing device 3855 into the concrete mixture 3820 as the concrete flows down chute 3814. In this manner, the technician may place a plurality of sensing devices into the concrete mixture at selected intervals. In the illustrative embodiment, a sensing device 3858 has been added to the concrete mixture on chute 3814, and several sensing devices 3868 have been added, and are now embedded, in the concrete mixture 3860 that has been laid in a form at the construction site. As the concrete matures and dries, the sensing devices will remain embedded within the concrete.

Figure 39:
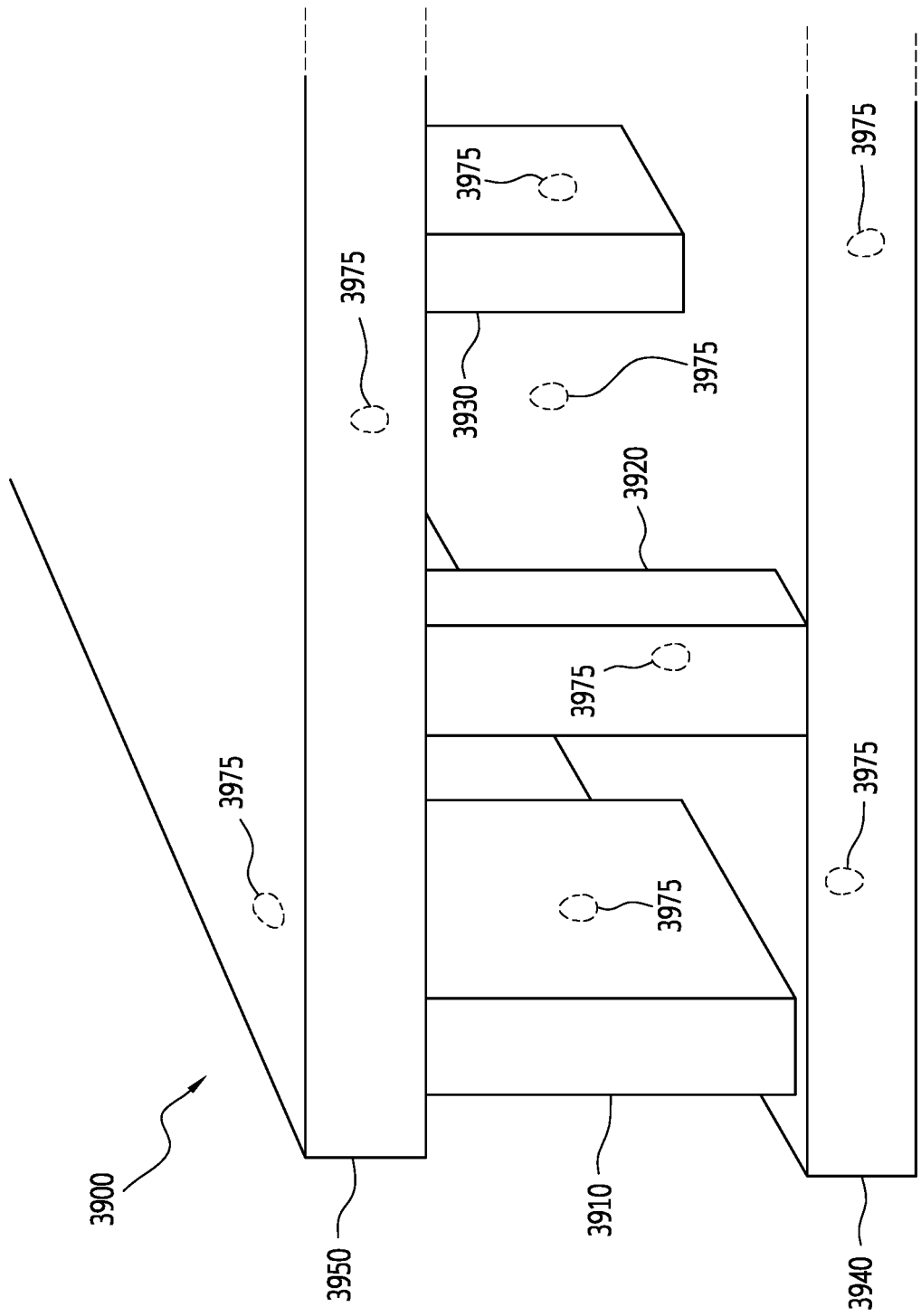
FIG. 39 shows a structure in accordance with an embodiment.

At step 3720, the concrete mixture is poured at the construction site to form one or more structural elements, wherein one or more sensing devices is embedded in the concrete of each structural element. In one embodiment, a plurality of sensing devices are embedded within a plurality of structural elements associated with a structure or project at a construction site. FIG. 39 shows a structure 3900 in accordance with an embodiment. Sensing devices are embedded within the structure in a distributed manner. For example, structure 3900 includes a floor element 3940, a wall element 3910, a pillar element 3920, a wall element 3930, and a ceiling element 3950. A plurality of sensing devices 3975 are distributed throughout the structure. One or more sensing devices is embedded within each structural element. For example, two sensing devices 3975 are embedded within floor element 3940, one sensing device 3975 is embedded in wall element 3910, etc.

Each sensing device obtains measurements relating to one or more characteristics of the concrete within which it is embedded, and transmits the measurement data wirelessly to one or more second devices. The data may be transmitted, received and collected using any one of a variety of systems and methods. For example, in one embodiment, the measurement data may be transmitted using a local wireless network and the Internet.

Figure 40:
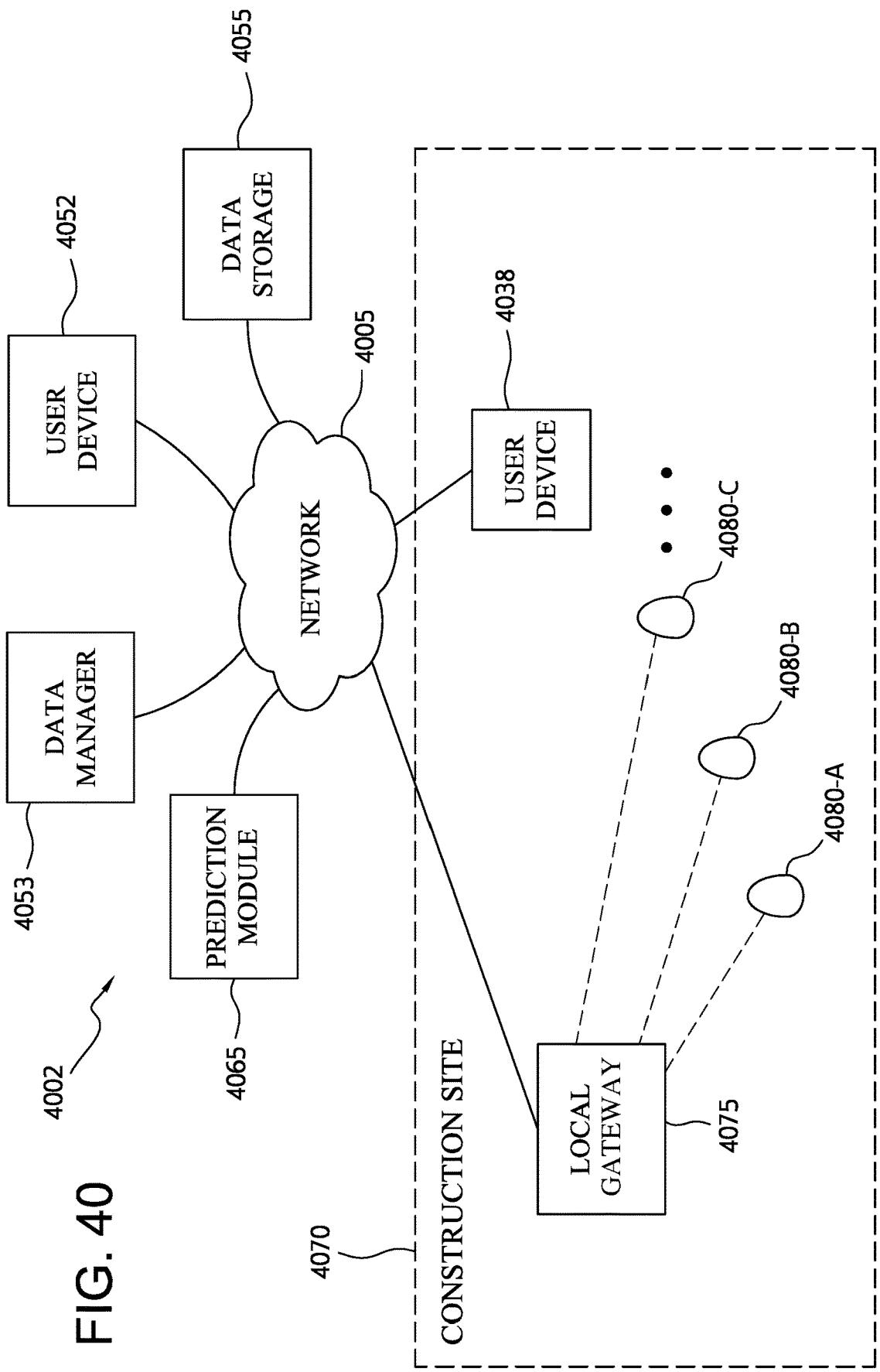
FIG. 40 shows a communication system that may be used to collect and analyze measurement data from one or more sensing devices in accordance with an embodiment.

FIG. 40 shows a communication system that may be used to collect and analyze measurement data from one or more sensing devices in accordance with an embodiment. Communication system 4002 includes a network 4005, a data manager 4053, a prediction module 4065, a first user device 4052, a data storage 4055. System 4002 also includes several components located at a construction site 4070, including a local gateway 4075, a user device 4038, and sensing device 4080-A, 4080-B, 4080-C.

Network 4005 may include one or more networks, including the Internet or another type of network. Data manager 4053 may include a processing device, or may be a software application residing and operating on a processing device. Data manager 4053 receives, analyzes, and processes measurement data generated from one or more sensing devices. Prediction module 4065 may include a processing device, or may be a software application residing and operating on a processing device. Prediction module 4065 may from time to time receive data relating to measurements of a first characteristic of concrete, obtained by one or more sensing devices, and generate a prediction of a second selected characteristic of the concrete. For example, prediction module 4065 may receive measurements of the temperature and humidity of a portion of concrete, obtained by a sensing device embedded in the concrete, and generate a prediction of the maturity of the concrete based on the temperature and humidity measurements. Data storage 4055 stores data. Data storage may include one or more disk drives, for example. User device 4052 may include a processing device employed by a user, such as a personal computer, laptop device, tablet device, cell phone, etc. For example, user device 4052 may be employed by an employee of a construction company responsible for the work done at construction site 4070.

Sensing devices 4080-A, 4080-B, 4080-C are sensing devices embedded in respective structural elements of a structure being constructed at construction site 4070, in a manner similar to that shown in FIG. 39. Local gateway 4075 is a communication device adapted to receive measurement data from sensing devices 4080 and to transmit the data to data manager 4053 via network 4005. For example, local gateway 4075 may be a wireless router device connected to network 4005. User device 4038 is a processing device employed by a person located at construction site 4070. For example, user device 4038 may be a personal computer, laptop device, tablet device, or cell phone. User device 4038 may receive data from data manager 4053 and/or from prediction module 4065, for example, via network 4005.

At step 3730, data is received from each of the plurality of sensing devices, the data relating to a first characteristic of the concrete of the associated structural element. In the illustrative embodiment of FIG. 40, each sensing device 4080-A, 4080-B, 4080-C obtains measurement data, which may be, for example, temperature data, humidity data, pH data, etc., and transmits the measurement data wirelessly. Local gateway 4075 receives the measurement data from sensing devices 4080 and transmits the measurement data to data manager 4053. Data manager 4053 may store the measurement data in data storage 4055.

Each sensing device 4080 may also transmit location data indicating its location. For example, each sensing device 4080 may include GPS capability.

At step 3740, for each structural element, a second characteristic of the associated concrete is determined, based on the data received from sensing devices within the respective structural element. Prediction module 4065 accesses the measurement data received from one or more sensing devices 4080 and generates a prediction of a second characteristic of the concrete. For example, prediction module 4065 may analyze one or more temperature and humidity measurements obtained by sensing device 4080-A, which is embedded in a particular wall element at construction site 4070. Prediction module 4065 may generate a prediction of the maturity and/or strength of the concrete in the particular wall element, based on the temperature and humidity measurements. The prediction(s) may be stored in data storage 4055.

In another embodiment, the location of a sensing device may be determined based on a triangulation method. For example, multiple local gateway devices may be located at a construction site. A signal from a sensing device may be detected and triangulation may be used to determine the location of the sensing device. Methods of using triangulation to determine location are known.

In another embodiment, each sensing device includes an accelerometer. An initial location of the sensing device may be determined when the sensing device is first activated. For example, the location of a technician who activates the sensing device may be determined. The technician then inserts the sensing device into a concrete mixture in the manner described herein. After activation, the sensing device may then continuously transmit acceleration data. The initial position of the sensing device and the subsequent motion/acceleration data may be collected and stored, and used to determine the position of the sensing device at any subsequent time. For example, integration of the acceleration data over time may provide the position of the sensing device at a selected time.

Methods for predicting maturity and strength of concrete based on measurements of the temperature, humidity and other characteristics of the concrete are known.

Figure 41:
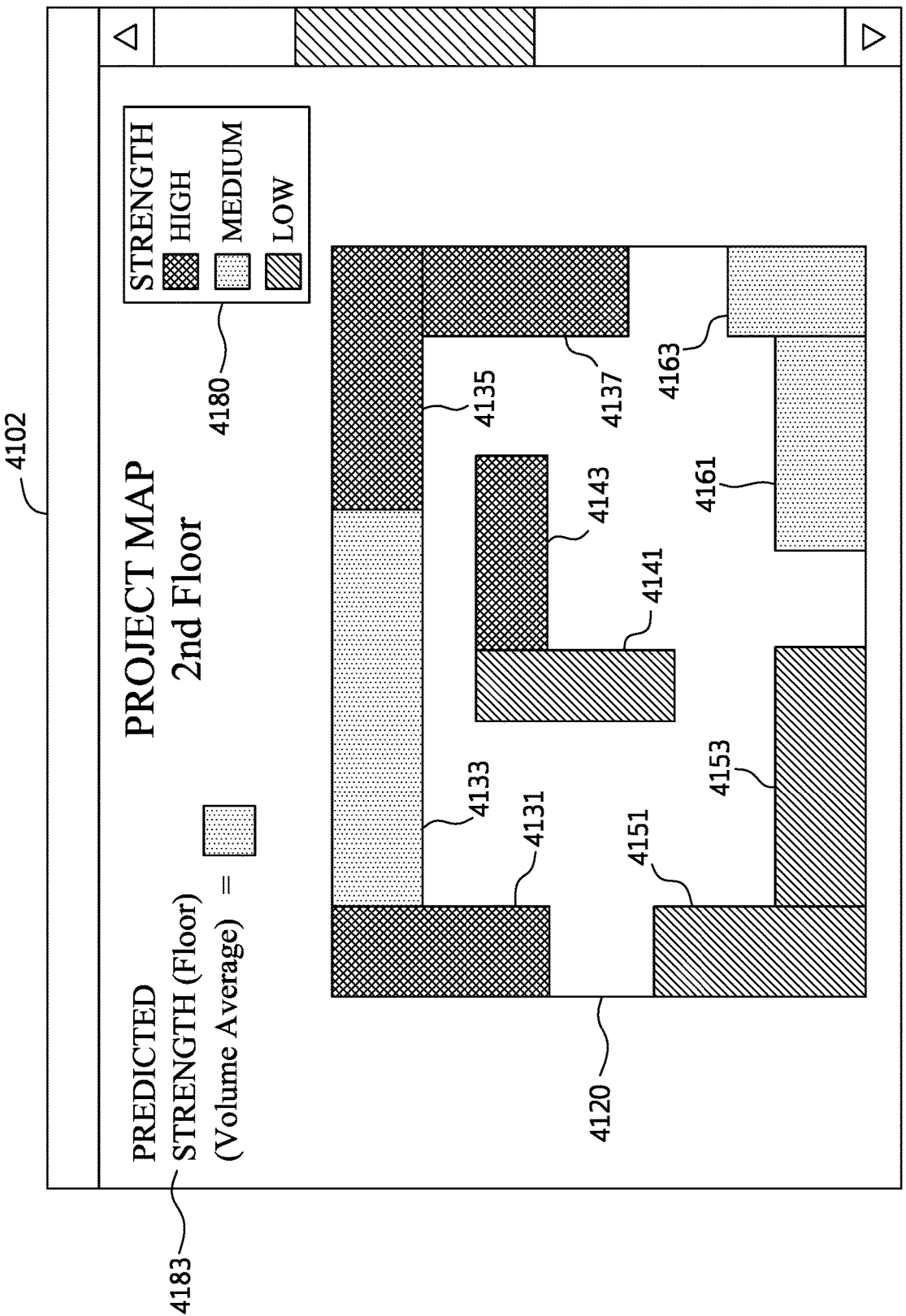
FIG. 41 shows a page that displays an exemplary map of a floor of a structure in accordance with an embodiment.

At step 3750, a map is generated showing the one or more structural elements. For example, data manager 4053 and/or prediction module 4065 may generate a map showing structural elements of the structure being constructed at construction site 4070. Data manager 4053 and/or prediction module 4065 may display the map displayed on a page, which may be a web page or another type of page, for example. FIG. 41 shows a page 4102 that displays an exemplary map 4120 of a floor of a structure in accordance with an embodiment. Map 4120 shows a plurality of structural elements located on the floor of the structure, including wall elements 4131, 4133, 4135, 4137, 4141, 4143, 4151, 4153, 4161, and 4163. The structure displayed on map 4120 may be a floor of a structure being constructed at a site, for example. In other embodiments, a map showing an entire structure, or any selected portion of a structure or building being constructed at a site, may be generated and displayed.

At step 3760, for each of the one or more structural elements, a respective graphical indicator indicating the second characteristic associated with the respective structural element is displayed on the map. In the illustrative embodiment, data manager 4053 and/or prediction module 4065 displays a color or visual pattern over each element of the structure. Page 4102 displays a key 4180 showing the colors/patterns corresponding to high strength, medium strength, and low strength. Accordingly, a color/pattern associated with high strength is displayed over structural elements 4131, 4135, 4137, and 4143. A color/pattern associated with medium strength is displayed over structural elements 4133, 4161, and 4163. A color/pattern associated with low strength is displayed over structural elements 4141, 4151, and 4153. Graphical indicators (e.g., colors, patterns, etc.) representing other characteristics such as maturity may also be displayed.

At step 3770, the map is displayed on a user device. In the illustrative embodiment, page 4102, including map 4120, may be displayed on user device 4052 and/or on user device 4038. For example, an employee of the construction company responsible for the construction at site 4070 may access page 4102 and view map 4120 via user device 4052, which may be located at the company's office. Alternatively, a technician located at construction site 4070 may access page 4102 and view map 4120 via user device 4038, which may be a cell phone, for example.

In accordance with another embodiment, a volume averaging method may be used to determine a predicted value of a characteristic of concrete for a selected portion of a structure. Any one of a variety of volume averaging methods may be used. For example, suppose that a floor of a structure includes a plurality of structural elements (walls, pillars, etc.). A predicted maturity value of each structural element on the floor may be determined using the systems and methods described herein. A value for a predicted maturity of the entire floor may then be determined using a volume average method as follows. For each structural element, determine a respective contribution value by multiplying the structural element's predicted maturity value by a percentage value representing the structural element's percentage of the total volume of concrete used on the floor. A total predicted maturity value for the floor may be determined by adding together the contribution values of all the structural elements. In this manner, a predicted maturity value may be determined for an entire floor of a structure (where the floor contains multiple structural elements), for an entire structure, for an entire project site, etc. The predicted maturity value of the floor, structure, or entire site may be displayed on a page such as page 4102.

For example, a predicted strength value for the entire floor shown in FIG. 41 may be determined using volume averaging methods described herein. Referring to FIG. 41, page 4102 includes a line 4183 that includes an indication of a predicted strength for the entire floor shown.

While one volume averaging method is described above, other volume averaging methods may be used. Similar methods may be used to determine a predicted value for any other selected characteristic, such as strength, for an entire floor, for an entire structure, for an entire site, etc.

In other embodiments, other methods may be used to determine a predicted maturity value, a predicted strength value, etc., for a floor of a structure, or for an entire structure.

Figure 42:
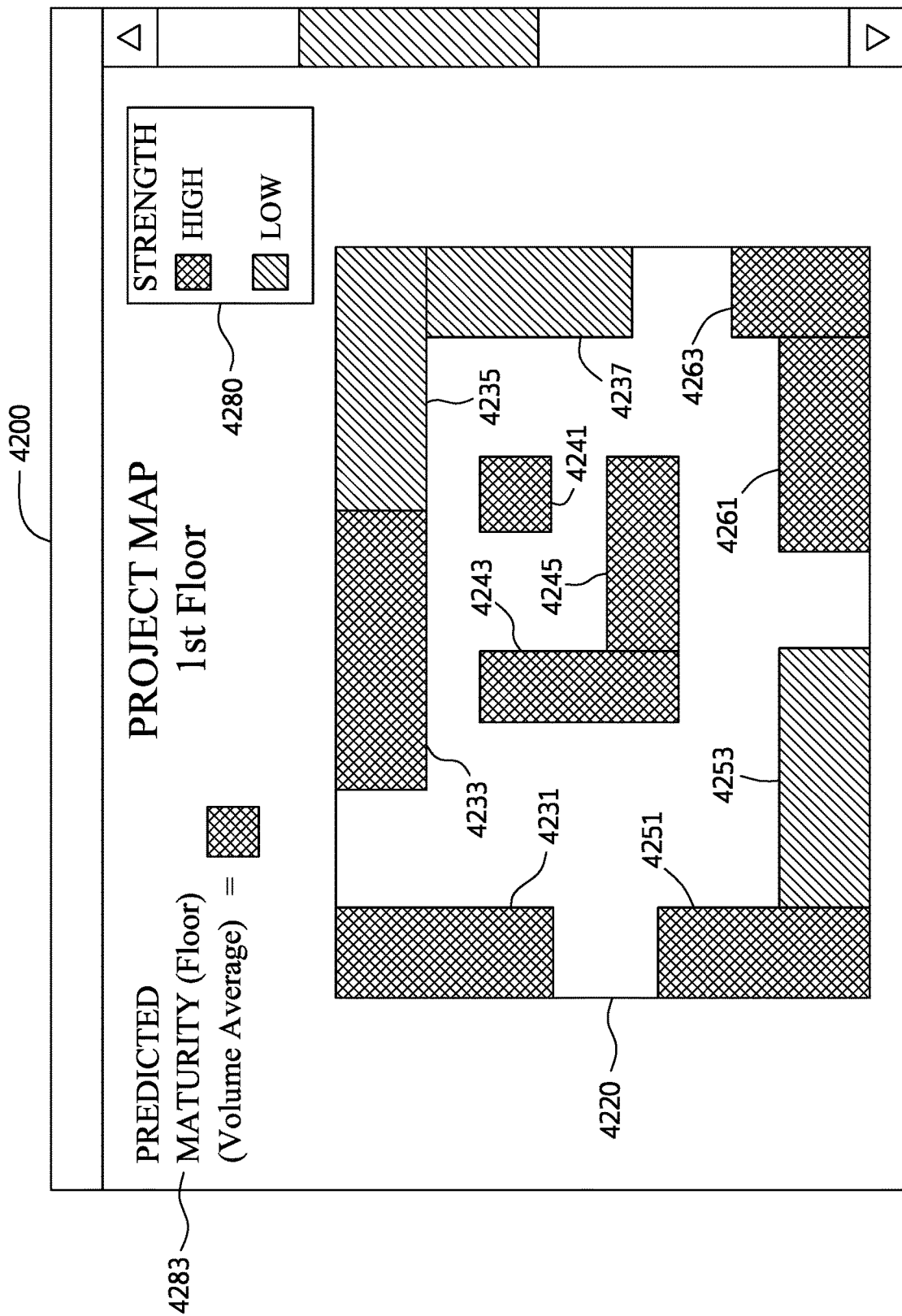
FIG. 42 shows a page that displays an exemplary map of a floor of a structure in accordance with an embodiment.

FIG. 42 shows a page 4200 that displays an exemplary map 4220 of a floor of a structure in accordance with an embodiment. Map 4220 shows a plurality of structural elements including wall elements 4231, 4233, 4235, 4237, 4241, 4243, 4245, 4251, 4253, 4261, and 4263. The structure displayed on map 4220 may be a floor of a different floor of the structure shown in FIG. 41, for example.

In the illustrative embodiment, a color or visual pattern is displayed over each element of the structure. Page 4200 displays a key 4280 showing the colors/patterns corresponding to high level of maturity and low level of maturity. Accordingly, a color/pattern associated with high maturity is displayed over structural elements 4231, 4233, 4241, 4243, 4245, 4251, 4261, and 4263. A color/pattern associated with low maturity is displayed over structural elements 4135, 4237, and 4253. Graphical indicators (e.g., colors, patterns, etc.) representing other characteristics such as maturity may also be displayed.

Page 4200 also includes a line 4283 that includes an indication of a predicted overall maturity for the entire floor shown. The overall predicted maturity value is determined using a volume averaging method.

Typically, construction work involving concrete involves a series of actions that must be performed in a particular sequence. For example, construction of a particular structure may include many steps including any of the following steps: build a form, pour concrete to build a first structure, strip formwork, build second structure on top of first structure, etc. A particular construction project may include many other steps, such as: finish a surface of a flat deck or floor, post-tensioning release (in bridge construction), etc. In many cases, a subsequent or upcoming action cannot be performed until concrete in a previously constructed structure has a required strength. For example, after concrete columns are constructed, an upper floor cannot be constructed on top of the columns until the concrete of the columns has a required strength. Improved methods and systems of determining when concrete in a particular structure is expected to achieve a required strength are needed.

In accordance with another embodiment, measurement data is received from a one or more sensing devices embedded within a concrete structure. A simulation temperature is specified by a user. The user also specifies a desired measure of strength. A predicted time when the concrete in the structure is expected to have the desired measure of strength is determined, based on the specified temperature and the measurement data. The predicted time is provided to the user. For example, the predicted time may be displayed in graphical form on a display device.

Figure 43:
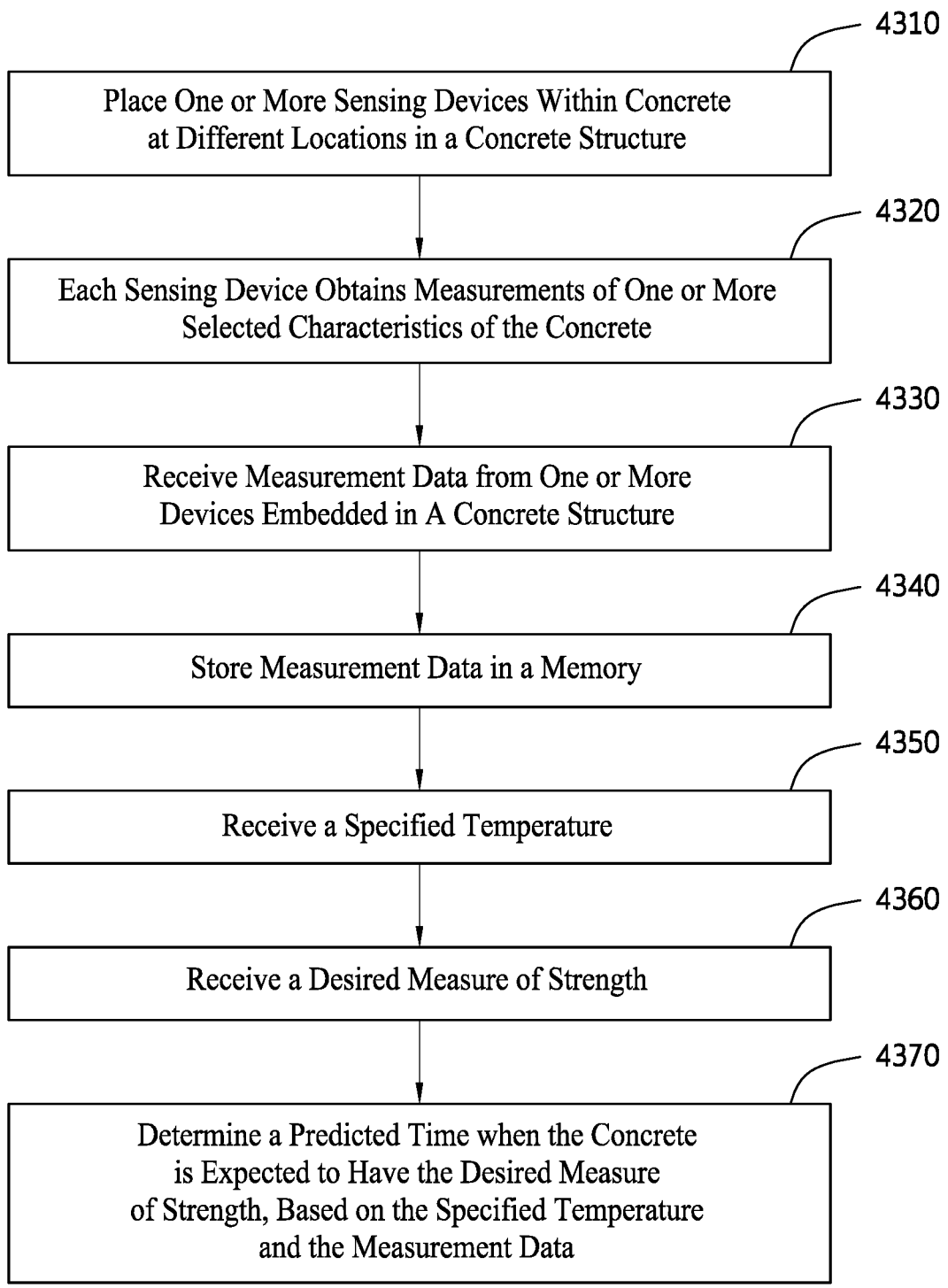
FIG. 43 is a flowchart of a method of determining a predicted time when concrete will have a desired measure of strength in accordance with an embodiment.

FIG. 43 is a flowchart of a method of determining a predicted time when concrete will have a desired measure of strength in accordance with an embodiment. At step 4310, one or more sensing devices are placed within concrete at different locations in a concrete structure. For example, referring again to FIG. 39, sensing devices such as sensing devices 3975 may be embedded within various structural elements of a structure 3900. At step 4320, each sensing device obtains measurements of one or more selected characteristics of the concrete. For example, each sensing device 3975 may obtain measurements of temperature, humidity, pH, salinity, conductivity, etc. Each sensing device 3975 transmits the measurement data wirelessly. At step 4330, measurement data is received from one or more sensing devices embedded in the concrete structure. The data may be transmitted to a processor such as data manager 4053, shown in FIG. 40. At step 4340, the measurement data is stored in a memory, such as data storage 4055 (shown in FIG. 40).

Figure 44:
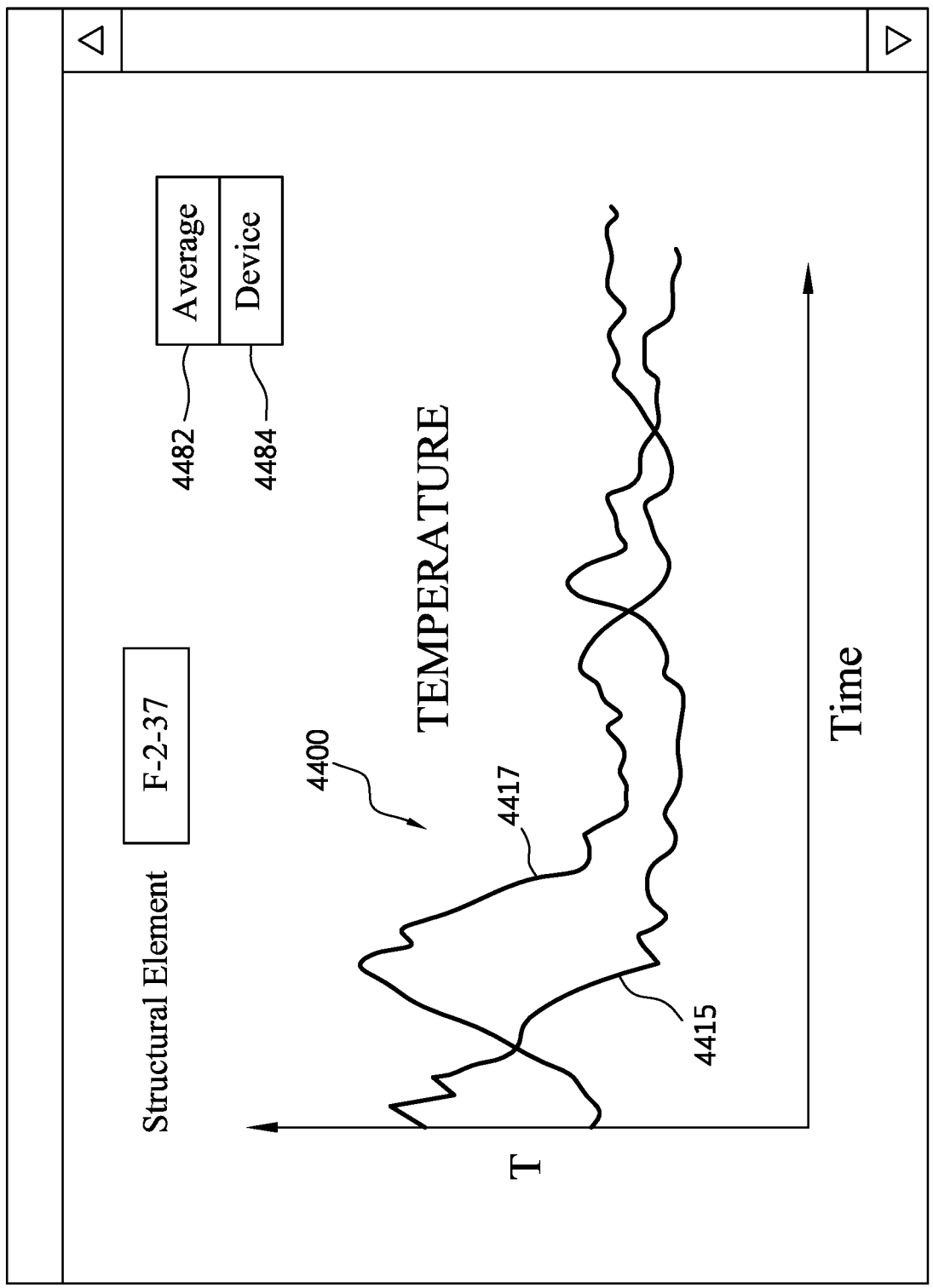
FIG. 44 shows an exemplary chart of temperature measurements over time obtained by two different sensing devices in accordance with an embodiment.

The measurement data received from the sensing devices embedded in the concrete may be used to generate visual graphics showing selected characteristics of the concrete. Such visual graphics may be displayed on a display device (such as a display of a computer or cell phone) for a user to view. For example, FIG. 44 shows an exemplary chart 4400 of temperature measurements over time obtained by two different sensing devices in accordance with an embodiment. The chart may be displayed on a display device, for example, on a web page or in another format. "Average" button 4482 and "Device" button 4484 are also displayed with chart 4400. Selection of Average Button 4482 causes a curve representing an average temperature to be displayed. The average temperature may be generated based on the temperature measurements obtained by a plurality of sensing devices. Selection of Device button 4484 causes temperature measurements obtained by a single sensing device to be displayed.

Often in concrete construction, it is necessary to determine the current strength, or predict the future strength, of the concrete within a structure or structural element. For example, it may be necessary to determine that the structure or structural element is sufficiently strong before a subsequent step in the construction is performed. For example, one or more concrete columns must have a required strength before additional structural elements (e.g., upper floors) can be constructed above the column(s).

Figure 45:
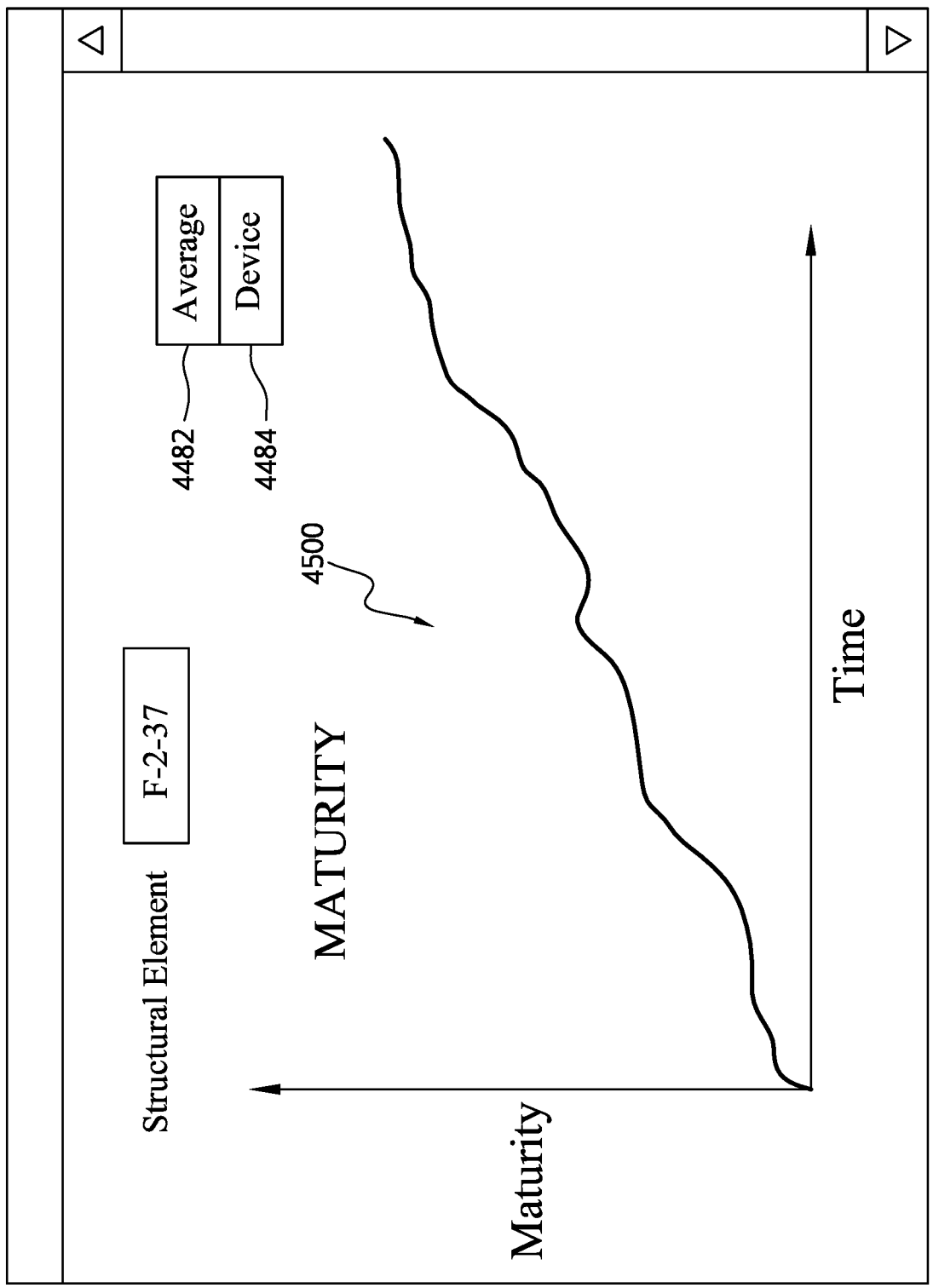
FIG. 45 shows an exemplary chart showing expected maturity of a particular structural element in accordance with an embodiment.

In one embodiment, a processor such as prediction module 4065 (shown in FIG. 40) may generate predicted values of maturity and strength for the concrete in a particular structural element based on measurements received from one or more sensing devices, and generate a chart showing the expected maturity and/or strength of the concrete in the structural element. FIG. 45 shows an exemplary chart 4500 showing expected maturity of a particular structural element in accordance with an embodiment. "Average" button 4482 and "Device" button 4484 are also displayed with chart 4500. Selection of Average Button 4482 causes an average maturity curve to be displayed. The average maturity may be generated based on the measurement data obtained by a plurality of sensing devices, for example. Selection of Device button 4484 causes a maturity curve generated based on the measurements obtained by a single sensing device to be displayed.

Figure 46:
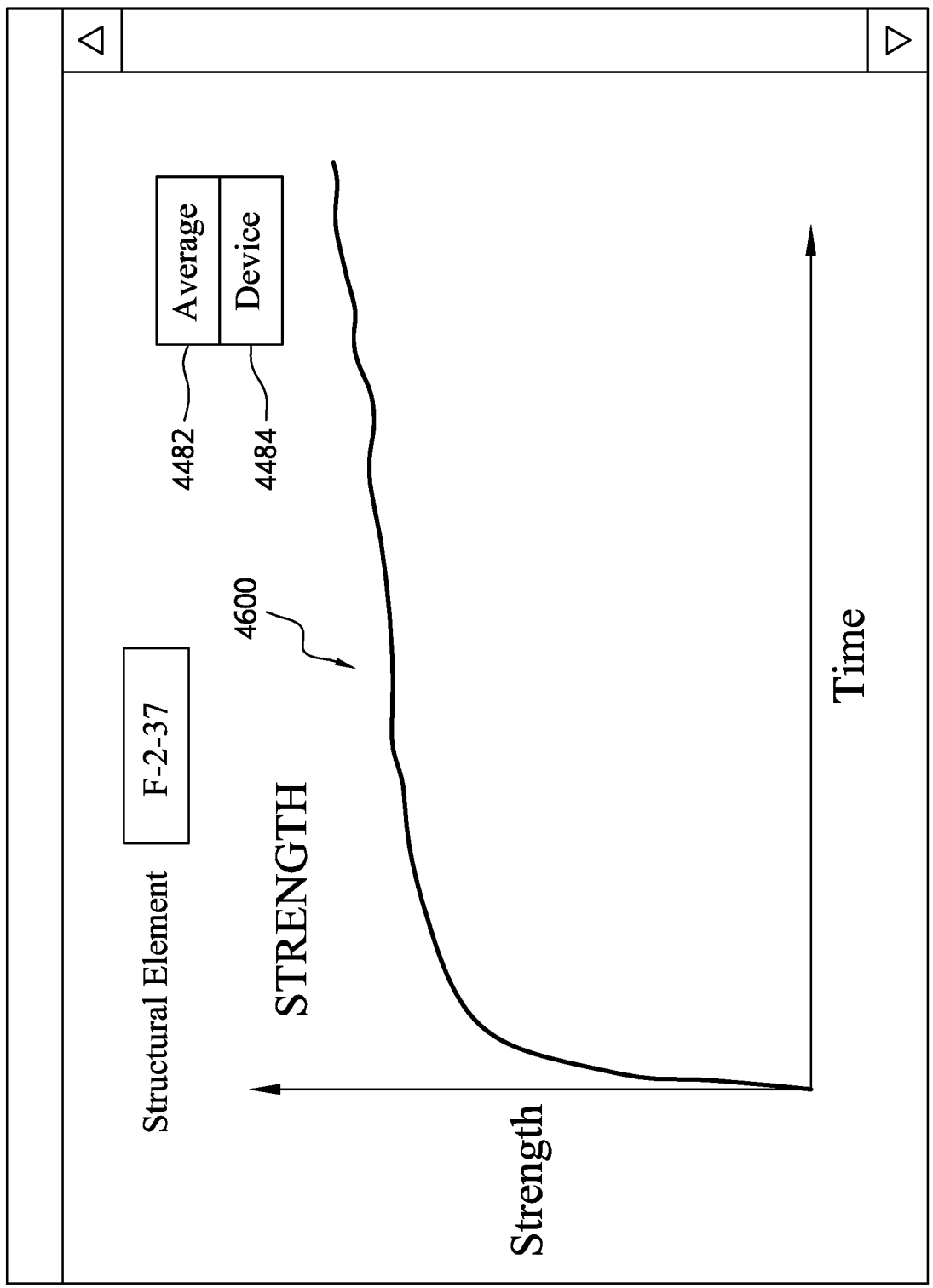
FIG. 46 shows an exemplary chart showing expected strength of a particular structural element in accordance with an embodiment.

FIG. 46 shows an exemplary chart 4600 showing expected strength of a particular structural element in accordance with an embodiment. The charts may be displayed on a display device for a user to view. "Average" button 4482 and "Device" button 4484 are also displayed with chart 4600. Selection of Average Button 4482 causes an average strength curve to be displayed. The average strength may be generated based on the measurement data obtained by a plurality of sensing devices, for example. Selection of Device button 4484 causes a strength curve generated based on the measurements obtained by a single sensing device to be displayed.

In one embodiment, a user may specify a simulation temperature and a desired measure of strength for the concrete of a particular structural element, and a predicted time when the concrete of the structural element is expected to have the desired strength is determined. For example, a user may enter a simulation temperature and a desired PSI via a page such as that shown in FIG. 47A. Page 4700 includes a field 4722 in which a user may specify a structural element, a field 4722 in which a user may specify a simulation temperature, and a field 4726 in which a user may specify a desired measure of strength. For example, page 4700 may be displayed on a user device such as user device 4038 (shown in FIG. 40). In the illustrative embodiment, the user is prompted to enter an "Action PSI."

Figure 47A:
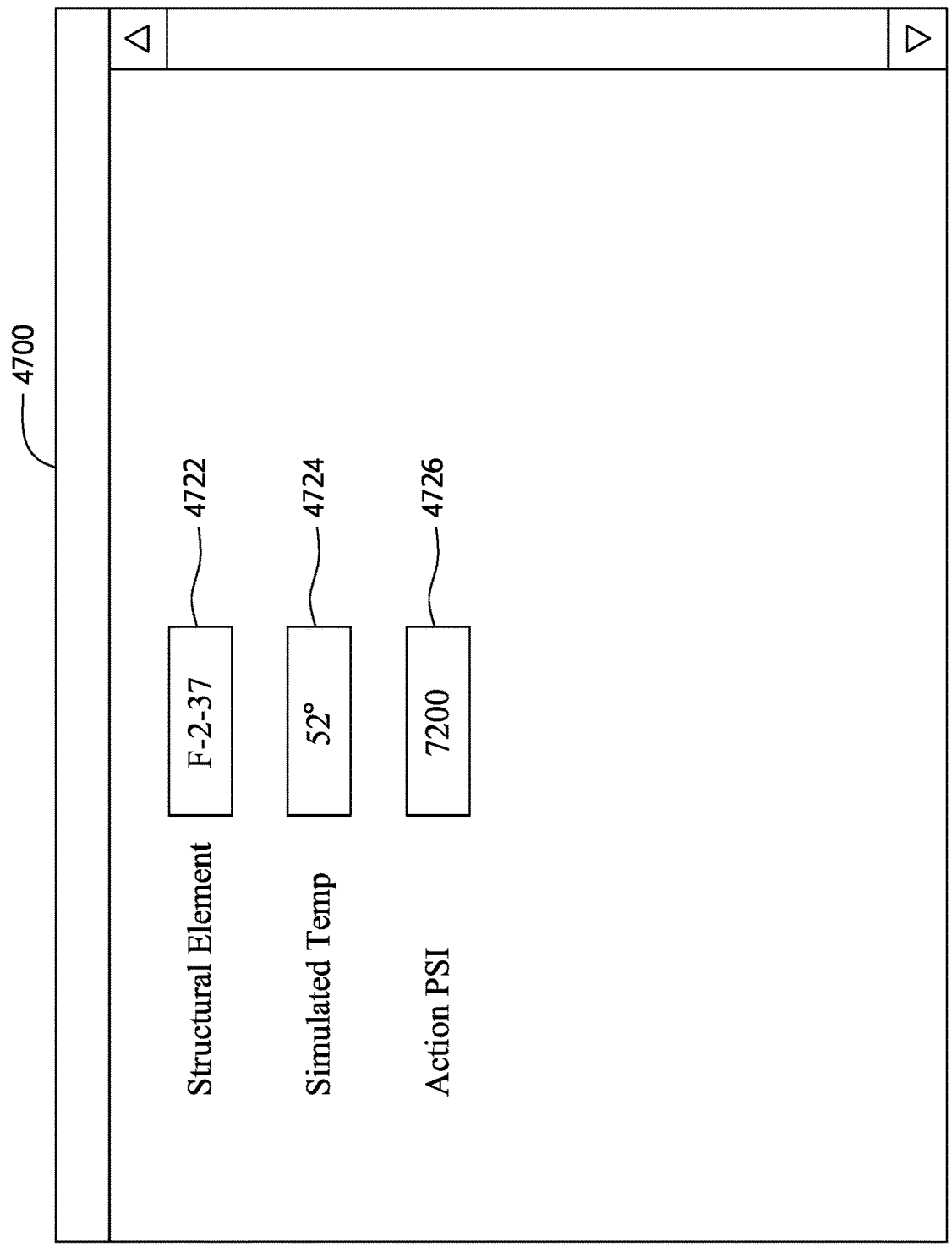
FIG. 47A shows a page that includes fields allowing a user to enter a simulation temperature and a desired measure of strength for a concrete structural element in accordance with an embodiment.

In the illustrative embodiment of FIG. 47A, the user enters an identifier of a structural element of a concrete structure in field 4722. In the illustrative embodiment, the user enters "F-2-37" as an identifier of a structural element. For example, this identifier may be associated with a wall, a section of a floor, etc. At step 4350, a specified temperature is received. In the illustrative embodiment, the user enters fifty-two degrees (52 degrees) in field 4724. At step 4360, a desired measure of strength is received. The user may enter, for example, a measure of strength that the structural element must reach before a subsequent action in the construction process may be performed. The desired measure of strength may be a measure of strength required by standards or regulations, or may be a measure of strength selected independently by the user. In the illustrative embodiment, the user enters 7200 PSI in field 4726. The identifier of the structural element, the specified temperature, and the desired measure of strength are transmitted to a processor such as data manager 4053 (shown in FIG. 40). Data manager 4053 receives the information and may store the information in storage.

At step 4370, a predicted time when the concrete is expected to have the desired measure of strength is determined, based on the specified temperature and the measurement data. Referring to FIG. 40, prediction module 4065 may generate a prediction indicating a time when the concrete in the specified structural element is expected to have a strength of 7200 PSI, if the temperature remains 52 degrees.

Figure 47B:
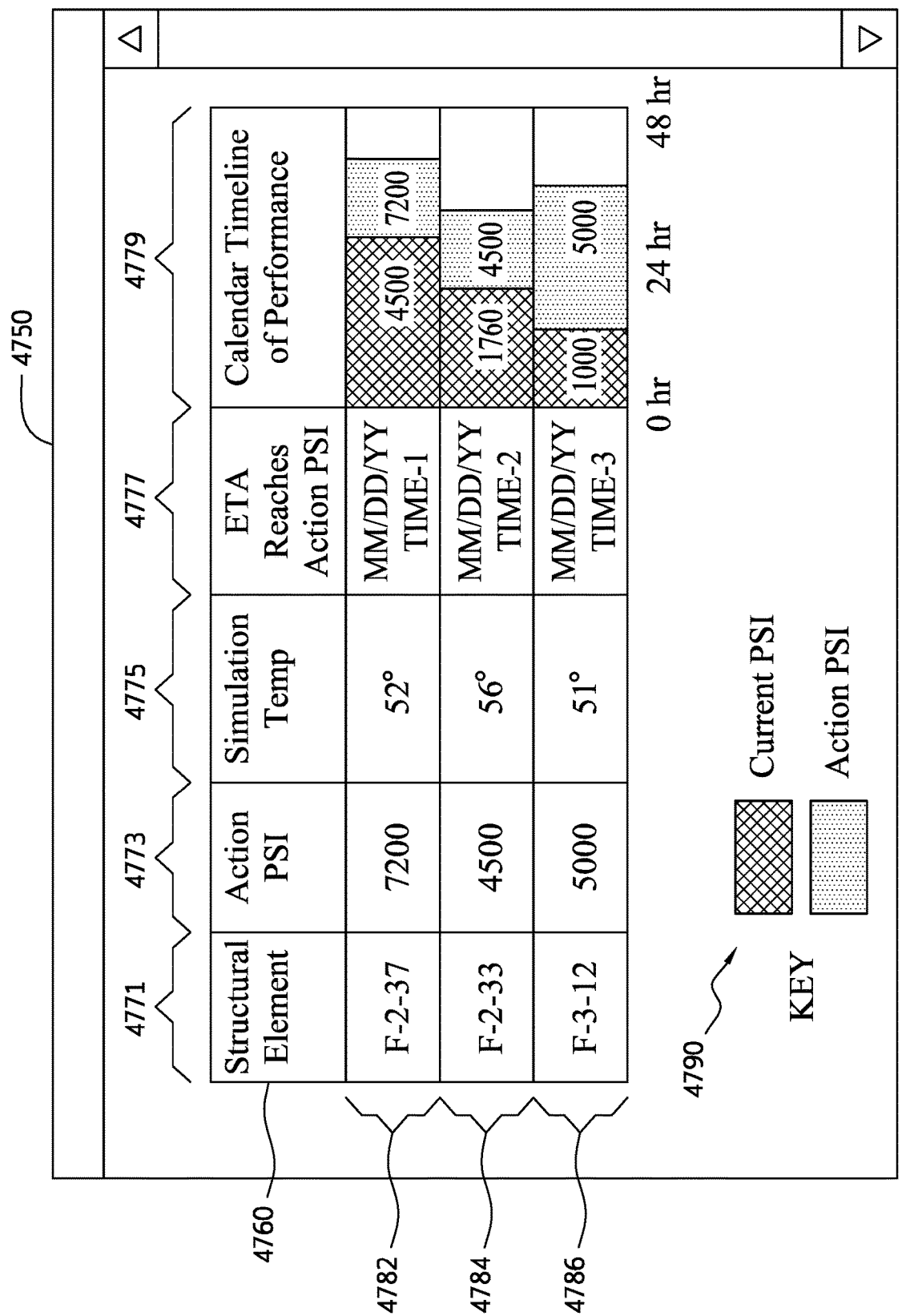
FIG. 47B shows a page that includes a table containing information related to concrete in various structural elements in accordance with an embodiment.

The predicted time indicating when the concrete will have the desired strength may be provided to the user in any suitable manner. For example, the information may be displayed on a page such as that shown in FIG. 47B. Page 4750 includes a table 4760 which includes five columns 4771, 4773, 4775, 4777, and 4779. Column 4771 contains an identifier of a structural element. Column 4773 indicates a desired strength referred to as an "Action PSI." Column 4775 specifies a simulation temperature. Column 4777 indicates an estimated time at which the concrete reaches the desired strength ("ETA Reaches Action PSI"). Column 4779 displays a graphical calendar showing a timeline of performance of the concrete. Thus, referring to record 4782, column 4771 stores the identifier "F-2-37" associated with a particular structural element. Column 4773 indicates that the selected "Action PSI" is 7200 PSI. Column 4775 indicates that the simulation temperature is 52 degrees. Column 4777 holds an estimated date and time when the concrete in the specified structural element is expected to have a strength of 7200 PSI. Column 4779 displays a graphical representation of the predicted time when the concrete is expected to reach the desired strength. In the illustrative embodiment, column 4779 includes a graphical calendar showing that the concrete is expected to reach a strength of 4500 PSI at approximately after approximately 30 hours and is expected to reach a strength of 7200 PSI after approximately 40 hours. Records 4784 and 4786 hold similar information for structural elements identified by the identifiers "F-2-33" and "F-3-12," respectively.

Page 4750 also includes a key 4790 that indicates a color code for use in reading the calendar timelines displayed in column 4779.

In accordance with another embodiment, a different estimated time required for a concrete element to reach a desired measure of strength (e.g., "Action PSI") is determined for a variety of different simulation temperatures. For example, a user may select various simulation temperatures for a particular concrete structural element, and an estimated time required for the concrete to reach the "Action PSI" is determined for each selected simulation temperature. In another embodiment illustrated in FIG. 48, a graph showing a relationship between simulation temperature and estimated time to Action PSI is displayed. In the illustrative embodiment, a page 4800 containing a graph 4820 is displayed on a user device. Graph 4820 includes a curve 4825 showing a relationship between estimated time to Action PSI and simulation temperature for structural element identified as "F-2-37."

Figure 48:
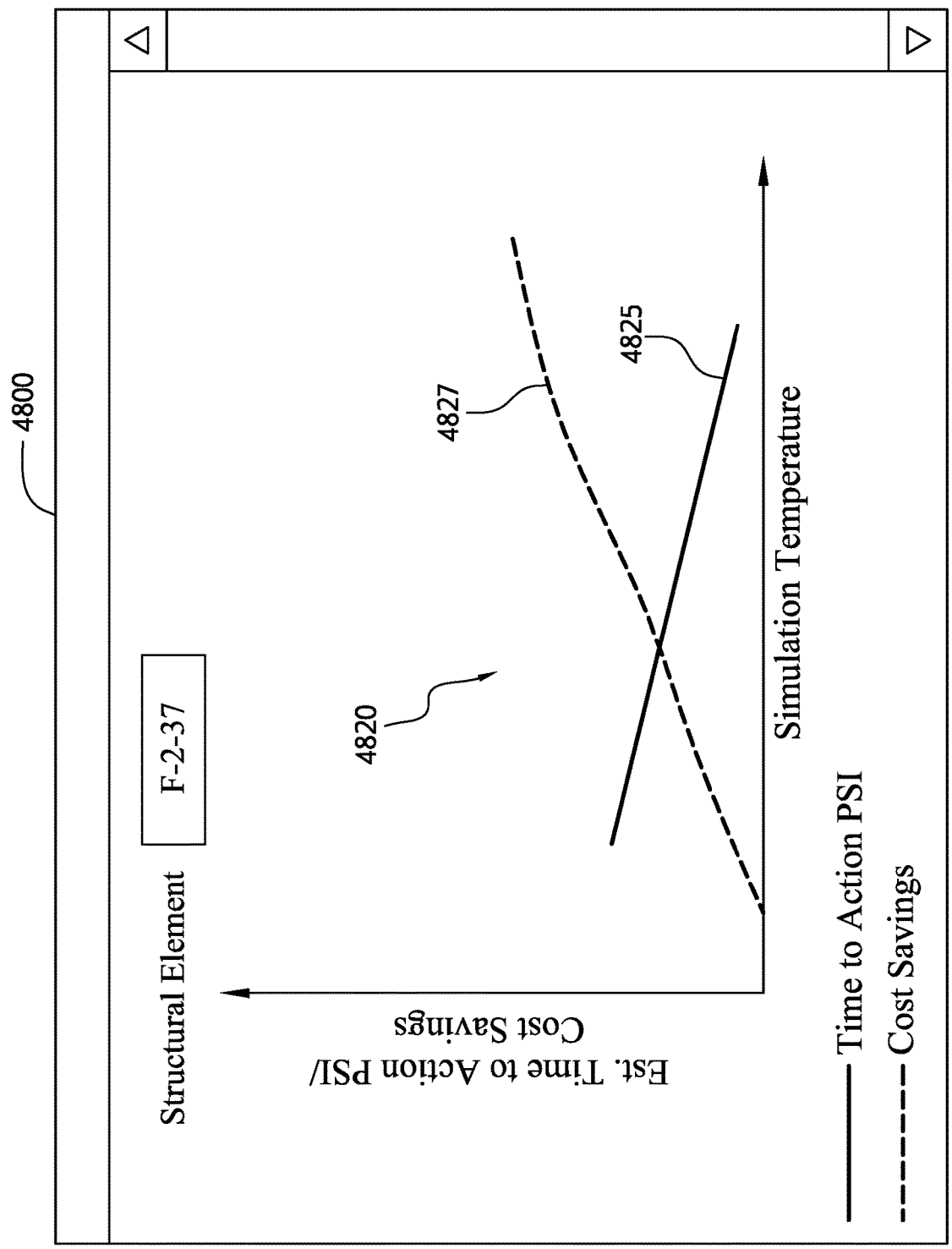
FIG. 48 shows a page containing a graph showing a relationship between simulation temperature and estimated time to a desired measure of strength for a concrete structural element in accordance with an embodiment.

In another embodiment, a measure of cost savings associated with a selected simulation temperature may be determined and provided to a user. Referring to FIG. 48, graph 4820 also displays a curve 4827 showing a cost savings associated with each point on the estimated time to Action PSI vs. simulation temperature curve 4825.

In accordance with another embodiment, information relating to predicted temperature (e.g., from a weather forecast) is included in the determination of a predicted time when concrete in a structural element is expected to have a desired measure of strength. Prediction module 4065 may access a publicly available weather forecast and obtain relevant information about the temperature at the construction site where the concrete is poured, for example. Prediction module 4065 may use this information to determine estimated timelines, in a manner similar to that discussed above.

Figure 49:
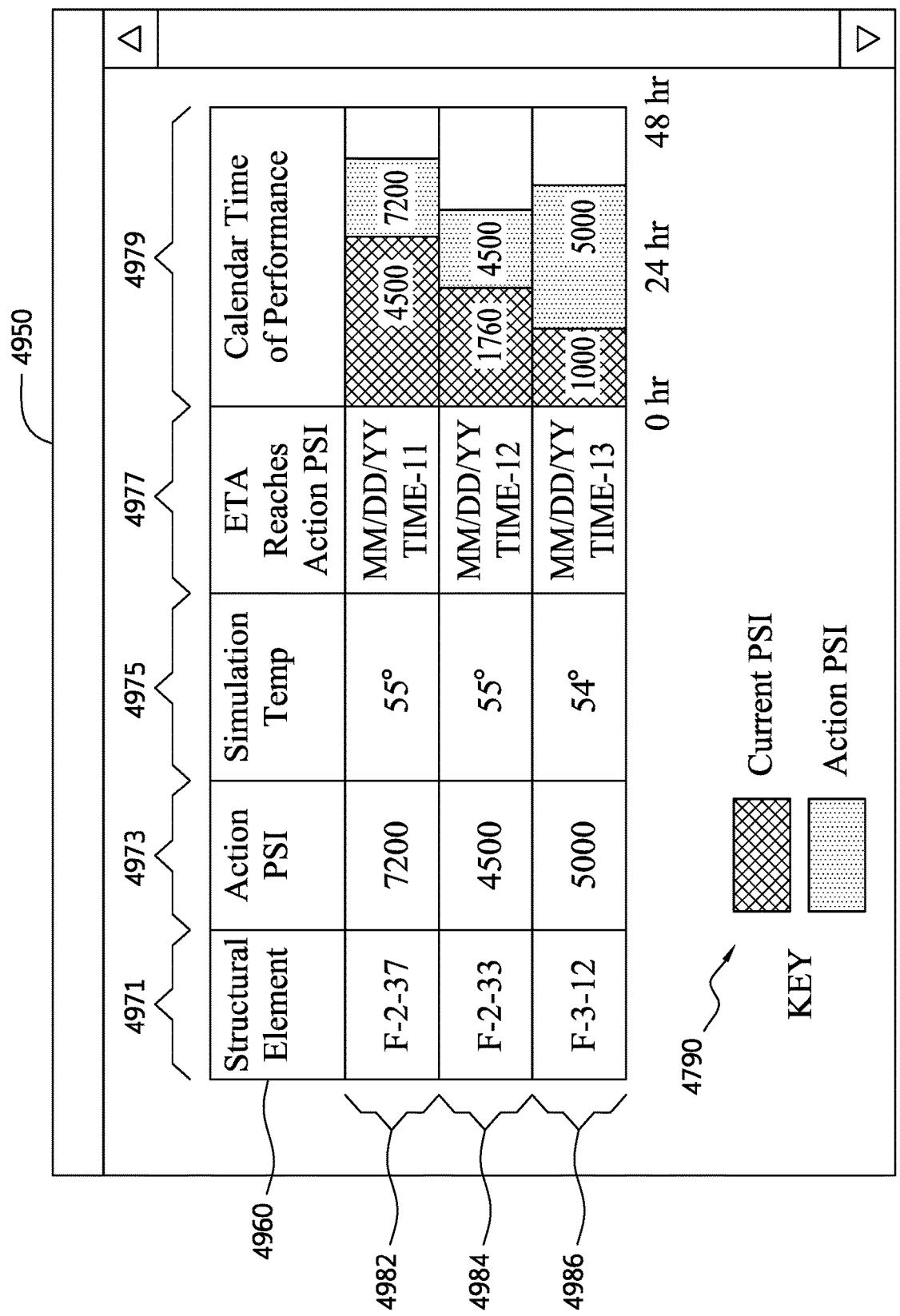
FIG. 49 shows a page that includes a table containing information related to concrete in various structural elements in accordance with an embodiment.

Information may be displayed in a table such as that shown in FIG. 49, for example. Page 4950 includes a table 4960 which includes five columns 4971, 4973, 4975, 4977, and 4979. Column 4971 contains an identifier of a structural element. Column 4973 indicates a desired strength referred to as an "Action PSI." Column 4975 specifies a forecast temperature. The forecast temperature represents a predicted temperature associated with the environment at the construction site and may be obtained from publicly available weather forecasts (or from proprietary weather forecasts), for example. Column 4977 indicates an estimated time at which the concrete reaches the desired strength ("ETA Reaches Action PSI"). Column 4979 displays a graphical calendar showing a timeline of performance of the concrete. Thus, referring to record 4982, column 4971 stores the identifier "F-2-37" associated with a particular structural element. Column 4973 indicates that the selected "Action PSI" is 7200 PSI. Column 4975 indicates that the forecast temperature is 55 degrees. Column 4977 holds an estimated date and time when the concrete in the specified structural element is expected to have a strength of 7200 PSI. Column 4979 displays a graphical calendar showing that the concrete is expected to reach a strength of 4500 PSI at approximately after approximately 26 hours and is expected to reach a strength of 7200 PSI after approximately 38 hours. Records

4984 and 4986 hold similar information for structural elements identified by the identifiers "F-2-33" and "F-3-12," respectively.

While systems and methods are described herein in the context of the concrete and construction fields, systems and methods described herein may be used for other purposes. For example, systems and methods described herein may be used to measure and analyze characteristics of water or a water mixture in a natural or artificial body of water. For example, one or more sensing devices may be inserted into a body of water and transmit measurement data relating to a first characteristic of the water (e.g., temperature, pH, the presence of a particular chemical, etc.). In a manner similar to that described above, the measurement data may be used to generate a prediction of a second characteristic of the water or water mixture.

In accordance with an embodiment, an estimated future time at which the strength of the concrete of a structure is expected to reach a measure of strength required before an upcoming action may be performed is determined, and an alert is transmitted indicating the future time and the required measure of strength.

Figure 50A:
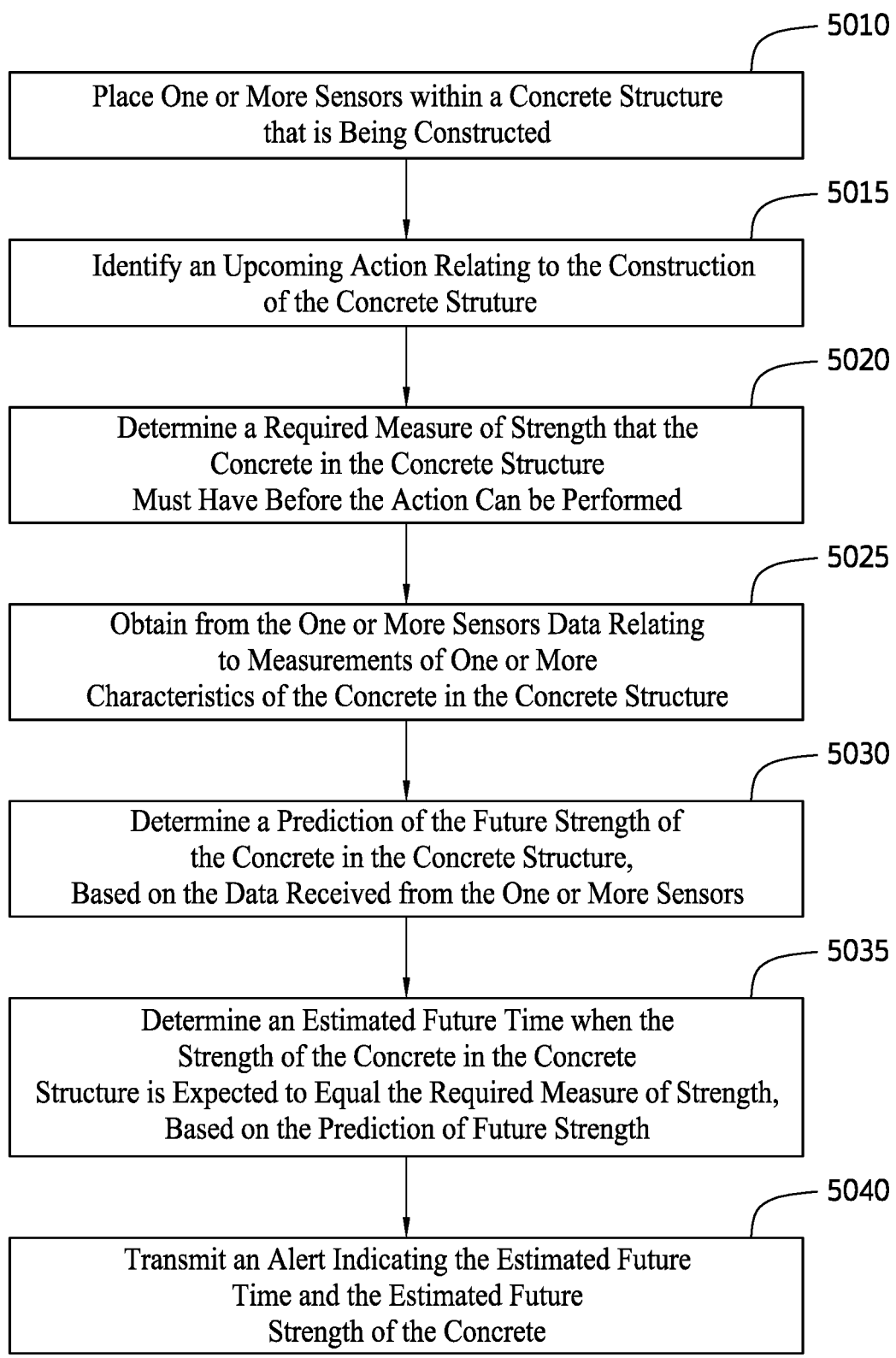
FIGS. 50A-50B include a flowchart of a method of providing an estimated future time when a concrete mixture is expected to reach a specified measure of strength in accordance with an embodiment.
Figure 50B:
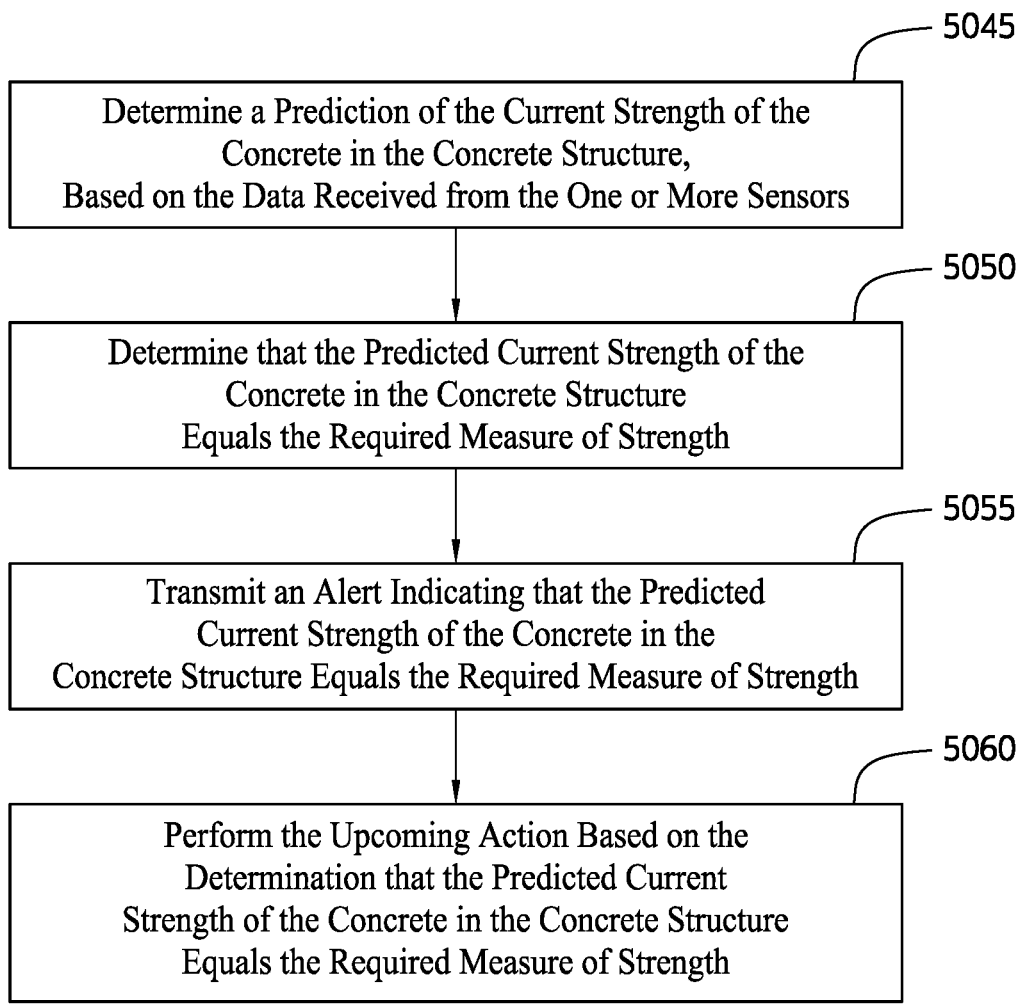

FIGS. 50A-50B include a flowchart of a method in accordance with an embodiment. At step 5010, one or more sensors are placed with a concrete structure that is being constructed. Referring again to the illustrative embodiment of FIG. 39, sensing devices such as sensing devices 3975 are embedded within various structural elements of a structure 3900.

At step 5015, an upcoming action related to the construction of the concrete structure is identified. An upcoming action may be any action in a series of actions required to complete a particular structure. For example, an upcoming action may be any of the following steps: strip formwork, finish a surface of a flat deck or floor, build an upper floor on top of columns, post-tensioning release (in bridge construction), etc.

At step 5020, a required measure of strength that the concrete in the concrete structure must have before that action can be performed is determined. For example, it may be determined that the concrete of a column must have a strength of 4500 PSI before a floor can be built on top of the column. In the illustrative embodiment of FIG. 49, record 4986 indicates that structural element "F-3-12" has an Action PSI of 5000 PSI, indicating that the concrete in the structural element must reach 5000 PSI before a subsequent action may be performed.

At step 5025, data relating to measurements of one or more characteristics of the concrete in the concrete structure is obtained from the one or more sensors. In the illustrative embodiment of FIG. 39, measurements of temperature, humidity, and other characteristics are obtained from sensing devices 3975.

At step 5030, a prediction of the future strength of the concrete in the concrete structure is determined, based on the data received from the one or more sensors. The measurement data is used to generate a prediction of the strength of the concrete in the structure. At step 5035, an estimated future time when the strength of the concrete in the concrete structure is expected to equal the required measure of strength is determined, based on the prediction of future strength. In particular, an estimated time when the strength of the concrete in the structure will achieve the strength that is required before performing the next action (constructing a floor on top of the columns, for example). Referring again to FIG. 49, record 4986 indicates that the concrete of structural element "F-3-12" will have a strength of 5000 PSI after about 30 hours.

At step 5040, an alert indicating the estimated future time and the estimated future strength of the concrete is transmitted. An alert in the form of an electronic message (e.g., email message, text message, etc.) is sent to one or more selected parties. For example, an alert indicating that the structure will have the required strength "in 30 hours" or "at approximately 1:00 PM on Wednesday" may be transmitted to a customer, to a project manager, and/or to any other designated party.

An alert is also sent when an estimate of the current strength of the concrete of the structure is equal to the required strength. Thus, at step 5045, a prediction of the current strength of the concrete in the concrete structure is determined, based on the data received from the one or more sensors. Data obtained from the sensors is used to estimate the current strength of the concrete in the structure. The estimate may be generated based on temperature measurements, for example. At step 5050, a determination is made that the predicted current strength of the concrete in the concrete structure equals the required measure of strength. Referring to FIG. 49, record 4986 indicates that the structural element "F-3-12" has an estimated current strength of 1000 PSI.

At step 5055, an alert indicating that he predicted current strength of the concrete in the concrete structure equals the required measure of strength is transmitted. If the estimated current strength of the structure equals (or exceeds) the required strength, an alert is issued to one or more selected parties. For example, an alert indicating that the "strength equals or exceeds the required strength" and an indication that the next action will be performed may be transmitted. Referring to FIG. 49, when the estimated current strength of structural element "F-3-12" reaches the Action PSI of 5000 PSI, an alert is sent.

At step 5060, the upcoming action is performed, based on the determination that the predicted current strength of the concrete in the concrete structure equals the required measure of strength. The subsequent action (e.g., constructing a floor above columns) is now performed.

In another embodiment, predictions of future strength of the concrete within a structure, and predictions as to times when the concrete will achieve specified levels of strength are used to determine possible economic costs and/or savings associated with various available options. For example, after a time when the concrete in a structure will achieve a required strength to move to a subsequent action is determined, costs associated with workforce/labor, equipment, and machinery may be used to determine an optimum action to take. For example, the savings associated with moving immediately to the next action may be compared to the cost of waiting another 24 hours. The potential savings resulting from moving immediately to the next action may be considered in deciding how to proceed. Estimated savings associated with proceeding to a next action after 12 hours, after 24 hours, after 48 hours, may be compared. Estimated savings from accelerating the drying process (e.g., by heating the concrete) may also be calculated.

In another embodiment, publicly available weather forecasts (or proprietary weather forecasts) are used to adjust a prediction of the strength or maturity of a concrete mixture. Specifically, one or more sensors adapted to obtain measurements of temperature, humidity, etc., are inserted into a concrete mixture. Temperature and humidity measurements are obtained from the sensors. In addition, a weather forecast is obtained to determine estimates of temperature and wind speed at the location where a concrete mixture is poured. Heat of hydration of the concrete mixture is determined based on the components of the concrete mixture. Other variables, such as insulation values related to the formwork used when the concrete is poured, may be used. An algorithm may be applied to determine heat flow (heat transfer within the concrete and between the concrete and the outside air) based on the temperature and wind speed predictions taken from the weather forecast. Predictions of future temperature of the concrete, and current and future strength and maturity of the concrete (and other characteristics of the concrete) are then generated based on properties of the concrete mixture such as the heat of hydration of the concrete, predicted ambient temperature (from the weather forecast), predicted wind speeds, insulation values, etc.

Measurements from the sensors in the concrete mixture, as well as actual past measurements of temperature, wind speeds, etc., may also be used to calibrate the system and/or the algorithms used.

In another embodiment, a user device, such as user device 4052 and/or 4038, may perform some or all of the method steps described herein. For example, a user device, such as a cell phone or tablet device, may perform steps 3730, 3740, 3750, 3760, and 3770 described in FIG. 37.

Figure 51A:
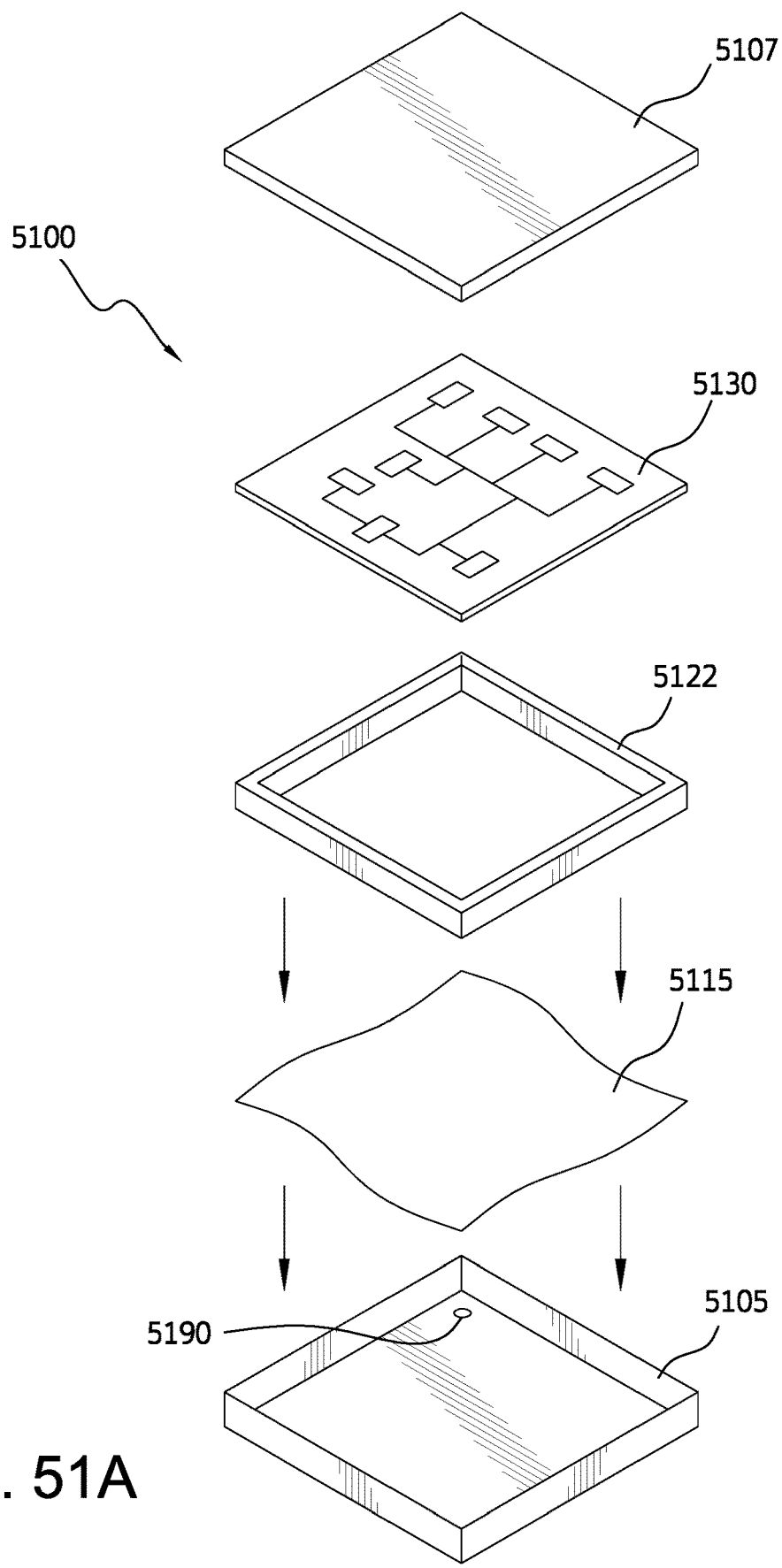
FIGS. 51A-51C show components of a sensor device in accordance with an embodiment.
Figure 51B:
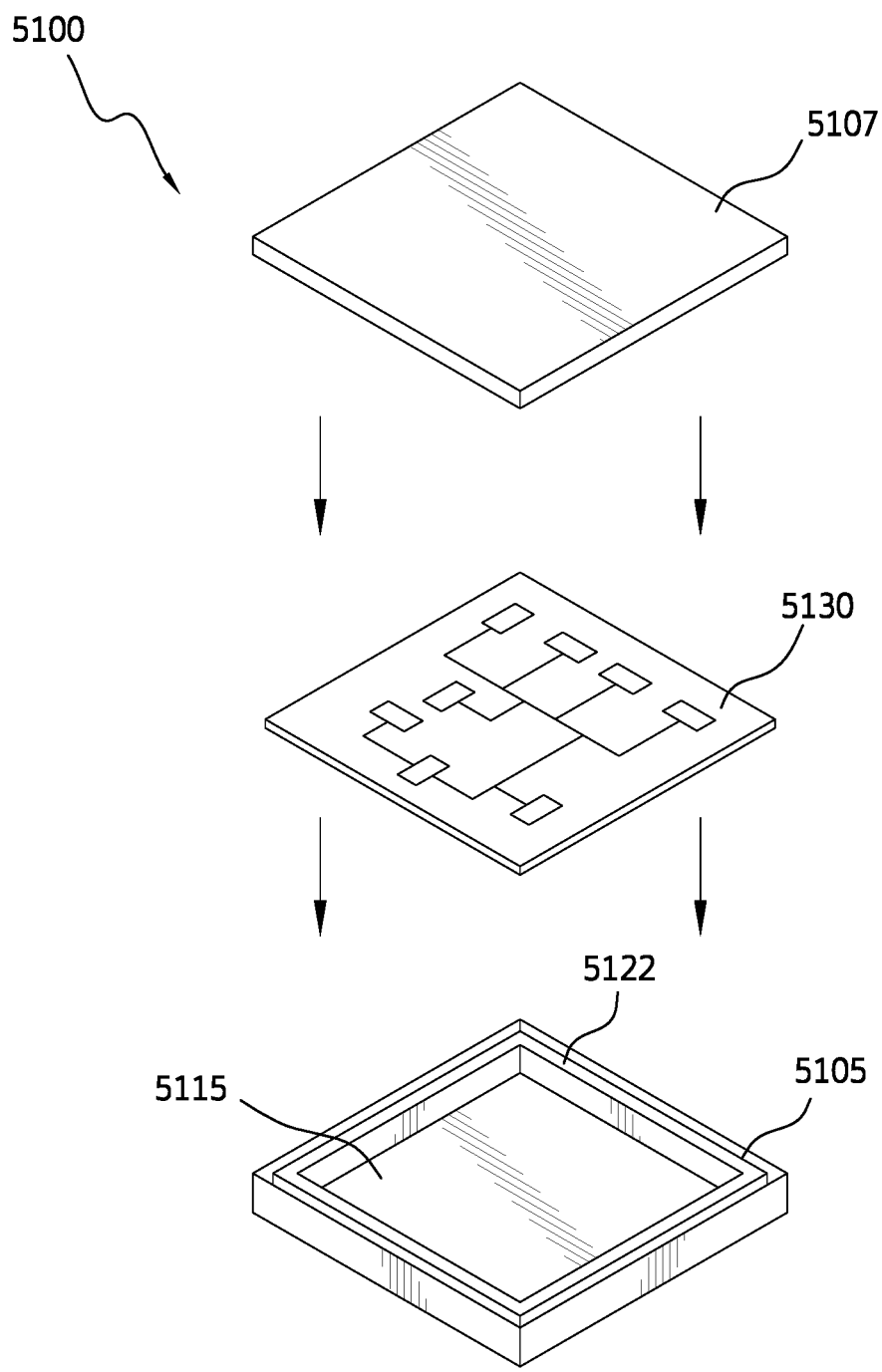
Figure 51C:
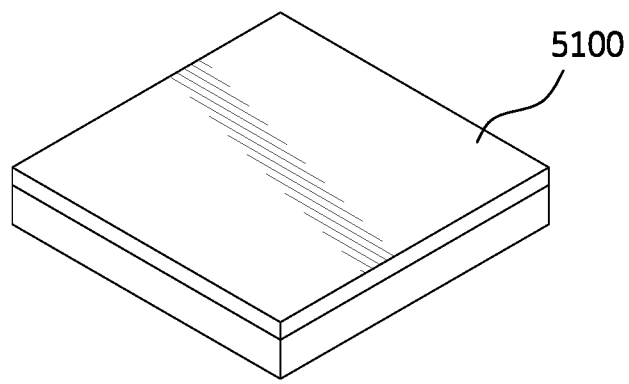

FIGS. 51A-51C show components of a sensor device in accordance with another embodiment. As shown in FIG. 51A, a sensor device 5100 includes a housing that includes an upper portion 5107 and a lower portion 5105. Upper portion 5107 and lower portion 5105 may be formed from plastic, metal, or other material. Sensor device 5100 also includes a waterproof layer 5115, a support 5122, and a sensor component 5130.

Upper portion 5107 of housing does not include any holes. Therefore, upper portion 5107 of the housing does not allow humidity to pass through from the exterior of sensor device 5100 to the interior of the sensor device.

Lower portion 5105 includes a single hole 5190 that allows humidity (water vapor) to pass into the interior of sensor device 5100 but does not allow water, concrete, or other liquids to enter. For example, hole 5190 may be a hole having a diameter of between about 1.0 millimeters and 3.0 millimeters, preferably about 2.0 millimeters. Other diameters may be used.

Sensor component 5130 includes one or more sensors adapted to measure one or more characteristics of a surrounding material (such as concrete, water, etc.) Sensor component 5130 may be, for example, a printed circuit board (PCB) containing circuit components such as resistors, capacitors, amplifiers, etc., and/or one or more sensors adapted to obtain measurements relating to one or more characteristics such as temperature, humidity, salinity, conductivity, motion, etc. Therefore, sensor component 5130 may include one or more of: a temperature sensor, a humidity sensor, a pH sensor, a salinity sensor, a conductivity sensor, a motion sensor, a sonic sensor, an accelerometer, etc. Sensor component 5130 may also include a processor. Sensor component 5130 may also include a transceiver, or may include a transmitter and/or a receiver. Sensor component 5130 may also include a battery. Alternatively, a battery or other power source may be disposed elsewhere in sensor device 5100.

Waterproof layer 5115 is made of a waterproof, breathable material that allows humidity (water vapor) to pass through the layer but does not allow liquid or concrete to pass through. For example, waterproof layer 5115 may be made waterproof, breathable fabric membrane such as Gore-Tex or other similar material.

Support 5122 is disposed between sensor component 5130 and waterproof layer 5115. Support 5122 separates waterproof layer 5115 from sensor component 5130 and thereby protects the sensors (and other electronics) of sensor component 5130 from water, liquids, concrete, etc. that may be proximate waterproof layer 5115. Thus support 5122 may maintain a predetermined distance between waterproof layer 5115 and sensor component 5130.

In the illustrative embodiment, sensor device 5100 is assembled by fitting waterproof layer 5115 and support 5122 into lower portion 5105 of the housing, as illustrated in FIGS. 51A-51B. Sensor component 5130 is then placed above support 5122, and upper portion 5107 is fitted over lower portion 5105, as illustrated in FIGS. 51B and 51C. Upper portion 5107 and lower portion 5105 may form a seal when fitted together. FIG. 51C shows sensor device 5100 in a fully assembled state.

In one embodiment, a sensor device (such as any of those described herein) may have a housing with a square or rectangular shape, with a first side having a length between about 1.5 inch and about 2.0 inches, a second side having a length between about 1.5 inch and about 2.0 inches, and a thickness between about one-eight inch and one-half inch. In a preferred embodiment, a sensor device has a housing with a square shape with sides having a length of about one and three-fourths (1.75) inches, and a thickness of about three-sixteenth (3/16) inches. The sensor device may include one or more sensors within the housing including, without limitation, a temperature sensor, a humidity sensor, etc. The sensor device may also include a transmitter.

While systems, apparatus, and methods are described herein in the context of a concrete production facility and system, a concrete mixing truck, a construction site, etc., in other embodiments, systems, apparatus and methods described herein may be used in other industries, in connection with other types of products, in other types of production facilities, in other types of vehicles and in other locations. For example, systems, apparatus, and methods described herein may be used in a vehicle (e.g., a truck) carrying other materials, including, without limitation, food products, paint products, petroleum-based products, chemicals, etc. In other embodiments, systems, apparatus, and methods described herein may be used in other locations, including, without limitation, waste sites, swimming pools, sewers, culverts, pools and reservoirs used for drainage, toxic waste sites, etc.

As mentioned above, in various embodiments, predictions of maturity, strength, and other characteristics may be generated based on measurement data received from one or more sensing devices. Relationships between curing temperature of a concrete mixture and the maturity of the concrete mixture, and between curing temperature of a concrete mixture and the strength of the concrete mixture are well-known. For example, relationships between curing temperature of a concrete mixture and the maturity of the concrete mixture, and between curing temperature of a concrete mixture and the strength of the concrete mixture are discussed in several standards established by ASTM International such as ASTM 1074. Additional examples of relationships between curing temperature and strength and between curing temperature and maturity are found in Burg, Ronald G., "The Influence of Casting and Curing Temperature on The Properties of Fresh and Hardened Concrete,"

Portland Cement Association: Research and Development Bulletin, ISBN 0-89312-143-6, Skokie, Ill., 1996.

Although the preferred embodiments of the present invention have been described herein, the above description is merely illustrative. Further modification of the invention herein disclosed will occur to those skilled in the respective arts and all such modifications are deemed to be within the scope of the invention as defined by the appended claims.

The invention claimed is:

1. A method comprising:
    inserting a plurality of sensing devices into a concrete mixture to be used at a construction site;
    pouring the concrete mixture at the construction site to form a plurality of different first structural elements that form a second structural element, wherein one or more sensing devices are embedded in the concrete of each first structural element;
    receiving, from each of the plurality of sensing devices, data relating to a first characteristic of the concrete in the associated first structural element;
    for each first structural element, determining, by a processor, a respective first value of a second characteristic of the concrete of the associated first structural element, based on the data relating to the first characteristic, thereby generating a plurality of first values of the second characteristic;
    determining, by the processor, a required measure of strength of the concrete in each of the first structural elements that is a condition for an upcoming action to be performed;
    determining, by the processor, a prediction of future strength of the concrete in each of the first structural elements, based on the data received from the plurality of sensing devices;
    determining, by the processor, an estimated future time when a strength of the concrete in each of the first structural elements is expected to equal the required measure of strength, based on the prediction of future strength;
    determining, by the processor, that a predicted current strength of the concrete in each of the first structural elements equals the required measure of strength;
    transmitting, by the processor, an alert indicating that the predicted current strength of the concrete in each of the first structural elements equals the required measure of strength;
    performing the upcoming action, based on the determining that the predicted current strength of the concrete in each of the first structural elements equals the required measure of strength; and
    displaying on a user device, the first structural elements, for each of the first structural elements, a respective first graphical indicator indicating the respective first value of the second characteristic associated with the respective first structural element, and a second value of the second characteristic associated with the first structural elements.

2. The method of claim 1, wherein each of the plurality of sensing devices includes one of a temperature sensor, an accelerometer, a pH sensor, an inductance sensor, an impedance or resistivity sensor, a sonic sensor, a pressure sensor, a conductivity sensor, a salinity sensor, a humidity sensor, and an elevation sensor.

3. The method of claim 2, wherein the first characteristic includes one of temperature, a sonic measurement, pH, inductance, impedance, resistivity, pressure, conductivity, salinity, and humidity.

4. The method of claim 3, wherein the second characteristic includes one of strength, maturity, and slump.

5. A method comprising:
    placing one or more sensors within a plurality of different first concrete structures that form a second concrete structure being constructed;
    identifying, by a processor, an upcoming action related to construction of the second concrete structure;
    determining, by the processor, a required measure of strength of the concrete in the second concrete structure that is a condition for the upcoming action to be performed;
    obtaining, by the processor, from the one or more sensors, data relating to measurements of one or more characteristics of the concrete in the second concrete structure;
    determining, by the processor, a prediction of future strength of the concrete in the second concrete structure, based on the data received from the one or more sensors;
    determining, by the processor, an estimated future time when the strength of the concrete in the second concrete structure is expected to equal the required measure of strength, based on the prediction of future strength;
    transmitting, by the processor, an alert indicating the estimated future time and the predicted future strength of the concrete;
    determining, by the processor, a prediction of current strength of the concrete in the second concrete structure, based on the data received from the one or more sensors;
    determining, by the processor, that the predicted current strength of the concrete in the second concrete structure equals the required measure of strength;
    transmitting, by the processor, an alert indicating that the predicted current strength of the concrete in the second concrete structure equals the required measure of strength; and
    performing the upcoming action, based on the determining that the predicted current strength of the concrete in the second concrete structure equals the required measure of strength.

6. The method of claim 5, wherein the upcoming action comprises at least one of: stripping formwork, finishing a surface of a flat floor, building an upper floor on top of columns, and post-tensioning release.

7. The method of claim 5, wherein the one or more characteristics comprise one of temperature, a sonic measurement, pH, inductance, impedance, resistivity, pressure, conductivity, salinity, and humidity.

8. The method of claim 1, wherein the plurality of different first structural elements includes one or more of a floor, a wall, a pillar, or a ceiling.

9. The method of claim 1, wherein the second structural element is a building.

10. The method of claim 5, wherein the plurality of different first concrete structures includes one or more of a floor, a wall, a pillar, or a ceiling.

11. The method of claim 5, wherein the second concrete structure is a building.

12. A method comprising:

inserting a plurality of sensing devices into a concrete mixture to be used at a construction site;

pouring the concrete mixture at the construction site to form a structural element, wherein the plurality of sensing devices are embedded in the concrete of the structural element;

receiving, by a processor, from each of the plurality of sensing devices, respective data relating to a first characteristic of the concrete in the structural element;

determining, by the processor, for each of the plurality of sensing devices, a respective first value of a second characteristic of the concrete of the structural element, based on the respective data relating to the first characteristic, thereby generating a plurality of first values of the second characteristic;

determining, by the processor, a required measure of strength of the concrete in the structural element that is a condition for an upcoming action to be performed;

determining, by the processor, a prediction of future strength of the concrete in the structural element, based on the data received from the plurality of sensing devices;

determining, by the processor, an estimated future time when a strength of the concrete in the structural element is expected to equal the required measure of strength, based on the prediction of future strength;

determining, by the processor, that a predicted current strength of the concrete in the structural element equals the required measure of strength;

transmitting, by the processor, an alert indicating that the predicted current strength of the concrete in the structural element equals the required measure of strength;

performing the upcoming action, based on the determining that the predicted current strength of the concrete in the structural element equals the required measure of strength;

displaying, on a user device, a display showing a visual representation of the structural element and a second value of the second characteristic of the concrete of the structural element.

13. The method of claim 12, wherein each of the plurality of sensing devices is any one of a temperature sensor, an accelerometer, a pH sensor, an inductance sensor, an impedance or resistivity sensor, a sonic sensor, a pressure sensor, a conductivity sensor, a salinity sensor, a humidity sensor, or an elevation sensor.

14. The method of claim 13, wherein the first characteristic is any one of temperature, a sonic measurement, pH, inductance, impedance, resistivity, pressure, conductivity, salinity, and humidity.

15. The method of claim 14, wherein the second characteristic is any one of strength, maturity, and slump.

16. The method of claim 12, wherein the structural element is a floor, a wall, a pillar, or a ceiling.

* * * * *